(12) United States Patent
Schimmel et al.

(10) Patent No.: US 7,521,215 B2
(45) Date of Patent: Apr. 21, 2009

(54) HUMAN AMINOACYL-TRNA SYNTHETASE POLYPEPTIDES USEFUL FOR THE REGULATION OF ANGIOGENESIS

(75) Inventors: Paul Schimmel, La Jolla, CA (US); Keisuke Wakasugi, Shizuoka (JP)

(73) Assignee: The Scripps Research Institute, La Jolla, CA (US)

( * ) Notice: Subject to any disclaimer, the term of this patent is extended or adjusted under 35 U.S.C. 154(b) by 214 days.

(21) Appl. No.: 11/444,924

(22) Filed: Jun. 1, 2006

(65) Prior Publication Data

US 2006/0216745 A1 Sep. 28, 2006

Related U.S. Application Data

(62) Division of application No. 10/240,532, filed as application No. PCT/US01/08975 on Mar. 21, 2001, now Pat. No. 7,067,126.

(60) Provisional application No. 60/193,471, filed on Mar. 31, 2000.

(51) Int. Cl.
  *C12N 9/14* (2006.01)
  *C12N 1/20* (2006.01)
  *C12N 15/00* (2006.01)
  *C07H 21/04* (2006.01)

(52) U.S. Cl. .................. 435/193; 435/252.3; 435/320.1; 536/23.2

(58) Field of Classification Search ................. 435/193, 435/252.3, 320.1; 536/23.2
  See application file for complete search history.

(56) References Cited

OTHER PUBLICATIONS

Frolova et al. [Gene, vol. 109, Issue 2, Dec. 30, 1991, pp. 291-296].*

\* cited by examiner

*Primary Examiner*—Tekchand Saidha
(74) *Attorney, Agent, or Firm*—Olson & Cepuritis, Ltd.

(57) ABSTRACT

Compositions comprising truncated tryptophanyl-tRNA synthetase polypeptides useful for regulating angiogenesis, as well as nucleic acids encoding such tRNA synthetase polypeptides are described. Methods of making and using such compositions are also disclosed.

17 Claims, 26 Drawing Sheets

SEQUENCE LISTING

<160> NUMBER OF SEQ ID NOS: 58

<210> SEQ ID NO 1
<211> LENGTH: 5174
<212> TYPE: DNA
<213> ORGANISM: Artificial Sequence
<220> FEATURE:
<221> NAME/KEY: CDS
<222> LOCATION: (3428)..(5035)
<220> FEATURE:
<223> OTHER INFORMATION: Description of Artificial Sequence: human
      full-length TyrRS in pET20B

<400> SEQUENCE: 1

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcggggc tccctttagg     180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta taagggattt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttattttc taaatacatt caaatatgta     540
tccgctcatg agacaataac cctgataaat gcttcaataa tattgaaaaa ggaagagtat     600
gagtattcaa catttccgtg tcgcccttat tcccttttt gcggcatttt gccttcctgt     660
ttttgctcac ccagaaacgc tggtgaaagt aaaagatgct gaagatcagt tgggtgcacg     720
agtgggttac atcgaactgg atctcaacag cggtaagatc cttgagagtt ttcgccccga     780
agaacgtttt ccaatgatga gcacttttaa agttctgcta tgtggcgcgg tattatcccg     840
tattgacgcc gggcaagagc aactcggtcg ccgcatacac tattctcaga tgacttggt      900 tgagtactca ccagtcacag aaaagcatct tacggatggc atgacagtaa gagaattatg     960
cagtgctgcc ataaccatga gtgataacac tgcggccaac ttacttctga caacgatcgg    1020
aggaccgaag gagctaaccg cttttttgca caacatgggg gatcatgtaa ctcgccttga    1080
```

-continued

```
tcgttgggaa ccggagctga atgaagccat accaaacgac gagcgtgaca ccacgatgcc      1140
tgcagcaatg gcaacaacgt tgcgcaaact attaactggc gaactactta ctctagcttc      1200
ccggcaacaa ttaatagact ggatggaggc ggataaagtt gcaggaccac ttctgcgctc      1260
ggcccttccg gctggctggt ttattgctga taaatctgga gccggtgagc gtgggtctcg      1320
cggtatcatt gcagcactgg ggccagatgg taagccctcc cgtatcgtag ttatctacac      1380 gacgggagt caggcaacta tggatgaacg aaatagacag atcgctgaga taggtgcctc       1440
actgattaag cattggtaac tgtcagacca agtttactca tatatacttt agattgattt      1500
aaaacttcat ttttaattta aaaggatcta ggtgaagatc cttttttgata atctcatgac     1560 caaaatccct taacgtgagt tttcgttcca ctgagcgtca ccccgtag aaaagatcaa        1620 aggatcttct tgagatcctt tttttctgcg cgtaatctgc tgcttgcaaa caaaaaaacc      1680
accgctacca gcggtggttt gtttgccgga tcaagagcta ccaactcttt ttccgaaggt      1740
aactggcttc agcagagcgc agataccaaa tactgtcctt ctagtgtagc cgtagttagg     1800
ccaccacttc aagaactctg tagcaccgcc tacatacctc gctctgctaa tcctgttacc     1860
agtggctgct gccagtggcg ataagtcgtg tcttaccggg ttggactcaa gacgatagtt     1920
accggataag gcgcagcggt cgggctgaac ggggggttcg tgcacacagc ccagcttgga     1980
gcgaacgacc tacaccgaac tgagatacct acagcgtgag ctatgagaaa gcgccacgct     2040
tcccgaaggg agaaaggcgg acaggtatcc ggtaagcggc agggtcggaa caggagagcg     2100
cacgagggag cttccagggg gaaacgcctg gtatctttat agtcctgtcg ggtttcgcca     2160
cctctgactt gagcgtcgat ttttgtgatg ctcgtcaggg gggcggagcc tatggaaaaa     2220
cgccagcaac gcggcctttt tacggttcct ggccttttgc tggccttttg ctcacatgtt     2280
ctttcctgcg ttatcccctg attctgtgga taaccgtatt accgcctttg agtgagctga     2340
taccgctcgc cgcagccgaa cgaccgagcg cagcgagtca gtgagcgagg aagcggaaga     2400
gcgcctgatg cggtattttc tccttacgca tctgtgcggt atttcacacc gcatatatgg     2460
tgcactctca gtacaatctg ctctgatgcc gcatagttaa gccagtatac actccgctat     2520
cgctacgtga ctgggtcatg gctgcgcccc gacacccgcc aacacccgct gacgcgccct     2580
gacgggcttg tctgctcccg gcatccgctt acagacaagc tgtgaccgtc tccgggagct     2640
gcatgtgtca gaggttttca ccgtcatcac cgaaacgcgc gaggcagctg cggtaaagct     2700
catcagcgtg gtcgtgaagc gattcacaga tgtctgcctg ttcatccgcg tccagctcgt     2760
tgagtttctc cagaagcgtt aatgtctggc ttctgataaa gcgggccatg ttaagggcgg     2820
ttttttcctg tttggtcact gatgcctccg tgtaggggg atttctgttc atgggggtaa      2880
tgataccgat gaaacgagag aggatgctca cgatacgggg tactgatgat gaacatgccc     2940
ggttactgga acgttgtgag ggtaaacaac tggcggtatg gatgcggcgg gaccagagaa     3000
aaatcactca gggtcaatgc cagcgcttcg ttaatacaga tgtaggtgtt ccacagggta     3060
gccagcagca tcctgcgatg cagatccgga acataatggt gcagggcgct gacttccgcg     3120
tttccagact ttacgaaaca cggaaaccga agaccattca tgttgttgct caggtcgcag     3180
acgttttgca gcagcagtcg cttcacgttc gctcgcgtat cggtgattca ttctgctaac     3240
cagtaaggca accccgccag cctagccggg tcctcaacga caggagcacg atcatgcgca     3300
cccgtggcca ggacccaacg ctgcccgaga tctcgatccc gcgaaattaa tacgactcac     3360
tatagggaga ccacaacggt ttccctctag aaataatttt gtttaacttt aagaaggaga     3420 tatacat atg ggg gac gct ccc agc cct gaa gag aaa ctg cac ctt atc       3469
```

```
            Met Gly Asp Ala Pro Ser Pro Glu Glu Lys Leu His Leu Ile
              1               5                  10 acc cgg aac ctg cag gag gtt ctg ggg gaa gag aag ctg aag gag ata    3517
Thr Arg Asn Leu Gln Glu Val Leu Gly Glu Glu Lys Leu Lys Glu Ile
 15              20                  25                  30 ctg aag gag cgg gaa ctt aaa att tac tgg gga acg gca acc acg ggc    3565
Leu Lys Glu Arg Glu Leu Lys Ile Tyr Trp Gly Thr Ala Thr Thr Gly
         35                  40                  45 aaa cca cat gtg gct tac ttt gtg ccc atg tca aag att gca gac ttc    3613
Lys Pro His Val Ala Tyr Phe Val Pro Met Ser Lys Ile Ala Asp Phe
             50                  55                  60 tta aag gca ggg tgt gag gta aca att ctg ttt gcg gac ctc cac gca    3661
Leu Lys Ala Gly Cys Glu Val Thr Ile Leu Phe Ala Asp Leu His Ala
 65                  70                  75 tac ctg gat aac atg aaa gcc cca tgg gaa ctt cta gaa ctc cga gtc    3709
Tyr Leu Asp Asn Met Lys Ala Pro Trp Glu Leu Leu Glu Leu Arg Val
     80                  85                  90 agt tac tat gag aat gtg atc aaa gca atg ctg gag agc att ggt gtg    3757
Ser Tyr Tyr Glu Asn Val Ile Lys Ala Met Leu Glu Ser Ile Gly Val
 95                 100                 105                 110 ccc ttg gag aag ctc aag ttc atc aaa ggc act gat tac cag ctc agc    3805
Pro Leu Glu Lys Leu Lys Phe Ile Lys Gly Thr Asp Tyr Gln Leu Ser
                115                 120                 125 aaa gag tac aca cta gat gtg tac aga ctc tcc tcc gtg gtc aca cag    3853
Lys Glu Tyr Thr Leu Asp Val Tyr Arg Leu Ser Ser Val Val Thr Gln
            130                 135                 140 cac gat tcc aag aag gct gga gct gag gtg gta aag cag gtg gag cac    3901
His Asp Ser Lys Lys Ala Gly Ala Glu Val Val Lys Gln Val Glu His
        145                 150                 155 cct ttg ctg agt ggc ctc tta tac ccc gga ctg cag gct ttg gat gaa    3949
Pro Leu Leu Ser Gly Leu Leu Tyr Pro Gly Leu Gln Ala Leu Asp Glu
    160                 165                 170 gag tat tta aaa gta gat gcc caa ttt gga ggc att gat cag aga aag    3997
Glu Tyr Leu Lys Val Asp Ala Gln Phe Gly Gly Ile Asp Gln Arg Lys
175                 180                 185                 190 att ttc acc ttt gca gag aag tac ctc cct gca ctt ggc tat tca aaa    4045
Ile Phe Thr Phe Ala Glu Lys Tyr Leu Pro Ala Leu Gly Tyr Ser Lys
                195                 200                 205 cgg gtc cat ctg atg aat cct atg gtt cca gga tta aca ggc agc aaa    4093
Arg Val His Leu Met Asn Pro Met Val Pro Gly Leu Thr Gly Ser Lys
            210                 215                 220 atg agc tct tca gaa gag gag tcc aag att gat ctc ctt gat cgg aag    4141
Met Ser Ser Ser Glu Glu Glu Ser Lys Ile Asp Leu Leu Asp Arg Lys
        225                 230                 235 gag gat gtg aag aaa aaa ctg aag aag gcc ttc tgt gag cca gga aat    4189
Glu Asp Val Lys Lys Lys Leu Lys Lys Ala Phe Cys Glu Pro Gly Asn
    240                 245                 250 gtg gag aac aat ggg gtt ctg tcc ttc atc aag cat gtc ctt ttt ccc    4237
Val Glu Asn Asn Gly Val Leu Ser Phe Ile Lys His Val Leu Phe Pro
255                 260                 265                 270 ctt aag tcc gag ttt gtg atc cta cga gat gag aaa tgg ggt gga aac    4285
Leu Lys Ser Glu Phe Val Ile Leu Arg Asp Glu Lys Trp Gly Gly Asn
                275                 280                 285 aaa acc tac aca gct tac gtg gac ctg gaa aag gac ttt gct gct gag    4333
Lys Thr Tyr Thr Ala Tyr Val Asp Leu Glu Lys Asp Phe Ala Ala Glu
            290                 295                 300 gtt gta cat cct gga gac ctg aag aat tct gtt gaa gtc gca ctg aac    4381
Val Val His Pro Gly Asp Leu Lys Asn Ser Val Glu Val Ala Leu Asn
        305                 310                 315
```

```
aag ttg ctg gat cca atc cgg gaa aag ttt aat acc cct gcc ctg aaa    4429
Lys Leu Leu Asp Pro Ile Arg Glu Lys Phe Asn Thr Pro Ala Leu Lys
    320                 325                 330 aaa ctg gcc agc gct gcc tac cca gat ccc tca aag cag aag cca atg    4477
Lys Leu Ala Ser Ala Ala Tyr Pro Asp Pro Ser Lys Gln Lys Pro Met
335                 340                 345                 350 gcc aaa ggc cct gcc aag aat tca gaa cca gag gag gtc atc cca tcc    4525
Ala Lys Gly Pro Ala Lys Asn Ser Glu Pro Glu Glu Val Ile Pro Ser
                355                 360                 365 cgg ctg gat atc cgt gtg ggg aaa atc atc act gtg gag aag cac cca    4573
Arg Leu Asp Ile Arg Val Gly Lys Ile Ile Thr Val Glu Lys His Pro
            370                 375                 380 gat gca gac agc ctg tat gta gag aag att gac gtg ggg gaa gct gaa    4621
Asp Ala Asp Ser Leu Tyr Val Glu Lys Ile Asp Val Gly Glu Ala Glu
        385                 390                 395 cca cgg act gtg gtg agc ggc ctg gta cag ttc gtg ccc aag gag gaa    4669
Pro Arg Thr Val Val Ser Gly Leu Val Gln Phe Val Pro Lys Glu Glu
    400                 405                 410 ctg cag gac agg ctg gta gtg gtg ctg tgc aac ctg aaa ccc cag aag    4717
Leu Gln Asp Arg Leu Val Val Val Leu Cys Asn Leu Lys Pro Gln Lys
415                 420                 425                 430 atg aga gga gtc gag tcc caa ggc atg ctt ctg tgt gct tct ata gaa    4765
Met Arg Gly Val Glu Ser Gln Gly Met Leu Leu Cys Ala Ser Ile Glu
                435                 440                 445 ggg ata aac cgc cag gtt gaa cct ctg gac cct ccg gca ggc tct gct    4813
Gly Ile Asn Arg Gln Val Glu Pro Leu Asp Pro Pro Ala Gly Ser Ala
            450                 455                 460 cct ggt gag cac gtg ttt gtg aag ggc tat gaa aag ggc caa cca gat    4861
Pro Gly Glu His Val Phe Val Lys Gly Tyr Glu Lys Gly Gln Pro Asp
        465                 470                 475 gag gag ctc aag ccc aag aag aaa gtc ttc gag aag ttg cag gct gac    4909
Glu Glu Leu Lys Pro Lys Lys Lys Val Phe Glu Lys Leu Gln Ala Asp
    480                 485                 490 ttc aaa att tct gag gag tgc atc gca cag tgg aag caa acc aac ttc    4957
Phe Lys Ile Ser Glu Glu Cys Ile Ala Gln Trp Lys Gln Thr Asn Phe
495                 500                 505                 510 atg acc aag ctg ggc tcc att tcc tgt aaa tcg ctg aaa ggg ggg aac    5005
Met Thr Lys Leu Gly Ser Ile Ser Cys Lys Ser Leu Lys Gly Gly Asn
                515                 520                 525 att agc ctc gag cac cac cac cac cac cac tgagatccgg ctgctaacaa    5055
Ile Ser Leu Glu His His His His His His
            530                 535 agcccgaaag gaagctgagt tggctgctgc caccgctgag caataactag cataacccct    5115
tggggcctct aaacgggtct tgagggggttt tttgctgaaa ggaggaacta tatccggat    5174

<210> SEQ ID NO 2
<211> LENGTH: 536
<212> TYPE: PRT
<213> ORGANISM: Artificial Sequence
<220> FEATURE:
<223> OTHER INFORMATION: Description of Artificial Sequence: human
      full-length TyrRS in pET20B

<400> SEQUENCE: 2

Met Gly Asp Ala Pro Ser Pro Glu Glu Lys Leu His Leu Ile Thr Arg
1               5                   10                  15

Asn Leu Gln Glu Val Leu Gly Glu Glu Lys Leu Lys Glu Ile Leu Lys
            20                  25                  30

Glu Arg Glu Leu Lys Ile Tyr Trp Gly Thr Ala Thr Thr Gly Lys Pro
        35                  40                  45
```

```
His Val Ala Tyr Phe Val Pro Met Ser Lys Ile Ala Asp Phe Leu Lys
 50                  55                  60

Ala Gly Cys Glu Val Thr Ile Leu Phe Ala Asp Leu His Ala Tyr Leu
 65                  70                  75                  80

Asp Asn Met Lys Ala Pro Trp Glu Leu Leu Glu Leu Arg Val Ser Tyr
                 85                  90                  95

Tyr Glu Asn Val Ile Lys Ala Met Leu Glu Ser Ile Gly Val Pro Leu
                100                 105                 110

Glu Lys Leu Lys Phe Ile Lys Gly Thr Asp Tyr Gln Leu Ser Lys Glu
            115                 120                 125

Tyr Thr Leu Asp Val Tyr Arg Leu Ser Ser Val Val Thr Gln His Asp
            130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
            195                 200                 205

His Leu Met Asn Pro Met Val Pro Gly Leu Thr Gly Ser Lys Met Ser
            210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
                260                 265                 270

Ser Glu Phe Val Ile Leu Arg Asp Glu Lys Trp Gly Gly Asn Lys Thr
            275                 280                 285

Tyr Thr Ala Tyr Val Asp Leu Glu Lys Asp Phe Ala Ala Glu Val Val
            290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
                340                 345                 350

Gly Pro Ala Lys Asn Ser Glu Pro Glu Glu Val Ile Pro Ser Arg Leu
            355                 360                 365

Asp Ile Arg Val Gly Lys Ile Ile Thr Val Glu Lys His Pro Asp Ala
            370                 375                 380

Asp Ser Leu Tyr Val Glu Lys Ile Asp Val Gly Glu Ala Glu Pro Arg
385                 390                 395                 400

Thr Val Val Ser Gly Leu Val Gln Phe Val Pro Lys Glu Glu Leu Gln
                405                 410                 415

Asp Arg Leu Val Val Val Leu Cys Asn Leu Lys Pro Gln Lys Met Arg
            420                 425                 430

Gly Val Glu Ser Gln Gly Met Leu Leu Cys Ala Ser Ile Glu Gly Ile
            435                 440                 445

Asn Arg Gln Val Glu Pro Leu Asp Pro Pro Ala Gly Ser Ala Pro Gly
            450                 455                 460
```

```
Glu His Val Phe Val Lys Gly Tyr Glu Lys Gly Gln Pro Asp Glu Glu
465                 470                 475                 480

Leu Lys Pro Lys Lys Val Phe Glu Lys Leu Gln Ala Asp Phe Lys
            485                 490                 495

Ile Ser Glu Glu Cys Ile Ala Gln Trp Lys Gln Thr Asn Phe Met Thr
                500                 505                 510

Lys Leu Gly Ser Ile Ser Cys Lys Ser Leu Lys Gly Gly Asn Ile Ser
            515                 520                 525

Leu Glu His His His His His His
    530                 535

<210> SEQ ID NO 3
<211> LENGTH: 4682
<212> TYPE: DNA
<213> ORGANISM: Artificial Sequence
<220> FEATURE:
<221> NAME/KEY: CDS
<222> LOCATION: (3428)..(4543)
<220> FEATURE:
<223> OTHER INFORMATION: Description of Artificial Sequence: human mini
      TyrRS in pET20B

<400> SEQUENCE: 3
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tccctttagg      180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta aagggattt tgccgatttc ggcctattgg ttaaaaaatg agctgattta      420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg agacaataac cctgataaat gcttcaataa tattgaaaaa ggaagagtat     600
gagtattcaa catttccgtg tcgcccttat ccctttttt gcggcatttt gccttcctgt      660
ttttgctcac ccagaaacgc tggtgaaagt aaaagatgct gaagatcagt tgggtgcacg     720
agtgggttac atcgaactgg atctcaacag cggtaagatc cttgagagtt tcgccccga     780 agaacgtttt ccaatgatga gcacttttaa agttctgcta tgtggcgcgg tattatcccg     840
tattgacgcc gggcaagagc aactcggtcg ccgcatacac tattctcaga atgacttggt     900
tgagtactca ccagtcacag aaaagcatct tacggatggc atgacagtaa gagaattatg     960
cagtgctgcc ataaccatga gtgataacac tgcggccaac ttacttctga caacgatcgg    1020
aggaccgaag gagctaaccg cttttttgca acatggggg atcatgtaa ctcgccttga     1080 tcgttgggaa ccggagctga atgaagccat accaaacgac gagcgtgaca ccacgatgcc    1140
tgcagcaatg gcaacaacgt tgcgcaaact attaactggc gaactactta ctctagcttc    1200
ccggcaacaa ttaatagact ggatggaggc ggataaagtt gcaggaccac ttctgcgctc    1260
ggcccttccg gctggctggt ttattgctga taaatctgga gccggtgagc gtgggtctcg    1320
cggtatcatt gcagcactgg ggccagatgg taagccctcc cgtatcgtag ttatctacac    1380
gacggggagt caggcaacta tggatgaacg aaatagacag atcgctgaga taggtgcctc    1440
actgattaag cattggtaac tgtcagacca agtttactca tatatacttt agattgattt    1500
```

-continued

```
aaaacttcat tttaaattta aaaggatcta ggtgaagatc cttttttgata atctcatgac    1560 caaaatcccct taacgtgagt tttcgttcca ctgagcgtca gaccccgtag aaaagatcaa    1620
aggatcttct tgagatcctt ttttttctgcg cgtaatctgc tgcttgcaaa caaaaaaacc    1680
accgctacca gcggtggttt gtttgccgga tcaagagcta ccaactcttt ttccgaaggt    1740
aactggcttc agcagagcgc agataccaaa tactgtcctt ctagtgtagc cgtagttagg    1800
ccaccacttc aagaactctg tagcaccgcc tacataccctc gctctgctaa tcctgttacc    1860
agtggctgct gccagtggcg ataagtcgtg tcttaccggg ttggactcaa gacgatagtt    1920 accgataag gcgcagcggt cgggctgaac ggggggttcg tgcacacagc ccagcttgga    1980
gcgaacgacc tacaccgaac tgagatacct acagcgtgag ctatgagaaa gcgccacgct    2040
tcccgaaggg agaaaggcgg acaggtatcc ggtaagcggc agggtcggaa caggagagcg    2100
cacgagggag cttccagggg gaaacgcctg gtatctttat agtcctgtcg ggtttcgcca    2160
cctctgactt gagcgtcgat ttttgtgatg ctcgtcaggg gggcggagcc tatggaaaaa    2220
cgccagcaac gcggcctttt tacggttcct ggccttttgc tggcctttg ctcacatgtt    2280 ctttcctgcg ttatccccctg attctgtgga taaccgtatt accgcctttg agtgagctga    2340
taccgctcgc cgcagccgaa cgaccgagcg cagcgagtca gtgagcgagg aagcggaaga    2400
gcgcctgatg cggtatttc tccttacgca tctgtgcggt atttcacacc gcatatatgg    2460
tgcactctca gtacaatctg ctctgatgcc gcatagttaa gccagtatac actccgctat    2520
cgctacgtga ctgggtcatg gctgcgcccc gacacccgcc aacacccgct gacgcgccct    2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760
tgagtttctc cagaagcgtt aatgtctggc ttctgataaa gcgggccatg ttaagggcgg    2820
ttttttcctg tttggtcact gatgcctccg tgtaagggg atttctgttc atgggggtaa    2880
tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtgccca ggacccaacg ctgcccgaga tctcgatccc gcgaaattaa tacgactcac    3360
tatagggaga ccacaacggt ttccctctag aaataatttt gtttaacttt aagaaggaga    3420 tatacat atg ggg gac gct ccc agc cct gaa gag aaa ctg cac ctt atc      3469
        Met Gly Asp Ala Pro Ser Pro Glu Glu Lys Leu His Leu Ile
        1               5                   10 acc cgg aac ctg cag gag gtt ctg ggg gaa gag aag ctg aag gag ata      3517
Thr Arg Asn Leu Gln Glu Val Leu Gly Glu Glu Lys Leu Lys Glu Ile
15                  20                  25                  30 ctg aag gag cgg gaa ctt aaa att tac tgg gga acg gca acc acg ggc      3565
Leu Lys Glu Arg Glu Leu Lys Ile Tyr Trp Gly Thr Ala Thr Thr Gly
                35                  40                  45 aaa cca cat gtg gct tac ttt gtg ccc atg tca aag att gca gac ttc      3613
Lys Pro His Val Ala Tyr Phe Val Pro Met Ser Lys Ile Ala Asp Phe
            50                  55                  60
```

```
tta aag gca ggg tgt gag gta aca att ctg ttt gcg gac ctc cac gca      3661
Leu Lys Ala Gly Cys Glu Val Thr Ile Leu Phe Ala Asp Leu His Ala
        65                  70                  75 tac ctg gat aac atg aaa gcc cca tgg gaa ctt cta gaa ctc cga gtc      3709
Tyr Leu Asp Asn Met Lys Ala Pro Trp Glu Leu Leu Glu Leu Arg Val
        80                  85                  90 agt tac tat gag aat gtg atc aaa gca atg ctg gag agc att ggt gtg      3757
Ser Tyr Tyr Glu Asn Val Ile Lys Ala Met Leu Glu Ser Ile Gly Val
 95                 100                 105                 110 ccc ttg gag aag ctc aag ttc atc aaa ggc act gat tac cag ctc agc      3805
Pro Leu Glu Lys Leu Lys Phe Ile Lys Gly Thr Asp Tyr Gln Leu Ser
                115                 120                 125 aaa gag tac aca cta gat gtg tac aga ctc tcc tcc gtg gtc aca cag      3853
Lys Glu Tyr Thr Leu Asp Val Tyr Arg Leu Ser Ser Val Val Thr Gln
            130                 135                 140 cac gat tcc aag aag gct gga gct gag gtg gta aag cag gtg gag cac      3901
His Asp Ser Lys Lys Ala Gly Ala Glu Val Val Lys Gln Val Glu His
        145                 150                 155 cct ttg ctg agt ggc ctc tta tac ccc gga ctg cag gct ttg gat gaa      3949
Pro Leu Leu Ser Gly Leu Leu Tyr Pro Gly Leu Gln Ala Leu Asp Glu
160                 165                 170 gag tat tta aaa gta gat gcc caa ttt gga ggc att gat cag aga aag      3997
Glu Tyr Leu Lys Val Asp Ala Gln Phe Gly Gly Ile Asp Gln Arg Lys
175                 180                 185                 190 att ttc acc ttt gca gag aag tac ctc cct gca ctt ggc tat tca aaa      4045
Ile Phe Thr Phe Ala Glu Lys Tyr Leu Pro Ala Leu Gly Tyr Ser Lys
                195                 200                 205 cgg gtc cat ctg atg aat cct atg gtt cca gga tta aca ggc agc aaa      4093
Arg Val His Leu Met Asn Pro Met Val Pro Gly Leu Thr Gly Ser Lys
            210                 215                 220 atg agc tct tca gaa gag gag tcc aag att gat ctc ctt gat cgg aag      4141
Met Ser Ser Ser Glu Glu Glu Ser Lys Ile Asp Leu Leu Asp Arg Lys
        225                 230                 235 gag gat gtg aag aaa aaa ctg aag aag gcc ttc tgt gag cca gga aat      4189
Glu Asp Val Lys Lys Lys Leu Lys Lys Ala Phe Cys Glu Pro Gly Asn
    240                 245                 250 gtg gag aac aat ggg gtt ctg tcc ttc atc aag cat gtc ctt ttt ccc      4237
Val Glu Asn Asn Gly Val Leu Ser Phe Ile Lys His Val Leu Phe Pro
255                 260                 265                 270 ctt aag tcc gag ttt gtg atc cta cga gat gag aaa tgg ggt gga aac      4285
Leu Lys Ser Glu Phe Val Ile Leu Arg Asp Glu Lys Trp Gly Gly Asn
                275                 280                 285 aaa acc tac aca gct tac gtg gac ctg gaa aag gac ttt gct gct gag      4333
Lys Thr Tyr Thr Ala Tyr Val Asp Leu Glu Lys Asp Phe Ala Ala Glu
            290                 295                 300 gtt gta cat cct gga gac ctg aag aat tct gtt gaa gtc gca ctg aac      4381
Val Val His Pro Gly Asp Leu Lys Asn Ser Val Glu Val Ala Leu Asn
        305                 310                 315 aag ttg ctg gat cca atc cgg gaa aag ttt aat acc cct gcc ctg aaa      4429
Lys Leu Leu Asp Pro Ile Arg Glu Lys Phe Asn Thr Pro Ala Leu Lys
    320                 325                 330 aaa ctg gcc agc gct gcc tac cca gat ccc tca aag cag aag cca atg      4477
Lys Leu Ala Ser Ala Ala Tyr Pro Asp Pro Ser Lys Gln Lys Pro Met
335                 340                 345                 350 gcc aaa ggc cct gcc aag aat tca gaa cca gag gag gtc atc ctc gag      4525
Ala Lys Gly Pro Ala Lys Asn Ser Glu Pro Glu Glu Val Ile Leu Glu
                355                 360                 365 cac cac cac cac cac cac tgagatccgg ctgctaacaa agcccgaaag             4573
His His His His His His
```

-continued

```
                                              370
gaagctgagt tggctgctgc caccgctgag caataactag cataaccct  tggggcctct    4633 aaacgggtct tgaggggttt tttgctgaaa ggaggaacta tatccggat                4682
```

<210> SEQ ID NO 4
<211> LENGTH: 372
<212> TYPE: PRT
<213> ORGANISM: Artificial Sequence
<220> FEATURE:
<223> OTHER INFORMATION: Description of Artificial Sequence: human mini
      TyrRS in pET20B

<400> SEQUENCE: 4

```
Met Gly Asp Ala Pro Ser Pro Glu Glu Lys Leu His Leu Ile Thr Arg
  1               5                  10                  15

Asn Leu Gln Glu Val Leu Gly Glu Glu Lys Leu Lys Glu Ile Leu Lys
                 20                  25                  30

Glu Arg Glu Leu Lys Ile Tyr Trp Gly Thr Ala Thr Thr Gly Lys Pro
             35                  40                  45

His Val Ala Tyr Phe Val Pro Met Ser Lys Ile Ala Asp Phe Leu Lys
         50                  55                  60

Ala Gly Cys Glu Val Thr Ile Leu Phe Ala Asp Leu His Ala Tyr Leu
 65                  70                  75                  80

Asp Asn Met Lys Ala Pro Trp Glu Leu Leu Glu Leu Arg Val Ser Tyr
                 85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Val Thr Gln His Asp
    130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
        195                 200                 205

His Leu Met Asn Pro Met Val Pro Gly Leu Thr Gly Ser Lys Met Ser
    210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
        275                 280                 285

Tyr Thr Ala Tyr Val Asp Leu Glu Lys Asp Phe Ala Ala Glu Val Val
    290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335
```

```
Ala Ser Ala Ala Tyr Pro Asp Pro Ser Lys Gln Lys Pro Met Ala Lys
        340                 345                 350

Gly Pro Ala Lys Asn Ser Glu Pro Glu Glu Val Ile Leu Glu His His
        355                 360                 365

His His His His
    370

<210> SEQ ID NO 5
<211> LENGTH: 4100
<212> TYPE: DNA
<213> ORGANISM: Artificial Sequence
<220> FEATURE:
<221> NAME/KEY: CDS
<222> LOCATION: (3428)..(3961)
<220> FEATURE:
<223> OTHER INFORMATION: Description of Artificial Sequence:  human
      TyrRS carboxyl-terminal domain in pET20B

<400> SEQUENCE: 5
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tccctttagg      180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggatttt gccgatttc ggcctattgg ttaaaaatg agctgattta        420 acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg agacaataac cctgataaat gcttcaataa tattgaaaaa ggaagagtat     600
gagtattcaa catttccgtg tcgcccttat ccctttttt gcggcatttt gccttcctgt      660
ttttgctcac ccagaaacgc tggtgaaagt aaaagatgct gaagatcagt tgggtgcacg     720
agtgggttac atcgaactgg atctcaacag cggtaagatc cttgagagtt ttcgccccga     780
agaacgtttt ccaatgatga gcacttttaa agttctgcta tgtggcgcgg tattatcccg     840
tattgacgcc gggcaagagc aactcggtcg ccgcatacac tattctcaga atgacttggt     900
tgagtactca ccagtcacag aaaagcatct tacggatggc atgacagtaa gagaattatg     960
cagtgctgcc ataaccatga gtgataacac tgcggccaac ttacttctga caacgatcgg    1020
aggaccgaag gagctaaccg cttttttgca acatggggg gatcatgtaa ctcgccttga    1080
tcgttgggaa ccggagctga atgaagccat accaaacgac gagcgtgaca ccacgatgcc    1140
tgcagcaatg gcaacaacgt tgcgcaaact attaactggc gaactactta ctctagcttc    1200
ccggcaacaa ttaatagact ggatggaggc ggataaagtt gcaggaccac ttctgcgctc    1260
ggcccttccg gctggctggt ttattgctga taaatctgga gccggtgagc gtgggtctcg    1320
cggtatcatt gcagcactgg ggccagatgg taagccctcc cgtatcgtag ttatctacac    1380
gacggggagt caggcaacta tggatgaacg aaatagacag atcgctgaga taggtgcctc    1440
actgattaag cattggtaac tgtcagacca agtttactca tatatacttt agattgattt    1500
aaaacttcat ttttaattta aaaggatcta ggtgaagatc ctttttgata atctcatgac    1560
caaaatccct taacgtgagt tttcgttcca ctgagcgtca gaccccgtag aaaagatcaa    1620
aggatcttct tgagatcctt ttttctgcg cgtaatctgc tgcttgcaaa caaaaaaacc    1680
```

-continued

```
accgctacca gcggtggttt gtttgccgga tcaagagcta ccaactctt ttccgaaggt      1740 aactggcttc agcagagcgc agataccaaa tactgtcctt ctagtgtagc cgtagttagg      1800
ccaccacttc aagaactctg tagcaccgcc tacatacctc gctctgctaa tcctgttacc      1860
agtggctgct gccagtggcg ataagtcgtg tcttaccggg ttggactcaa gacgatagtt      1920 accgataag gcgcagcggt cgggctgaac ggggggttcg tgcacacagc ccagcttgga      1980
gcgaacgacc tacaccgaac tgagatacct acagcgtgag ctatgagaaa gcgccacgct      2040
tcccgaaggg agaaaggcgg acaggtatcc ggtaagcggc agggtcggaa caggagagcg      2100
cacgagggag cttccagggg gaaacgcctg gtatctttat agtcctgtcg ggtttcgcca      2160
cctctgactt gagcgtcgat ttttgtgatg ctcgtcaggg gggcggagcc tatggaaaaa      2220
cgccagcaac gcggccttt tacggttcct ggccttttgc tggccttttg ctcacatgtt      2280
ctttcctgcg ttatccctg attctgtgga taaccgtatt accgcctttg agtgagctga      2340
taccgctcgc cgcagccgaa cgaccgagcg cagcgagtca gtgagcgagg aagcggaaga      2400
gcgcctgatg cggtattttc tccttacgca tctgtgcggt atttcacacc gcatatatgg      2460
tgcactctca gtacaatctg ctctgatgcc gcatagttaa gccagtatac actccgctat      2520
cgctacgtga ctgggtcatg gctgcgcccc gacacccgcc aacacccgct gacgcgccct      2580
gacgggcttg tctgctcccg gcatccgctt acagacaagc tgtgaccgtc tccgggagct      2640
gcatgtgtca gaggttttca ccgtcatcac cgaaacgcgc gaggcagctg cggtaaagct      2700
catcagcgtg gtcgtgaagc gattcacaga tgtctgcctg ttcatccgcg tccagctcgt      2760
tgagtttctc cagaagcgtt aatgtctggc ttctgataaa gcgggccatg ttaagggcgg      2820
ttttttcctg tttggtcact gatgcctccg tgtaagggg atttctgttc atggggtaa      2880 tgataccgat gaaacgagag aggatgctca cgatacgggt tactgatgat gaacatgccc      2940
ggttactgga acgttgtgag ggtaaacaac tggcggtatg gatgcggcgg gaccagagaa      3000
aaatcactca gggtcaatgc cagcgcttcg ttaatacaga tgtaggtgtt ccacagggta      3060
gccagcagca tcctgcgatg cagatccgga acataatggt gcagggcgct gacttccgcg      3120
tttccagact ttacgaaaca cggaaaccga agaccattca tgttgttgct caggtcgcag      3180
acgttttgca gcagcagtcg cttcacgttc gctcgcgtat cggtgattca ttctgctaac      3240
cagtaaggca accccgccag cctagccggg tcctcaacga caggagcacg atcatgcgca      3300
cccgtggcca ggacccaacg ctgcccgaga tctcgatccc gcgaaattaa tacgactcac      3360
tatagggaga ccacaacggt ttccctctag aaataatttt gtttaacttt aagaaggaga      3420 tatacat atg cca gag gag gtc atc cca tcc cgg ctg gat atc cgt gtg      3469
        Met Pro Glu Glu Val Ile Pro Ser Arg Leu Asp Ile Arg Val
          1               5                  10 ggg aaa atc atc act gtg gag aag cac cca gat gca gac agc ctg tat      3517
Gly Lys Ile Ile Thr Val Glu Lys His Pro Asp Ala Asp Ser Leu Tyr
 15                  20                  25                  30 gta gag aag att gac gtg ggg gaa gct gaa cca cgg act gtg gtg agc      3565
Val Glu Lys Ile Asp Val Gly Glu Ala Glu Pro Arg Thr Val Val Ser
                 35                  40                  45 ggc ctg gta cag ttc gtg ccc aag gag gaa ctg cag gac agg ctg gta      3613
Gly Leu Val Gln Phe Val Pro Lys Glu Glu Leu Gln Asp Arg Leu Val
             50                  55                  60 gtg gtg ctg tgc aac ctg aaa ccc cag aag atg aga gga gtc gag tcc      3661
Val Val Leu Cys Asn Leu Lys Pro Gln Lys Met Arg Gly Val Glu Ser
 65                  70                  75
```

```
caa ggc atg ctt ctg tgt gct tct ata gaa ggg ata aac cgc cag gtt    3709
Gln Gly Met Leu Leu Cys Ala Ser Ile Glu Gly Ile Asn Arg Gln Val
     80                  85                  90 gaa cct ctg gac cct ccg gca ggc tct gct cct ggt gag cac gtg ttt    3757
Glu Pro Leu Asp Pro Pro Ala Gly Ser Ala Pro Gly Glu His Val Phe
 95                 100                 105                 110 gtg aag ggc tat gaa aag ggc caa cca gat gag gag ctc aag ccc aag    3805
Val Lys Gly Tyr Glu Lys Gly Gln Pro Asp Glu Glu Leu Lys Pro Lys
                115                 120                 125 aag aaa gtc ttc gag aag ttg cag gct gac ttc aaa att tct gag gag    3853
Lys Lys Val Phe Glu Lys Leu Gln Ala Asp Phe Lys Ile Ser Glu Glu
            130                 135                 140 tgc atc gca cag tgg aag caa acc aac ttc atg acc aag ctg ggc tcc    3901
Cys Ile Ala Gln Trp Lys Gln Thr Asn Phe Met Thr Lys Leu Gly Ser
145                 150                 155 att tcc tgt aaa tcg ctg aaa ggg ggg aac att agc ctc gag cac cac    3949
Ile Ser Cys Lys Ser Leu Lys Gly Gly Asn Ile Ser Leu Glu His His
    160                 165                 170 cac cac cac cac tgagatccgg ctgctaacaa agcccgaaag gaagctgagt        4001
His His His His
175 tggctgctgc caccgctgag caataactag cataacccct tgggcctct  aaacgggtct  4061 tgagggtttt tttgctgaaa ggaggaacta tatccggat                         4100

<210> SEQ ID NO 6
<211> LENGTH: 178
<212> TYPE: PRT
<213> ORGANISM: Artificial Sequence
<220> FEATURE:
<223> OTHER INFORMATION: Description of Artificial Sequence:  human TyrRS
      carboxyl-terminal domain in pET20B

<400> SEQUENCE: 6

Met Pro Glu Glu Val Ile Pro Ser Arg Leu Asp Ile Arg Val Gly Lys
 1               5                  10                  15

Ile Ile Thr Val Glu Lys His Pro Asp Ala Asp Ser Leu Tyr Val Glu
                20                  25                  30

Lys Ile Asp Val Gly Glu Ala Glu Pro Arg Thr Val Val Ser Gly Leu
            35                  40                  45

Val Gln Phe Val Pro Lys Glu Glu Leu Gln Asp Arg Leu Val Val Val
        50                  55                  60

Leu Cys Asn Leu Lys Pro Gln Lys Met Arg Gly Val Glu Ser Gln Gly
 65                 70                  75                  80

Met Leu Leu Cys Ala Ser Ile Glu Gly Ile Asn Arg Gln Val Glu Pro
                85                  90                  95

Leu Asp Pro Pro Ala Gly Ser Ala Pro Gly Glu His Val Phe Val Lys
            100                 105                 110

Gly Tyr Glu Lys Gly Gln Pro Asp Glu Glu Leu Lys Pro Lys Lys Lys
        115                 120                 125

Val Phe Glu Lys Leu Gln Ala Asp Phe Lys Ile Ser Glu Glu Cys Ile
    130                 135                 140

Ala Gln Trp Lys Gln Thr Asn Phe Met Thr Lys Leu Gly Ser Ile Ser
145                 150                 155                 160

Cys Lys Ser Leu Lys Gly Gly Asn Ile Ser Leu Glu His His His
                165                 170                 175

His His
```

<210> SEQ ID NO 7
<211> LENGTH: 4682
<212> TYPE: DNA
<213> ORGANISM: Artificial Sequence
<220> FEATURE:
<221> NAME/KEY: CDS
<222> LOCATION: (3428)..(4543)
<220> FEATURE:
<223> OTHER INFORMATION: Description of Artificial Sequence: human mini TyrRS mutant in pET20B

<400> SEQUENCE: 7

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta tagggatttt gccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg agacaataac cctgataaat gcttcaataa tattgaaaaa ggaagagtat     600
gagtattcaa catttccgtg tcgcccttat tccctttttt gcggcatttt gccttcctgt     660
ttttgctcac ccagaaacgc tggtgaaagt aaaagatgct gaagatcagt tgggtgcacg     720
agtgggttac atcgaactgg atctcaacag cggtaagatc cttgagagtt ttcgccccga     780
agaacgtttt ccaatgatga gcacttttaa agttctgcta tgtggcgcgg tattatcccg     840
tattgacgcc gggcaagagc aactcggtcg ccgcatacac tattctcaga atgacttggt     900
tgagtactca ccagtcacag aaaagcatct tacggatggc atgacagtaa gagaattatg     960
cagtgctgcc ataaccatga gtgataacac tgcggccaac ttacttctga caacgatcgg    1020
aggaccgaag gagctaaccg cttttttgca acatggggg gatcatgtaa ctcgccttga    1080
tcgttgggaa ccggagctga tgaagccat accaaacgac gagcgtgaca ccacgatgcc    1140
tgcagcaatg gcaacaacgt tgcgcaaact attaactggc gaactactta ctctagcttc    1200
ccggcaacaa ttaatagact ggatggaggc ggataaagtt gcaggaccac ttctgcgctc    1260
ggcccttccg gctggctggt ttattgctga taaatctgga gccggtgagc gtgggtctcg    1320
cggtatcatt gcagcactgg ggccagatgg taagccctcc cgtatcgtag ttatctacac    1380
gacggggagt caggcaacta tggatgaacg aaatagacag atcgctgaga taggtgcctc    1440
actgattaag cattggtaac tgtcagacca agtttactca tatatacttt agattgattt    1500
aaaacttcat ttttaattta aaaggatcta ggtgaagatc ctttttgata atctcatgac    1560
caaaatccct taacgtgagt tttcgttcca ctgagcgtca gaccccgtag aaaagatcaa    1620
aggatcttct tgagatcctt ttttctgcgc gtaatctgc tgcttgcaaa caaaaaaacc    1680
accgctacca gcggtggttt gtttgccgga tcaagagcta ccaactcttt tccgaaggt    1740
aactggcttc agcagagcgc agataccaaa tactgtcctt ctagtgtagc cgtagttagg    1800
ccaccacttc aagaactctg tagcaccgcc tacatacctc gctctgctaa tcctgttacc    1860
agtggctgct gccagtggcg ataagtcgtg tcttaccggg ttggactcaa gacgatagtt    1920
accggataag gcgcagcggt cgggctgaac ggggggttcg tgcacacagc ccagcttgga    1980
```

```
gcgaacgacc tacaccgaac tgagatacct acagcgtgag ctatgagaaa gcgccacgct    2040
tcccgaaggg agaaaggcgg acaggtatcc ggtaagcggc agggtcggaa caggagagcg    2100
cacgagggag cttccagggg gaaacgcctg gtatctttat agtcctgtcg ggtttcgcca    2160
cctctgactt gagcgtcgat ttttgtgatg ctcgtcaggg gggcggagcc tatggaaaaa    2220
cgccagcaac gcggccttt tacggttcct ggccttttgc tggccttttg ctcacatgtt    2280
ctttcctgcg ttatcccctg attctgtgga taaccgtatt accgcctttg agtgagctga    2340
taccgctcgc cgcagccgaa cgaccgagcg cagcgagtca gtgagcgagg aagcggaaga    2400
gcgcctgatg cggtattttc tccttacgca tctgtgcggt atttcacacc gcatatatgg    2460
tgcactctca gtacaatctg ctctgatgcc gcatagttaa gccagtatac actccgctat    2520
cgctacgtga ctgggtcatg gctgcgcccc gacacccgcc aacacccgct gacgcgccct    2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760
tgagtttctc cagaagcgtt aatgtctggc ttctgataaa gcgggccatg ttaagggcgg    2820
ttttttcctg tttggtcact gatgcctccg tgtaagggg atttctgttc atgggggtaa    2880
tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggcca ggacccaacg ctgcccgaga tctcgatccc gcgaaattaa tacgactcac    3360
tatagggaga ccacaacggt ttccctctag aaataatttt gtttaacttt aagaaggaga    3420 tatacat atg ggg gac gct ccc agc cct gaa gag aaa ctg cac ctt atc      3469
        Met Gly Asp Ala Pro Ser Pro Glu Glu Lys Leu His Leu Ile
         1               5                  10 acc cgg aac ctg cag gag gtt ctg ggg gaa gag aag ctg aag gag ata      3517
Thr Arg Asn Leu Gln Glu Val Leu Gly Glu Glu Lys Leu Lys Glu Ile
 15              20                  25                  30 ctg aag gag cgg gaa ctt aaa att tac tgg gga acg gca acc acg ggc      3565
Leu Lys Glu Arg Glu Leu Lys Ile Tyr Trp Gly Thr Ala Thr Thr Gly
             35                  40                  45 aaa cca cat gtg gct tac ttt gtg ccc atg tca aag att gca gac ttc      3613
Lys Pro His Val Ala Tyr Phe Val Pro Met Ser Lys Ile Ala Asp Phe
         50                  55                  60 tta aag gca ggg tgt gag gta aca att ctg ttt gcg gac ctc cac gca      3661
Leu Lys Ala Gly Cys Glu Val Thr Ile Leu Phe Ala Asp Leu His Ala
 65                  70                  75 tac ctg gat aac atg aaa gcc cca tgg gaa ctt cta gaa ctg cag gtc      3709
Tyr Leu Asp Asn Met Lys Ala Pro Trp Glu Leu Leu Glu Leu Gln Val
 80                  85                  90 agt tac tat gag aat gtg atc aaa gca atg ctg gag agc att ggt gtg      3757
Ser Tyr Tyr Glu Asn Val Ile Lys Ala Met Leu Glu Ser Ile Gly Val
 95                 100                 105                 110 ccc ttg gag aag ctc aag ttc atc aaa ggc act gat tac cag ctc agc      3805
Pro Leu Glu Lys Leu Lys Phe Ile Lys Gly Thr Asp Tyr Gln Leu Ser
             115                 120                 125
```

```
aaa gag tac aca cta gat gtg tac aga ctc tcc tcc gtg gtc aca cag       3853
Lys Glu Tyr Thr Leu Asp Val Tyr Arg Leu Ser Ser Val Val Thr Gln
        130                 135                 140 cac gat tcc aag aag gct gga gct gag gtg gta aag cag gtg gag cac       3901
His Asp Ser Lys Lys Ala Gly Ala Glu Val Val Lys Gln Val Glu His
            145                 150                 155 cct ttg ctg agt ggc ctc tta tac ccc gga ctg cag gct ttg gat gaa       3949
Pro Leu Leu Ser Gly Leu Leu Tyr Pro Gly Leu Gln Ala Leu Asp Glu
        160                 165                 170 gag tat tta aaa gta gat gcc caa ttt gga ggc att gat cag aga aag       3997
Glu Tyr Leu Lys Val Asp Ala Gln Phe Gly Gly Ile Asp Gln Arg Lys
175                 180                 185                 190 att ttc acc ttt gca gag aag tac ctc cct gca ctt ggc tat tca aaa       4045
Ile Phe Thr Phe Ala Glu Lys Tyr Leu Pro Ala Leu Gly Tyr Ser Lys
                195                 200                 205 cgg gtc cat ctg atg aat cct atg gtt cca gga tta aca ggc agc aaa       4093
Arg Val His Leu Met Asn Pro Met Val Pro Gly Leu Thr Gly Ser Lys
            210                 215                 220 atg agc tct tca gaa gag gag tcc aag att gat ctc ctt gat cgg aag       4141
Met Ser Ser Ser Glu Glu Glu Ser Lys Ile Asp Leu Leu Asp Arg Lys
        225                 230                 235 gag gat gtg aag aaa aaa ctg aag aag gcc ttc tgt gag cca gga aat       4189
Glu Asp Val Lys Lys Lys Leu Lys Lys Ala Phe Cys Glu Pro Gly Asn
240                 245                 250 gtg gag aac aat ggg gtt ctg tcc ttc atc aag cat gtc ctt ttt ccc       4237
Val Glu Asn Asn Gly Val Leu Ser Phe Ile Lys His Val Leu Phe Pro
255                 260                 265                 270 ctt aag tcc gag ttt gtg atc cta cga gat gag aaa tgg ggt gga aac       4285
Leu Lys Ser Glu Phe Val Ile Leu Arg Asp Glu Lys Trp Gly Gly Asn
                275                 280                 285 aaa acc tac aca gct tac gtg gac ctg gaa aag gac ttt gct gct gag       4333
Lys Thr Tyr Thr Ala Tyr Val Asp Leu Glu Lys Asp Phe Ala Ala Glu
            290                 295                 300 gtt gta cat cct gga gac ctg aag aat tct gtt gaa gtc gca ctg aac       4381
Val Val His Pro Gly Asp Leu Lys Asn Ser Val Glu Val Ala Leu Asn
        305                 310                 315 aag ttg ctg gat cca atc cgg gaa aag ttt aat acc cct gcc ctg aaa       4429
Lys Leu Leu Asp Pro Ile Arg Glu Lys Phe Asn Thr Pro Ala Leu Lys
    320                 325                 330 aaa ctg gcc agc gct gcc tac cca gat ccc tca aag cag aag cca atg       4477
Lys Leu Ala Ser Ala Ala Tyr Pro Asp Pro Ser Lys Gln Lys Pro Met
335                 340                 345                 350 gcc aaa ggc cct gcc aag aat tca gaa cca gag gag gtc atc ctc gag       4525
Ala Lys Gly Pro Ala Lys Asn Ser Glu Pro Glu Glu Val Ile Leu Glu
                355                 360                 365 cac cac cac cac cac cac tgagatccgg ctgctaacaa agcccgaaag             4573
His His His His His His
            370 gaagctgagt tggctgctgc caccgctgag caataactag cataacccct tggggcctct    4633 aaacgggtct tgagggggttt tttgctgaaa ggaggaacta tatccggat               4682

<210> SEQ ID NO 8
<211> LENGTH: 372
<212> TYPE: PRT
<213> ORGANISM: Artificial Sequence
<220> FEATURE:
<223> OTHER INFORMATION: Description of Artificial Sequence: human mini
      TyrRS mutant in pET20B

<400> SEQUENCE: 8
```

```
Met Gly Asp Ala Pro Ser Pro Glu Glu Lys Leu His Leu Ile Thr Arg
 1               5                  10                  15

Asn Leu Gln Glu Val Leu Gly Glu Lys Leu Lys Glu Ile Leu Lys
             20                  25                  30

Glu Arg Glu Leu Lys Ile Tyr Trp Gly Thr Ala Thr Gly Lys Pro
             35                  40                  45

His Val Ala Tyr Phe Val Pro Met Ser Lys Ile Ala Asp Phe Leu Lys
 50                  55                  60

Ala Gly Cys Glu Val Thr Ile Leu Phe Ala Asp Leu His Ala Tyr Leu
 65                  70                  75                  80

Asp Asn Met Lys Ala Pro Trp Glu Leu Leu Glu Leu Gln Val Ser Tyr
             85                  90                  95

Tyr Glu Asn Val Ile Lys Ala Met Leu Glu Ser Ile Gly Val Pro Leu
             100                 105                 110

Glu Lys Leu Lys Phe Ile Lys Gly Thr Asp Tyr Gln Leu Ser Lys Glu
             115                 120                 125

Tyr Thr Leu Asp Val Tyr Arg Leu Ser Ser Val Val Thr Gln His Asp
             130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                 165                 170                 175

Leu Lys Val Asp Ala Gln Phe Gly Gly Ile Asp Gln Arg Lys Ile Phe
             180                 185                 190

Thr Phe Ala Glu Lys Tyr Leu Pro Ala Leu Gly Tyr Ser Lys Arg Val
             195                 200                 205

His Leu Met Asn Pro Met Val Pro Gly Leu Thr Gly Ser Lys Met Ser
             210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                 245                 250                 255

Asn Asn Gly Val Leu Ser Phe Ile Lys His Val Leu Phe Pro Leu Lys
             260                 265                 270

Ser Glu Phe Val Ile Leu Arg Asp Glu Lys Trp Gly Gly Asn Lys Thr
             275                 280                 285

Tyr Thr Ala Tyr Val Asp Leu Glu Lys Asp Phe Ala Ala Glu Val Val
             290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
             325                 330                 335

Ala Ser Ala Ala Tyr Pro Asp Pro Ser Lys Gln Lys Pro Met Ala Lys
             340                 345                 350

Gly Pro Ala Lys Asn Ser Glu Pro Glu Glu Val Ile Leu Glu His His
             355                 360                 365

His His His His
        370
```

<210> SEQ ID NO 9
<211> LENGTH: 5018
<212> TYPE: DNA
<213> ORGANISM: Artificial Sequence
<220> FEATURE:

<221> NAME/KEY: CDS
<222> LOCATION: (3428)..(4879)
<220> FEATURE:
<223> OTHER INFORMATION: Description of Artificial Sequence: human full-length TrpRS in pET20B

<400> SEQUENCE: 9

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tcccttagg      180
gttccgattt agtgctttac ggcacctcga ccccaaaaaa cttgattagg gtgatggttc     240
acgtagtggg ccatcgccct gatagacggt ttttcgccct tgacgttgg agtccacgtt     300
ctttaatagt ggactcttgt tccaaactgg aacaacactc aaccctatct cggtctattc     360
ttttgattta tagggatttt tgccgatttc ggcctattgg ttaaaaatg agctgattta     420
acaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg agacaataac cctgataaat gcttcaataa tattgaaaaa ggaagagtat     600
gagtattcaa catttccgtg tcgcccttat ccctttttt gcggcatttt gccttcctgt     660
ttttgctcac ccagaaacgc tggtgaaagt aaaagatgct gaagatcagt tgggtgcacg     720
agtgggttac atcgaactgg atctcaacag cggtaagatc cttgagagtt ttcgccccga     780
agaacgtttt ccaatgatga gcacttttaa agttctgcta tgtggcgcgg tattatcccg     840
tattgacgcc gggcaagagc aactcggtcg ccgcatacac tattctcaga atgacttggt     900
tgagtactca ccagtcacag aaaagcatct tacggatggc atgacagtaa gagaattatg     960
cagtgctgcc ataaccatga gtgataacac tgcggccaac ttacttctga caacgatcgg    1020
aggaccgaag gagctaaccg cttttttgca acatggggg atcatgtaa ctcgccttga    1080
tcgttgggaa ccggagctga atgaagccat accaaacgac gagcgtgaca ccacgatgcc    1140
tgcagcaatg gcaacaacgt tgcgcaaact attaactggc gaactactta ctctagcttc    1200
ccggcaacaa ttaatagact ggatggaggc ggataaagtt gcaggaccac ttctgcgctc    1260
ggcccttccg gctggctggt ttattgctga taaatctgga gccggtgagc gtgggtctcg    1320
cggtatcatt gcagcactgg ggccagatgg taagccctcc cgtatcgtag ttatctacac    1380
gacgggagt caggcaacta tggatgaacg aaatagacag atcgctgaga taggtgcctc    1440
actgattaag cattggtaac tgtcagacca agtttactca tatatacttt agattgattt    1500
aaaacttcat ttttaattta aaaggatcta ggtgaagatc ctttttgata atctcatgac    1560
caaaatccct taacgtgagt tttcgttcca ctgagcgtca gacccccgtag aaaagatcaa    1620
aggatcttct tgagatcctt ttttctgcg cgtaatctgc tgcttgcaaa caaaaaaacc    1680
accgctacca gcggtggttt gtttgccgga tcaagagcta ccaactcttt ttccgaaggt    1740
aactggcttc agcagagcgc agataccaaa tactgtcctt ctagtgtagc cgtagttagg    1800
ccaccacttc aagaactctg tagcaccgcc tacatacctc gctctgctaa tcctgttacc    1860
agtggctgct gccagtggcg ataagtcgtg tcttaccggg ttggactcaa gacgatagtt    1920
accggataag gcgcagcggt cgggctgaac ggggggttcg tgcacacagc ccagcttgga    1980
gcgaacgacc tacaccgaac tgagatacct acagcgtgag ctatgagaaa gcgccacgct    2040
tcccgaaggg agaaaggcgg acaggtatcc ggtaagcggc agggtcggaa caggagagcg    2100
cacgagggag cttccagggg gaaacgcctg gtatctttat agtcctgtcg ggtttcgcca    2160
```

-continued

```
cctctgactt gagcgtcgat ttttgtgatg ctcgtcaggg gggcggagcc tatggaaaaa    2220
cgccagcaac gcggccttt  tacggttcct ggccttttgc tggccttttg ctcacatgtt    2280
ctttcctgcg ttatcccctg attctgtgga taaccgtatt accgcctttg agtgagctga    2340
taccgctcgc cgcagccgaa cgaccgagcg cagcgagtca gtgagcgagg aagcggaaga    2400
gcgcctgatg cggtattttc tccttacgca tctgtgcggt atttcacacc gcatatatgg    2460
tgcactctca gtacaatctg ctctgatgcc gcatagttaa gccagtatac actccgctat    2520
cgctacgtga ctgggtcatg gctgcgcccc gacacccgcc aacacccgct gacgcgccct    2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760
tgagtttctc cagaagcgtt aatgtctggc ttctgataaa gcgggccatg ttaagggcgg    2820
ttttttcctg tttggtcact gatgcctccg tgtaaggggg atttctgttc atgggggtaa    2880
tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggcca ggacccaacg ctgcccgaga tctcgatccc gcgaaattaa tacgactcac    3360
tatagggaga ccacaacggt ttccctctag aaataatttt gtttaacttt aagaaggaga    3420
tatacat atg ccc aac agt gag ccc gca tct ctg ctg gag ctg ttc aac      3469
        Met Pro Asn Ser Glu Pro Ala Ser Leu Leu Glu Leu Phe Asn
        1               5                   10
agc atc gcc aca caa ggg gag ctc gta agg tcc ctc aaa gcg gga aat      3517
Ser Ile Ala Thr Gln Gly Glu Leu Val Arg Ser Leu Lys Ala Gly Asn
15              20                  25                  30
gcg tca aag gat gaa att gat tct gca gta aag atg ttg gtg tca tta      3565
Ala Ser Lys Asp Glu Ile Asp Ser Ala Val Lys Met Leu Val Ser Leu
                35                  40                  45
aaa atg agc tac aaa gct gcc gcg ggg gag gat tac aag gct gac tgt      3613
Lys Met Ser Tyr Lys Ala Ala Ala Gly Glu Asp Tyr Lys Ala Asp Cys
            50                  55                  60
cct cca ggg aac cca gca cct acc agt aat cat ggc cca gat gcc aca      3661
Pro Pro Gly Asn Pro Ala Pro Thr Ser Asn His Gly Pro Asp Ala Thr
65                  70                  75
gaa gct gaa gag gat ttt gtg gac cca tgg aca gta cag aca agc agt      3709
Glu Ala Glu Glu Asp Phe Val Asp Pro Trp Thr Val Gln Thr Ser Ser
        80                  85                  90
gca aaa ggc ata gac tac gat aag ctc att gtt cgg ttt gga agt agt      3757
Ala Lys Gly Ile Asp Tyr Asp Lys Leu Ile Val Arg Phe Gly Ser Ser
95                  100                 105                 110
aaa att gac aaa gag cta ata aac cga ata gag aga gcc acc ggc caa      3805
Lys Ile Asp Lys Glu Leu Ile Asn Arg Ile Glu Arg Ala Thr Gly Gln
                115                 120                 125
aga cca cac cac ttc ctg cgc aga ggc atc ttc ttc tca cac aga gat      3853
Arg Pro His His Phe Leu Arg Arg Gly Ile Phe Phe Ser His Arg Asp
            130                 135                 140
```

```
atg aat cag gtt ctt gat gcc tat gaa aat aag aag cca ttt tat ctg    3901
Met Asn Gln Val Leu Asp Ala Tyr Glu Asn Lys Lys Pro Phe Tyr Leu
        145                 150                 155 tac acg ggc cgg ggc ccc tct tct gaa gca atg cat gta ggt cac ctc    3949
Tyr Thr Gly Arg Gly Pro Ser Ser Glu Ala Met His Val Gly His Leu
    160                 165                 170 att cca ttt att ttc aca aag tgg ctc cag gat gta ttt aac gtg ccc    3997
Ile Pro Phe Ile Phe Thr Lys Trp Leu Gln Asp Val Phe Asn Val Pro
175                 180                 185                 190 ttg gtc atc cag atg acg gat gac gag aag tat ctg tgg aag gac ctg    4045
Leu Val Ile Gln Met Thr Asp Asp Glu Lys Tyr Leu Trp Lys Asp Leu
                195                 200                 205 acc ctg gac cag gcc tat ggc gat gct gtt gag aat gcc aag gac atc    4093
Thr Leu Asp Gln Ala Tyr Gly Asp Ala Val Glu Asn Ala Lys Asp Ile
            210                 215                 220 atc gcc tgt ggc ttt gac atc aac aag act ttc ata ttc tct gac ctg    4141
Ile Ala Cys Gly Phe Asp Ile Asn Lys Thr Phe Ile Phe Ser Asp Leu
        225                 230                 235 gac tac atg ggg atg agc tca ggt ttc tac aaa aat gtg gtg aag att    4189
Asp Tyr Met Gly Met Ser Ser Gly Phe Tyr Lys Asn Val Val Lys Ile
    240                 245                 250 caa aag cat gtt acc ttc aac caa gtg aaa ggc att ttc ggc ttc act    4237
Gln Lys His Val Thr Phe Asn Gln Val Lys Gly Ile Phe Gly Phe Thr
255                 260                 265                 270 gac agc gac tgc att ggg aag atc agt ttt cct gcc atc cag gct gct    4285
Asp Ser Asp Cys Ile Gly Lys Ile Ser Phe Pro Ala Ile Gln Ala Ala
                275                 280                 285 ccc tcc ttc agc aac tca ttc cca cag atc ttc cga gac agg acg gat    4333
Pro Ser Phe Ser Asn Ser Phe Pro Gln Ile Phe Arg Asp Arg Thr Asp
            290                 295                 300 atc cag tgc ctt atc cca tgt gcc att gac cag gat cct tac ttt aga    4381
Ile Gln Cys Leu Ile Pro Cys Ala Ile Asp Gln Asp Pro Tyr Phe Arg
        305                 310                 315 atg aca agg gac gtc gcc ccc agg atc ggc tat cct aaa cca gcc ctg    4429
Met Thr Arg Asp Val Ala Pro Arg Ile Gly Tyr Pro Lys Pro Ala Leu
    320                 325                 330 ttg cac tcc acc ttc ttc cca gcc ctg cag ggc gcc cag acc aaa atg    4477
Leu His Ser Thr Phe Phe Pro Ala Leu Gln Gly Ala Gln Thr Lys Met
335                 340                 345                 350 agt gcc agc gac cca aac tcc tcc atc ttc ctc acc gac acg gcc aag    4525
Ser Ala Ser Asp Pro Asn Ser Ser Ile Phe Leu Thr Asp Thr Ala Lys
                355                 360                 365 cag atc aaa acc aag gtc aat aag cat gcg ttt tct gga ggg aga gac    4573
Gln Ile Lys Thr Lys Val Asn Lys His Ala Phe Ser Gly Gly Arg Asp
            370                 375                 380 acc atc gag gag cac agg cag ttt ggg ggc aac tgt gat gtg gac gtg    4621
Thr Ile Glu Glu His Arg Gln Phe Gly Gly Asn Cys Asp Val Asp Val
        385                 390                 395 tct ttc atg tac ctg acc ttc ttc ctc gag gac gac gac aag ctc gag    4669
Ser Phe Met Tyr Leu Thr Phe Phe Leu Glu Asp Asp Asp Lys Leu Glu
    400                 405                 410 cag atc agg aag gat tac acc agc gga gcc atg ctc acc ggt gag ctc    4717
Gln Ile Arg Lys Asp Tyr Thr Ser Gly Ala Met Leu Thr Gly Glu Leu
415                 420                 425                 430 aag aag gca ctc ata gag gtt ctg cag ccc ttg atc gca gag cac cag    4765
Lys Lys Ala Leu Ile Glu Val Leu Gln Pro Leu Ile Ala Glu His Gln
                435                 440                 445 gcc cgg cgc aag gag gtc acg gat gag ata gtg aaa gag ttc atg act    4813
Ala Arg Arg Lys Glu Val Thr Asp Glu Ile Val Lys Glu Phe Met Thr
            450                 455                 460
```

```
ccc cgg aag ctg tcc ttc gac ttt cag aag ctt gcg gcc gca ctc gag    4861
Pro Arg Lys Leu Ser Phe Asp Phe Gln Lys Leu Ala Ala Ala Leu Glu
        465                 470                 475 cac cac cac cac cac cac tgagatccgg ctgctaacaa agcccgaaag           4909
His His His His His His
    480 gaagctgagt tggctgctgc caccgctgag caataactag cataaccct tggggcctct   4969 aaacgggtct tgagggtttt tttgctgaaa ggaggaacta tatccggat              5018

<210> SEQ ID NO 10
<211> LENGTH: 484
<212> TYPE: PRT
<213> ORGANISM: Artificial Sequence
<220> FEATURE:
<223> OTHER INFORMATION: Description of Artificial Sequence: human
      full-length TrpRS in pET20B

<400> SEQUENCE: 10
```

Met Pro Asn Ser Glu Pro Ala Ser Leu Leu Glu Leu Phe Asn Ser Ile
 1               5                  10                  15

Ala Thr Gln Gly Glu Leu Val Arg Ser Leu Lys Ala Gly Asn Ala Ser
            20                  25                  30

Lys Asp Glu Ile Asp Ser Ala Val Lys Met Leu Val Ser Leu Lys Met
        35                  40                  45

Ser Tyr Lys Ala Ala Ala Gly Glu Asp Tyr Lys Ala Asp Cys Pro Pro
    50                  55                  60

Gly Asn Pro Ala Pro Thr Ser Asn His Gly Pro Asp Ala Thr Glu Ala
65                  70                  75                  80

Glu Glu Asp Phe Val Asp Pro Trp Thr Val Gln Thr Ser Ser Ala Lys
                85                  90                  95

Gly Ile Asp Tyr Asp Lys Leu Ile Val Arg Phe Gly Ser Ser Lys Ile
            100                 105                 110

Asp Lys Glu Leu Ile Asn Arg Ile Glu Arg Ala Thr Gly Gln Arg Pro
        115                 120                 125

His His Phe Leu Arg Arg Gly Ile Phe Phe Ser His Arg Asp Met Asn
    130                 135                 140

Gln Val Leu Asp Ala Tyr Glu Asn Lys Lys Pro Phe Tyr Leu Tyr Thr
145                 150                 155                 160

Gly Arg Gly Pro Ser Ser Glu Ala Met His Val Gly His Leu Ile Pro
                165                 170                 175

Phe Ile Phe Thr Lys Trp Leu Gln Asp Val Phe Asn Val Pro Leu Val
            180                 185                 190

Ile Gln Met Thr Asp Asp Glu Lys Tyr Leu Trp Lys Asp Leu Thr Leu
        195                 200                 205

Asp Gln Ala Tyr Gly Asp Ala Val Glu Asn Ala Lys Asp Ile Ile Ala
    210                 215                 220

Cys Gly Phe Asp Ile Asn Lys Thr Phe Ile Phe Ser Asp Leu Asp Tyr
225                 230                 235                 240

Met Gly Met Ser Ser Gly Phe Tyr Lys Asn Val Val Lys Ile Gln Lys
                245                 250                 255

His Val Thr Phe Asn Gln Val Lys Gly Ile Phe Gly Phe Thr Asp Ser
            260                 265                 270

Asp Cys Ile Gly Lys Ile Ser Phe Pro Ala Ile Gln Ala Ala Pro Ser
        275                 280                 285

Phe Ser Asn Ser Phe Pro Gln Ile Phe Arg Asp Arg Thr Asp Ile Gln

```
                  290                 295                 300
Cys Leu Ile Pro Cys Ala Ile Asp Gln Asp Pro Tyr Phe Arg Met Thr
305                 310                 315                 320

Arg Asp Val Ala Pro Arg Ile Gly Tyr Pro Lys Pro Ala Leu Leu His
                325                 330                 335

Ser Thr Phe Phe Pro Ala Leu Gln Gly Ala Gln Thr Lys Met Ser Ala
            340                 345                 350

Ser Asp Pro Asn Ser Ser Ile Phe Leu Thr Asp Thr Ala Lys Gln Ile
        355                 360                 365

Lys Thr Lys Val Asn Lys His Ala Phe Ser Gly Gly Arg Asp Thr Ile
370                 375                 380

Glu Glu His Arg Gln Phe Gly Gly Asn Cys Asp Val Asp Val Ser Phe
385                 390                 395                 400

Met Tyr Leu Thr Phe Phe Leu Glu Asp Asp Asp Lys Leu Glu Gln Ile
                405                 410                 415

Arg Lys Asp Tyr Thr Ser Gly Ala Met Leu Thr Gly Glu Leu Lys Lys
            420                 425                 430

Ala Leu Ile Glu Val Leu Gln Pro Leu Ile Ala Glu His Gln Ala Arg
        435                 440                 445

Arg Lys Glu Val Thr Asp Glu Ile Val Lys Glu Phe Met Thr Pro Arg
    450                 455                 460

Lys Leu Ser Phe Asp Phe Gln Lys Leu Ala Ala Ala Leu Glu His His
465                 470                 475                 480

His His His His

<210> SEQ ID NO 11
<211> LENGTH: 4877
<212> TYPE: DNA
<213> ORGANISM: Artificial Sequence
<220> FEATURE:
<221> NAME/KEY: CDS
<222> LOCATION: (3428)..(4738)
<220> FEATURE:
<223> OTHER INFORMATION: Description of Artificial Sequence: human mini
      TrpRS in pET20B

<400> SEQUENCE: 11
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta atcggggggc tccctttagg   180
gttccgattt agtgctttac ggcacctcga ccccaaaaaa cttgattagg gtgatggttc   240
acgtagtggg ccatcgccct gatagacggt ttttcgccct ttgacgttgg agtccacgtt   300
ctttaatagt ggactcttgt tccaaactgg aacaacactc aaccctatct cggtctattc   360
ttttgattta agggattt tgccgatttc ggcctattgg ttaaaaaatg agctgattta    420
acaaaaattt aacgcgaatt ttaacaaaat attaacgttt acaatttcag gtggcacttt   480
tcggggaaat gtgcgcggaa cccctatttg tttatttttc taaatacatt caaatatgta   540
tccgctcatg agacaataac cctgataaat gcttcaataa tattgaaaaa ggaagagtat   600
gagtattcaa catttccgtg tcgcccttat ccctttttt gcggcatttt gccttcctgt    660
ttttgctcac ccagaaacgc tggtgaaagt aaaagatgct gaagatcagt tgggtgcacg   720
agtgggttac atcgaactgg atctcaacag cggtaagatc cttgagagtt ttcgccccga   780
agaacgtttt ccaatgatga gcacttttaa agttctgcta tgtggcgcgg tattatcccg   840
```

```
tattgacgcc gggcaagagc aactcggtcg ccgcatacac tattctcaga atgacttggt    900
tgagtactca ccagtcacag aaaagcatct tacggatggc atgacagtaa gagaattatg    960
cagtgctgcc ataaccatga gtgataaacac tgcggccaac ttacttctga caacgatcgg   1020
aggaccgaag gagctaaccg cttttttgca caacatgggg gatcatgtaa ctcgccttga   1080
tcgttgggaa ccggagctga atgaagccat accaaacgac gagcgtgaca ccacgatgcc   1140
tgcagcaatg gcaacaacgt tgcgcaaact attaactggc gaactactta ctctagcttc   1200
ccggcaacaa ttaatagact ggatggaggc ggataaagtt gcaggaccac ttctgcgctc   1260
ggcccttccg gctggctggt ttattgctga taaatctgga gccggtgagc gtgggtctcg   1320
cggtatcatt gcagcactgg ggccagatgg taagccctcc cgtatcgtag ttatctacac   1380
gacggggagt caggcaacta tggatgaacg aaatagacag atcgctgaga taggtgcctc   1440
actgattaag cattggtaac tgtcagacca agtttactca tatatacttt agattgattt   1500
aaaacttcat ttttaattta aaaggatcta ggtgaagatc ctttttgata atctcatgac   1560
caaaatccct taacgtgagt tttcgttcca ctgagcgtca ccccgtag aaaagatcaa   1620
aggatcttct tgagatcctt ttttctgcg cgtaatctgc tgcttgcaaa caaaaaaacc   1680
accgctacca gcggtggttt gtttgccgga tcaagagcta ccaactcttt ttccgaaggt   1740
aactggcttc agcagagcgc agataccaaa tactgtcctt ctagtgtagc cgtagttagg   1800
ccaccacttc aagaactctg tagcaccgcc tacatacctc gctctgctaa tcctgttacc   1860
agtggctgct gccagtggcg ataagtcgtg tcttaccggg ttggactcaa gacgatagtt   1920
accggataag gcgcagcggt cgggctgaac ggggggttcg tgcacacagc ccagcttgga   1980
gcgaacgacc tacaccgaac tgagatacct acagcgtgag ctatgagaaa gcgccacgct   2040
tcccgaaggg agaaaggcgg acaggtatcc ggtaagcggc agggtcggaa caggagagcg   2100
cacgagggag cttccagggg gaaacgcctg gtatctttat agtcctgtcg ggtttcgcca   2160
cctctgactt gagcgtcgat ttttgtgatg ctcgtcaggg gggcggagcc tatggaaaaa   2220
cgccagcaac gcggcctttt tacggttcct ggccttttgc tggccttttg ctcacatgtt   2280
ctttcctgcg ttatcccctg attctgtgga taaccgtatt accgcctttg agtgagctga   2340
taccgctcgc cgcagccgaa cgaccgagcg cagcgagtca gtgagcgagg aagcggaaga   2400
gcgcctgatg cggtattttc tccttacgca tctgtgcggt atttcacacc gcatatatgg   2460
tgcactctca gtacaatctg ctctgatgcc gcatagttaa gccagtatac actccgctat   2520
cgctacgtga ctgggtcatg gctgcgcccc gacacccgcc aacacccgct gacgcgccct   2580
gacgggcttg tctgctcccg gcatccgctt acagacaagc tgtgaccgtc tccgggagct   2640
gcatgtgtca gaggttttca ccgtcatcac cgaaacgcgc gaggcagctg cggtaaagct   2700
catcagcgtg gtcgtgaagc gattcacaga tgtctgcctg ttcatccgcg tccagctcgt   2760
tgagtttctc cagaagcgtt aatgtctggc ttctgataaa gcgggccatg ttaagggcgg   2820
ttttttcctg tttggtcact gatgcctccg tgtaaggggg atttctgttc atgggggtaa   2880
tgataccgat gaaacgagag aggatgctca cgatacgggt tactgatgat gaacatgccc   2940
ggttactgga acgttgtgag ggtaaacaac tggcggtatg gatgcggcgg gaccagagaa   3000
aaatcactca gggtcaatgc cagcgcttcg ttaatacaga tgtaggtgtt ccacaggta    3060
gccagcagca tcctgcgatg cagatccgga acataatggt gcagggcgct gacttccgcg   3120
tttccagact ttacgaaaca cggaaaccga agaccattca tgttgttgct caggtcgcag   3180
acgttttgca gcagcagtcg cttcacgttc gctcgcgtat cggtgattca ttctgctaac   3240
```

```
cagtaaggca accccgccag cctagccggg tcctcaacga caggagcacg atcatgcgca      3300
cccgtggcca ggacccaacg ctgcccgaga tctcgatccc gcgaattaa tacgactcac       3360 tataggaga ccacaacggt ttccctctag aaataatttt gtttaacttt aagaaggaga      3420 tatacat atg agc tac aaa gct gcc gcg ggg gag gat tac aag gct gac        3469
        Met Ser Tyr Lys Ala Ala Ala Gly Glu Asp Tyr Lys Ala Asp
          1               5                  10 tgt cct cca ggg aac cca gca cct acc agt aat cat ggc cca gat gcc        3517
Cys Pro Pro Gly Asn Pro Ala Pro Thr Ser Asn His Gly Pro Asp Ala
 15              20                  25                  30 aca gaa gct gaa gag gat ttt gtg gac cca tgg aca gta cag aca agc        3565
Thr Glu Ala Glu Glu Asp Phe Val Asp Pro Trp Thr Val Gln Thr Ser
             35                  40                  45 agt gca aaa ggc ata gac tac gat aag ctc att gtt cgg ttt gga agt        3613
Ser Ala Lys Gly Ile Asp Tyr Asp Lys Leu Ile Val Arg Phe Gly Ser
         50                  55                  60 agt aaa att gac aaa gag cta ata aac cga ata gag aga gcc acc ggc        3661
Ser Lys Ile Asp Lys Glu Leu Ile Asn Arg Ile Glu Arg Ala Thr Gly
     65                  70                  75 caa aga cca cac cac ttc ctg cgc aga ggc atc ttc ttc tca cac aga        3709
Gln Arg Pro His His Phe Leu Arg Arg Gly Ile Phe Phe Ser His Arg
 80              85                  90 gat atg aat cag gtt ctt gat gcc tat gaa aat aag aag cca ttt tat        3757
Asp Met Asn Gln Val Leu Asp Ala Tyr Glu Asn Lys Lys Pro Phe Tyr
 95             100                 105                 110 ctg tac acg ggc cgg ggc ccc tct tct gaa gca atg cat gta ggt cac        3805
Leu Tyr Thr Gly Arg Gly Pro Ser Ser Glu Ala Met His Val Gly His
            115                 120                 125 ctc att cca ttt att ttc aca aag tgg ctc cag gat gta ttt aac gtg        3853
Leu Ile Pro Phe Ile Phe Thr Lys Trp Leu Gln Asp Val Phe Asn Val
        130                 135                 140 ccc ttg gtc atc cag atg acg gat gac gag aag tat ctg tgg aag gac        3901
Pro Leu Val Ile Gln Met Thr Asp Asp Glu Lys Tyr Leu Trp Lys Asp
    145                 150                 155 ctg acc ctg gac cag gcc tat ggc gat gct gtt gag aat gcc aag gac        3949
Leu Thr Leu Asp Gln Ala Tyr Gly Asp Ala Val Glu Asn Ala Lys Asp
160                 165                 170 atc atc gcc tgt ggc ttt gac atc aac aag act ttc ata ttc tct gac        3997
Ile Ile Ala Cys Gly Phe Asp Ile Asn Lys Thr Phe Ile Phe Ser Asp
175                 180                 185                 190 ctg gac tac atg ggg atg agc tca ggt ttc tac aaa aat gtg gtg aag        4045
Leu Asp Tyr Met Gly Met Ser Ser Gly Phe Tyr Lys Asn Val Val Lys
                195                 200                 205 att caa aag cat gtt acc ttc aac caa gtg aaa ggc att ttc ggc ttc        4093
Ile Gln Lys His Val Thr Phe Asn Gln Val Lys Gly Ile Phe Gly Phe
            210                 215                 220 act gac agc gac tgc att ggg aag atc agt ttt cct gcc atc cag gct        4141
Thr Asp Ser Asp Cys Ile Gly Lys Ile Ser Phe Pro Ala Ile Gln Ala
        225                 230                 235 gct ccc tcc ttc agc aac tca ttc cca cag atc ttc cga gac agg acg        4189
Ala Pro Ser Phe Ser Asn Ser Phe Pro Gln Ile Phe Arg Asp Arg Thr
    240                 245                 250 gat atc cag tgc ctt atc cca tgt gcc att gac cag gat cct tac ttt        4237
Asp Ile Gln Cys Leu Ile Pro Cys Ala Ile Asp Gln Asp Pro Tyr Phe
255                 260                 265                 270 aga atg aca agg gac gtc gcc ccc agg atc ggc tat cct aaa cca gcc        4285
Arg Met Thr Arg Asp Val Ala Pro Arg Ile Gly Tyr Pro Lys Pro Ala
                275                 280                 285
```

| | | | | | | | | | | | | | | | | |
|---|---|---|---|---|---|---|---|---|---|---|---|---|---|---|---|---|
| ctg | ttg | cac | tcc | acc | ttc | ttc | cca | gcc | ctg | cag | ggc | gcc | cag | acc | aaa | 4333 |
| Leu | Leu | His | Ser | Thr | Phe | Phe | Pro | Ala | Leu | Gln | Gly | Ala | Gln | Thr | Lys | |
| | | | 290 | | | | 295 | | | | | 300 | | | | |
| atg | agt | gcc | agc | gac | cca | aac | tcc | tcc | atc | ttc | ctc | acc | gac | acg | gcc | 4381 |
| Met | Ser | Ala | Ser | Asp | Pro | Asn | Ser | Ser | Ile | Phe | Leu | Thr | Asp | Thr | Ala | |
| | | 305 | | | | | 310 | | | | | 315 | | | | |
| aag | cag | atc | aaa | acc | aag | gtc | aat | aag | cat | gcg | ttt | tct | gga | ggg | aga | 4429 |
| Lys | Gln | Ile | Lys | Thr | Lys | Val | Asn | Lys | His | Ala | Phe | Ser | Gly | Gly | Arg | |
| 320 | | | | | 325 | | | | | 330 | | | | | | |
| gac | acc | atc | gag | gag | cac | agg | cag | ttt | ggg | ggc | aac | tgt | gat | gtg | gac | 4477 |
| Asp | Thr | Ile | Glu | Glu | His | Arg | Gln | Phe | Gly | Gly | Asn | Cys | Asp | Val | Asp | |
| 335 | | | | | 340 | | | | | 345 | | | | | 350 | |
| gtg | tct | ttc | atg | tac | ctg | acc | ttc | ttc | ctc | gag | gac | gac | gac | aag | ctc | 4525 |
| Val | Ser | Phe | Met | Tyr | Leu | Thr | Phe | Phe | Leu | Glu | Asp | Asp | Asp | Lys | Leu | |
| | | | 355 | | | | | 360 | | | | | 365 | | | |
| gag | cag | atc | agg | aag | gat | tac | acc | agc | gga | gcc | atg | ctc | acc | ggt | gag | 4573 |
| Glu | Gln | Ile | Arg | Lys | Asp | Tyr | Thr | Ser | Gly | Ala | Met | Leu | Thr | Gly | Glu | |
| | | | 370 | | | | | 375 | | | | | 380 | | | |
| ctc | aag | aag | gca | ctc | ata | gag | gtt | ctg | cag | ccc | ttg | atc | gca | gag | cac | 4621 |
| Leu | Lys | Lys | Ala | Leu | Ile | Glu | Val | Leu | Gln | Pro | Leu | Ile | Ala | Glu | His | |
| | | 385 | | | | | 390 | | | | | 395 | | | | |
| cag | gcc | cgg | cgc | aag | gag | gtc | acg | gat | gag | ata | gtg | aaa | gag | ttc | atg | 4669 |
| Gln | Ala | Arg | Arg | Lys | Glu | Val | Thr | Asp | Glu | Ile | Val | Lys | Glu | Phe | Met | |
| | 400 | | | | | 405 | | | | | 410 | | | | | |
| act | ccc | cgg | aag | ctg | tcc | ttc | gac | ttt | cag | aag | ctt | gcg | gcc | gca | ctc | 4717 |
| Thr | Pro | Arg | Lys | Leu | Ser | Phe | Asp | Phe | Gln | Lys | Leu | Ala | Ala | Ala | Leu | |
| 415 | | | | | 420 | | | | | 425 | | | | | 430 | |
| gag | cac | cac | cac | cac | cac | cac | tgagatccgg ctgctaacaa agcccgaaag | | | | | | | | 4768 |
| Glu | His | His | His | His | His | His | | | | | | | | | | |
| | | | | 435 | | | | | | | | | | | | | gaagctgagt tggctgctgc caccgctgag caataactag cataacccct tggggcctct     4828 aaacgggtct tgaggggttt tttgctgaaa ggaggaacta tatccggat                4877

<210> SEQ ID NO 12
<211> LENGTH: 437
<212> TYPE: PRT
<213> ORGANISM: Artificial Sequence
<220> FEATURE:
<223> OTHER INFORMATION: Description of Artificial Sequence: human mini
      TrpRS in pET20B

<400> SEQUENCE: 12

Met Ser Tyr Lys Ala Ala Ala Gly Glu Asp Tyr Lys Ala Asp Cys Pro
 1               5                  10                  15

Pro Gly Asn Pro Ala Pro Thr Ser Asn His Gly Pro Asp Ala Thr Glu
                20                  25                  30

Ala Glu Glu Asp Phe Val Asp Pro Trp Thr Val Gln Thr Ser Ser Ala
            35                  40                  45

Lys Gly Ile Asp Tyr Asp Lys Leu Ile Val Arg Phe Gly Ser Ser Lys
        50                  55                  60

Ile Asp Lys Glu Leu Ile Asn Arg Ile Glu Arg Ala Thr Gly Gln Arg
 65                  70                  75                  80

Pro His His Phe Leu Arg Arg Gly Ile Phe Phe Ser His Arg Asp Met
                85                  90                  95

Asn Gln Val Leu Asp Ala Tyr Glu Asn Lys Lys Pro Phe Tyr Leu Tyr
            100                 105                 110

Thr Gly Arg Gly Pro Ser Ser Glu Ala Met His Val Gly His Leu Ile
        115                 120                 125

```
Pro Phe Ile Phe Thr Lys Trp Leu Gln Asp Val Phe Asn Val Pro Leu
    130                 135                 140
Val Ile Gln Met Thr Asp Asp Glu Lys Tyr Leu Trp Lys Asp Leu Thr
145                 150                 155                 160
Leu Asp Gln Ala Tyr Gly Asp Ala Val Glu Asn Ala Lys Asp Ile Ile
                165                 170                 175
Ala Cys Gly Phe Asp Ile Asn Lys Thr Phe Ile Phe Ser Asp Leu Asp
                180                 185                 190
Tyr Met Gly Met Ser Ser Gly Phe Tyr Lys Asn Val Val Lys Ile Gln
            195                 200                 205
Lys His Val Thr Phe Asn Gln Val Lys Gly Ile Phe Gly Phe Thr Asp
    210                 215                 220
Ser Asp Cys Ile Gly Lys Ile Ser Phe Pro Ala Ile Gln Ala Ala Pro
225                 230                 235                 240
Ser Phe Ser Asn Ser Phe Pro Gln Ile Phe Arg Asp Arg Thr Asp Ile
                245                 250                 255
Gln Cys Leu Ile Pro Cys Ala Ile Asp Gln Asp Pro Tyr Phe Arg Met
                260                 265                 270
Thr Arg Asp Val Ala Pro Arg Ile Gly Tyr Pro Lys Pro Ala Leu Leu
            275                 280                 285
His Ser Thr Phe Phe Pro Ala Leu Gln Gly Ala Gln Thr Lys Met Ser
    290                 295                 300
Ala Ser Asp Pro Asn Ser Ser Ile Phe Leu Thr Asp Thr Ala Lys Gln
305                 310                 315                 320
Ile Lys Thr Lys Val Asn Lys His Ala Phe Ser Gly Gly Arg Asp Thr
                325                 330                 335
Ile Glu Glu His Arg Gln Phe Gly Gly Asn Cys Asp Val Asp Val Ser
            340                 345                 350
Phe Met Tyr Leu Thr Phe Phe Leu Glu Asp Asp Lys Leu Glu Gln
    355                 360                 365
Ile Arg Lys Asp Tyr Thr Ser Gly Ala Met Leu Thr Gly Glu Leu Lys
    370                 375                 380
Lys Ala Leu Ile Glu Val Leu Gln Pro Leu Ile Ala Glu His Gln Ala
385                 390                 395                 400
Arg Arg Lys Glu Val Thr Asp Glu Ile Val Lys Glu Phe Met Thr Pro
                405                 410                 415
Arg Lys Leu Ser Phe Asp Phe Gln Lys Leu Ala Ala Ala Leu Glu His
                420                 425                 430
His His His His
        435

<210> SEQ ID NO 13
<211> LENGTH: 4811
<212> TYPE: DNA
<213> ORGANISM: Artificial Sequence
<220> FEATURE:
<221> NAME/KEY: CDS
<222> LOCATION: (3428)..(4672)
<220> FEATURE:
<223> OTHER INFORMATION: Description of Artificial Sequence: human
      supermini TrpRS in pET20B

<400> SEQUENCE: 13
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcggggc tcccttttagg     180
```

```
gttccgattt agtgctttac ggcacctcga ccccaaaaaa cttgattagg gtgatggttc      240
acgtagtggg ccatcgccct gatagacggt ttttcgccct ttgacgttgg agtccacgtt      300
ctttaatagt ggactcttgt tccaaactgg aacaacactc aaccctatct cggtctattc      360
ttttgattta aagggatttt tgccgatttc ggcctattgg ttaaaaaatg agctgattta      420
acaaaaattt aacgcgaatt ttaacaaaat attaacgttt acaatttcag gtggcacttt      480
tcggggaaat gtgcgcggaa cccctatttg tttattttc taaatacatt caaatatgta       540
tccgctcatg agacaataac cctgataaat gcttcaataa tattgaaaaa ggaagagtat      600
gagtattcaa catttccgtg tcgcccttat cccttttttt gcggcatttt gccttcctgt      660
ttttgctcac ccagaaacgc tggtgaaagt aaaagatgct gaagatcagt tgggtgcacg      720
agtgggttac atcgaactgg atctcaacag cggtaagatc cttgagagtt ttcgccccga      780
agaacgtttt ccaatgatga gcacttttaa agttctgcta tgtggcgcgg tattatcccg      840
tattgacgcc gggcaagagc aactcggtcg ccgcatacac tattctcaga atgacttggt      900
tgagtactca ccagtcacag aaaagcatct tacggatggc atgacagtaa gagaattatg      960
cagtgctgcc ataaccatga gtgataacac tgcggccaac ttacttctga caacgatcgg     1020
aggaccgaag gagctaaccg cttttttgca acatggggg atcatgtaa ctcgccttga       1080 tcgttgggaa ccggagctga atgaagccat accaaacgac gagcgtgaca ccacgatgcc     1140
tgcagcaatg gcaacaacgt tgcgcaaact attaactggc gaactactta ctctagcttc     1200
ccggcaacaa ttaatagact ggatggaggc ggataaagtt gcaggaccac ttctgcgctc     1260
ggcccttccg gctggctggt ttattgctga taaatctgga gccggtgagc gtgggtctcg     1320
cggtatcatt gcagcactgg ggccagatgg taagccctcc cgtatcgtag ttatctacac     1380
gacggggagt caggcaacta tggatgaacg aaatagacag atcgctgaga taggtgcctc     1440
actgattaag cattggtaac tgtcagacca agtttactca tatatacttt agattgattt     1500
aaaacttcat ttttaattta aaaggatcta ggtgaagatc ctttttgata atctcatgac     1560
caaaatccct taacgtgagt tttcgttcca ctgagcgtca gaccccgtag aaaagatcaa     1620
aggatcttct tgagatcctt ttttttctgcg cgtaatctgc tgcttgcaaa caaaaaaacc     1680
accgctacca gcggtggttt gtttgccgga tcaagagcta ccaactcttt ttccgaaggt     1740
aactggcttc agcagagcgc agataccaaa tactgtcctt ctagtgtagc cgtagttagg     1800
ccaccacttc aagaactctg tagcaccgcc tacatacctc gctctgctaa tcctgttacc     1860
agtggctgct gccagtggcg ataagtcgtg tcttaccggg ttggactcaa gacgatagtt     1920
accggataag gcgcagcggt cgggctgaac ggggggttcg tgcacacagc ccagcttgga     1980
gcgaacgacc tacaccgaac tgagatacct acagcgtgag ctatgagaaa gcgccacgct     2040
tcccgaaggg agaaaggcgg acaggtatcc ggtaagcggc agggtcggaa caggagagcg     2100
cacgagggag cttccagggg gaaacgcctg gtatctttat agtcctgtcg gtttcgccac     2160
cctctgactt gagcgtcgat ttttgtgatg ctcgtcaggg gggcggagcc tatggaaaaa     2220
cgccagcaac gcggcctttt tacggttcct ggccttttgc tggccttttg ctcacatgtt     2280
ctttcctgcg ttatccctg attctgtgga taaccgtatt accgcctttg agtgagctga     2340
taccgctcgc cgcagccgaa cgaccgagcg cagcgagtca gtgagcgagg aagcggaaga     2400
gcgcctgatg cggtattttc tccttacgca tctgtgcggt atttcacacc gcatatatgg     2460
tgcactctca gtacaatctg ctctgatgcc gcatagttaa gccagtatac actccgctat     2520
```

```
cgctacgtga ctgggtcatg gctgcgcccc gacacccgcc aacacccgct gacgcgccct    2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760
tgagtttctc cagaagcgtt aatgtctggc ttctgataaa gcgggccatg ttaagggcgg    2820
ttttttcctg tttggtcact gatgcctccg tgtaagggggg atttctgttc atggggtaa    2880 tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggcca ggacccaacg ctgcccgaga tctcgatccc gcgaaattaa tacgactcac    3360
tatagggaga ccacaacggt ttccctctag aaataatttt gtttaacttt aagaaggaga    3420 tatacat atg agt aat cat ggc cca gat gcc aca gaa gct gaa gag gat    3469
        Met Ser Asn His Gly Pro Asp Ala Thr Glu Ala Glu Glu Asp
          1               5                  10 ttt gtg gac cca tgg aca gta cag aca agc agt gca aaa ggc ata gac    3517
Phe Val Asp Pro Trp Thr Val Gln Thr Ser Ser Ala Lys Gly Ile Asp
 15                  20                  25                  30 tac gat aag ctc att gtt cgg ttt gga agt agt aaa att gac aaa gag    3565
Tyr Asp Lys Leu Ile Val Arg Phe Gly Ser Ser Lys Ile Asp Lys Glu
                 35                  40                  45 cta ata aac cga ata gag aga gcc acc ggc caa aga cca cac cac ttc    3613
Leu Ile Asn Arg Ile Glu Arg Ala Thr Gly Gln Arg Pro His His Phe
             50                  55                  60 ctg cgc aga ggc atc ttc ttc tca cac aga gat atg aat cag gtt ctt    3661
Leu Arg Arg Gly Ile Phe Phe Ser His Arg Asp Met Asn Gln Val Leu
 65                  70                  75 gat gcc tat gaa aat aag aag cca ttt tat ctg tac acg ggc cgg ggc    3709
Asp Ala Tyr Glu Asn Lys Lys Pro Phe Tyr Leu Tyr Thr Gly Arg Gly
     80                  85                  90 ccc tct tct gaa gca atg cat gta ggt cac ctc att cca ttt att ttc    3757
Pro Ser Ser Glu Ala Met His Val Gly His Leu Ile Pro Phe Ile Phe
 95                 100                 105                 110 aca aag tgg ctc cag gat gta ttt aac gtg ccc ttg gtc atc cag atg    3805
Thr Lys Trp Leu Gln Asp Val Phe Asn Val Pro Leu Val Ile Gln Met
                115                 120                 125 acg gat gac gag aag tat ctg tgg aag gac ctg acc ctg gac cag gcc    3853
Thr Asp Asp Glu Lys Tyr Leu Trp Lys Asp Leu Thr Leu Asp Gln Ala
            130                 135                 140 tat ggc gat gct gtt gag aat gcc aag gac atc atc gcc tgt ggc ttt    3901
Tyr Gly Asp Ala Val Glu Asn Ala Lys Asp Ile Ile Ala Cys Gly Phe
145                 150                 155 gac atc aac aag act ttc ata ttc tct gac ctg gac tac atg ggg atg    3949
Asp Ile Asn Lys Thr Phe Ile Phe Ser Asp Leu Asp Tyr Met Gly Met
 160                 165                 170 agc tca ggt ttc tac aaa aat gtg gtg aag att caa aag cat gtt acc    3997
Ser Ser Gly Phe Tyr Lys Asn Val Val Lys Ile Gln Lys His Val Thr
175                 180                 185                 190 ttc aac caa gtg aaa ggc att ttc ggc ttc act gac agc gac tgc att    4045
```

|  |  |  |  |  |  |  |  |  |  |  |  |  |  |  |  |
|---|---|---|---|---|---|---|---|---|---|---|---|---|---|---|---|
| Phe | Asn | Gln | Val | Lys | Gly | Ile | Phe | Gly | Phe | Thr | Asp | Ser | Asp | Cys | Ile |
|  |  |  | 195 |  |  |  | 200 |  |  |  | 205 |  |  |  |  |

| ggg | aag | atc | agt | ttt | cct | gcc | atc | cag | gct | gct | ccc | tcc | ttc | agc | aac | 4093 |
|---|---|---|---|---|---|---|---|---|---|---|---|---|---|---|---|---|
| Gly | Lys | Ile | Ser | Phe | Pro | Ala | Ile | Gln | Ala | Ala | Pro | Ser | Phe | Ser | Asn |  |
|  |  |  | 210 |  |  |  | 215 |  |  |  | 220 |  |  |  |  |  |

| tca | ttc | cca | cag | atc | ttc | cga | gac | agg | acg | gat | atc | cag | tgc | ctt | atc | 4141 |
|---|---|---|---|---|---|---|---|---|---|---|---|---|---|---|---|---|
| Ser | Phe | Pro | Gln | Ile | Phe | Arg | Asp | Arg | Thr | Asp | Ile | Gln | Cys | Leu | Ile |  |
|  |  | 225 |  |  |  |  | 230 |  |  |  |  | 235 |  |  |  |  |

| cca | tgt | gcc | att | gac | cag | gat | cct | tac | ttt | aga | atg | aca | agg | gac | gtc | 4189 |
|---|---|---|---|---|---|---|---|---|---|---|---|---|---|---|---|---|
| Pro | Cys | Ala | Ile | Asp | Gln | Asp | Pro | Tyr | Phe | Arg | Met | Thr | Arg | Asp | Val |  |
|  | 240 |  |  |  |  | 245 |  |  |  |  | 250 |  |  |  |  |  |

| gcc | ccc | agg | atc | ggc | tat | cct | aaa | cca | gcc | ctg | ttg | cac | tcc | acc | ttc | 4237 |
|---|---|---|---|---|---|---|---|---|---|---|---|---|---|---|---|---|
| Ala | Pro | Arg | Ile | Gly | Tyr | Pro | Lys | Pro | Ala | Leu | Leu | His | Ser | Thr | Phe |  |
| 255 |  |  |  |  | 260 |  |  |  |  | 265 |  |  |  |  | 270 |  |

| ttc | cca | gcc | ctg | cag | ggc | gcc | cag | acc | aaa | atg | agt | gcc | agc | gac | cca | 4285 |
|---|---|---|---|---|---|---|---|---|---|---|---|---|---|---|---|---|
| Phe | Pro | Ala | Leu | Gln | Gly | Ala | Gln | Thr | Lys | Met | Ser | Ala | Ser | Asp | Pro |  |
|  |  |  |  | 275 |  |  |  |  | 280 |  |  |  |  | 285 |  |  |

| aac | tcc | tcc | atc | ttc | ctc | acc | gac | acg | gcc | aag | cag | atc | aaa | acc | aag | 4333 |
|---|---|---|---|---|---|---|---|---|---|---|---|---|---|---|---|---|
| Asn | Ser | Ser | Ile | Phe | Leu | Thr | Asp | Thr | Ala | Lys | Gln | Ile | Lys | Thr | Lys |  |
|  |  |  | 290 |  |  |  | 295 |  |  |  | 300 |  |  |  |  |  |

| gtc | aat | aag | cat | gcg | ttt | tct | gga | ggg | aga | gac | acc | atc | gag | gag | cac | 4381 |
|---|---|---|---|---|---|---|---|---|---|---|---|---|---|---|---|---|
| Val | Asn | Lys | His | Ala | Phe | Ser | Gly | Gly | Arg | Asp | Thr | Ile | Glu | Glu | His |  |
|  |  | 305 |  |  |  |  | 310 |  |  |  |  | 315 |  |  |  |  |

| agg | cag | ttt | ggg | ggc | aac | tgt | gat | gtg | gac | gtg | tct | ttc | atg | tac | ctg | 4429 |
|---|---|---|---|---|---|---|---|---|---|---|---|---|---|---|---|---|
| Arg | Gln | Phe | Gly | Gly | Asn | Cys | Asp | Val | Asp | Val | Ser | Phe | Met | Tyr | Leu |  |
|  | 320 |  |  |  |  | 325 |  |  |  |  | 330 |  |  |  |  |  |

| acc | ttc | ttc | ctc | gag | gac | gac | gac | aag | ctc | gag | cag | atc | agg | aag | gat | 4477 |
|---|---|---|---|---|---|---|---|---|---|---|---|---|---|---|---|---|
| Thr | Phe | Phe | Leu | Glu | Asp | Asp | Asp | Lys | Leu | Glu | Gln | Ile | Arg | Lys | Asp |  |
| 335 |  |  |  |  | 340 |  |  |  |  | 345 |  |  |  |  | 350 |  |

| tac | acc | agc | gga | gcc | atg | ctc | acc | ggt | gag | ctc | aag | aag | gca | ctc | ata | 4525 |
|---|---|---|---|---|---|---|---|---|---|---|---|---|---|---|---|---|
| Tyr | Thr | Ser | Gly | Ala | Met | Leu | Thr | Gly | Glu | Leu | Lys | Lys | Ala | Leu | Ile |  |
|  |  |  |  | 355 |  |  |  |  | 360 |  |  |  |  | 365 |  |  |

| gag | gtt | ctg | cag | ccc | ttg | atc | gca | gag | cac | cag | gcc | cgg | cgc | aag | gag | 4573 |
|---|---|---|---|---|---|---|---|---|---|---|---|---|---|---|---|---|
| Glu | Val | Leu | Gln | Pro | Leu | Ile | Ala | Glu | His | Gln | Ala | Arg | Arg | Lys | Glu |  |
|  |  |  | 370 |  |  |  |  | 375 |  |  |  |  | 380 |  |  |  |

| gtc | acg | gat | gag | ata | gtg | aaa | gag | ttc | atg | act | ccc | cgg | aag | ctg | tcc | 4621 |
|---|---|---|---|---|---|---|---|---|---|---|---|---|---|---|---|---|
| Val | Thr | Asp | Glu | Ile | Val | Lys | Glu | Phe | Met | Thr | Pro | Arg | Lys | Leu | Ser |  |
|  |  | 385 |  |  |  |  | 390 |  |  |  |  | 395 |  |  |  |  |

| ttc | gac | ttt | cag | aag | ctt | gcg | gcc | gca | ctc | gag | cac | cac | cac | cac | cac | 4669 |
|---|---|---|---|---|---|---|---|---|---|---|---|---|---|---|---|---|
| Phe | Asp | Phe | Gln | Lys | Leu | Ala | Ala | Ala | Leu | Glu | His | His | His | His | His |  |
|  |  |  | 400 |  |  |  |  | 405 |  |  |  |  | 410 |  |  |  |

| cac | tgagatccgg | ctgctaacaa | agcccgaaag | gaagctgagt | tggctgctgc | 4722 |
|---|---|---|---|---|---|---|
| His |  |  |  |  |  |  |
| 415 |  |  |  |  |  |  |

| caccgctgag | caataactag | cataaccect | tggggcctct | aaacgggtct | tgaggggttt | 4782 |
|---|---|---|---|---|---|---|

| tttgctgaaa | ggaggaacta | tatccggat |  |  |  | 4811 |
|---|---|---|---|---|---|---|

<210> SEQ ID NO 14
<211> LENGTH: 415
<212> TYPE: PRT
<213> ORGANISM: Artificial Sequence
<220> FEATURE:
<223> OTHER INFORMATION: Description of Artificial Sequence: human
      supermini TrpRS in pET20B

<400> SEQUENCE: 14

|  |  |  |  |  |  |  |  |  |  |  |  |  |  |  |
|---|---|---|---|---|---|---|---|---|---|---|---|---|---|---|
| Met | Ser | Asn | His | Gly | Pro | Asp | Ala | Thr | Glu | Ala | Glu | Glu | Asp | Phe | Val |
| 1 |  |  |  | 5 |  |  |  |  | 10 |  |  |  |  | 15 |  |

|  |  |  |  |  |  |  |  |  |  |  |  |  |  |
|---|---|---|---|---|---|---|---|---|---|---|---|---|---|
| Asp | Pro | Trp | Thr | Val | Gln | Thr | Ser | Ser | Ala | Lys | Gly | Ile | Asp | Tyr | Asp |
|  |  | 20 |  |  |  |  | 25 |  |  |  |  | 30 |  |  |  |

```
Lys Leu Ile Val Arg Phe Gly Ser Ser Lys Ile Asp Lys Glu Leu Ile
         35                  40                  45

Asn Arg Ile Glu Arg Ala Thr Gly Gln Arg Pro His His Phe Leu Arg
     50                  55                  60

Arg Gly Ile Phe Phe Ser His Arg Asp Met Asn Gln Val Leu Asp Ala
 65                  70                  75                  80

Tyr Glu Asn Lys Lys Pro Phe Tyr Leu Tyr Thr Gly Arg Gly Pro Ser
                 85                  90                  95

Ser Glu Ala Met His Val Gly His Leu Ile Pro Phe Ile Phe Thr Lys
                100                 105                 110

Trp Leu Gln Asp Val Phe Asn Val Pro Leu Val Ile Gln Met Thr Asp
            115                 120                 125

Asp Glu Lys Tyr Leu Trp Lys Asp Leu Thr Leu Asp Gln Ala Tyr Gly
        130                 135                 140

Asp Ala Val Glu Asn Ala Lys Asp Ile Ile Ala Cys Gly Phe Asp Ile
145                 150                 155                 160

Asn Lys Thr Phe Ile Phe Ser Asp Leu Asp Tyr Met Gly Met Ser Ser
                165                 170                 175

Gly Phe Tyr Lys Asn Val Val Lys Ile Gln Lys His Val Thr Phe Asn
                180                 185                 190

Gln Val Lys Gly Ile Phe Gly Phe Thr Asp Ser Asp Cys Ile Gly Lys
            195                 200                 205

Ile Ser Phe Pro Ala Ile Gln Ala Ala Pro Ser Phe Ser Asn Ser Phe
        210                 215                 220

Pro Gln Ile Phe Arg Asp Arg Thr Asp Ile Gln Cys Leu Ile Pro Cys
225                 230                 235                 240

Ala Ile Asp Gln Asp Pro Tyr Phe Arg Met Thr Arg Asp Val Ala Pro
                245                 250                 255

Arg Ile Gly Tyr Pro Lys Pro Ala Leu Leu His Ser Thr Phe Phe Pro
                260                 265                 270

Ala Leu Gln Gly Ala Gln Thr Lys Met Ser Ala Ser Asp Pro Asn Ser
            275                 280                 285

Ser Ile Phe Leu Thr Asp Thr Ala Lys Gln Ile Lys Thr Lys Val Asn
        290                 295                 300

Lys His Ala Phe Ser Gly Gly Arg Asp Thr Ile Glu Glu His Arg Gln
305                 310                 315                 320

Phe Gly Gly Asn Cys Asp Val Asp Val Ser Phe Met Tyr Leu Thr Phe
                325                 330                 335

Phe Leu Glu Asp Asp Asp Lys Leu Glu Gln Ile Arg Lys Asp Tyr Thr
                340                 345                 350

Ser Gly Ala Met Leu Thr Gly Glu Leu Lys Lys Ala Leu Ile Glu Val
            355                 360                 365

Leu Gln Pro Leu Ile Ala Glu His Gln Ala Arg Arg Lys Glu Val Thr
        370                 375                 380

Asp Glu Ile Val Lys Glu Phe Met Thr Pro Arg Lys Leu Ser Phe Asp
385                 390                 395                 400

Phe Gln Lys Leu Ala Ala Ala Leu Glu His His His His His His
                405                 410                 415

<210> SEQ ID NO 15
<211> LENGTH: 4742
<212> TYPE: DNA
<213> ORGANISM: Artificial Sequence
<220> FEATURE:
```

<221> NAME/KEY: CDS
<222> LOCATION: (3428)..(4603)
<220> FEATURE:
<223> OTHER INFORMATION: Description of Artificial Sequence: human inactive TrpRS in pET20B

<400> SEQUENCE: 15

| | |
|---|---|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta atcgggggc tccctttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |
| ctttaatagt ggactcttgt tccaaactgg aacaacactc aaccctatct cggtctattc | 360 |
| ttttgattta aagggatttt gccgatttc ggcctattgg ttaaaaatg agctgattta | 420 |
| acaaaatttt aacgcgaatt ttaacaaaat attaacgttt acaatttcag gtggcacttt | 480 |
| tcggggaaat gtgcgcggaa cccctatttg tttatttttc taaatacatt caaatatgta | 540 |
| tccgctcatg agacaataac cctgataaat gcttcaataa tattgaaaaa ggaagagtat | 600 |
| gagtattcaa catttccgtg tcgcccttat ccctttttt gcggcatttt gccttcctgt | 660 |
| ttttgctcac ccagaaacgc tggtgaaagt aaaagatgct gaagatcagt tgggtgcacg | 720 |
| agtgggttac atcgaactgg atctcaacag cggtaagatc cttgagagtt tcgccccga | 780 |
| agaacgtttt ccaatgatga gcacttttaa agttctgcta tgtggcgcgg tattatcccg | 840 |
| tattgacgcc gggcaagagc aactcggtcg ccgcatacac tattctcaga atgacttggt | 900 |
| tgagtactca ccagtcacag aaaagcatct tacggatggc atgacagtaa gagaattatg | 960 |
| cagtgctgcc ataaccatga gtgataacac tgcggccaac ttacttctga caacgatcgg | 1020 |
| aggaccgaag gagctaaccg cttttttgca acatggggg gatcatgtaa ctcgccttga | 1080 |
| tcgttgggaa ccggagctga atgaagccat accaaacgac gagcgtgaca ccacgatgcc | 1140 |
| tgcagcaatg gcaacaacgt tgcgcaaact attaactggc gaactactta ctctagcttc | 1200 |
| ccggcaacaa ttaatagact ggatggaggc ggataaagtt gcaggaccac ttctgcgctc | 1260 |
| ggcccttccg gctggctggt ttattgctga taaatctgga gccggtgagc gtgggtctcg | 1320 |
| cggtatcatt gcagcactgg ggccagatgg taagccctcc cgtatcgtag ttatctacac | 1380 |
| gacgggagt caggcaacta tggatgaacg aaatagacag atcgctgaga taggtgcctc | 1440 |
| actgattaag cattggtaac tgtcagacca gtttactca tatatacttt agattgattt | 1500 |
| aaaacttcat ttttaattta aaaggatcta ggtgaagatc ctttttgata atctcatgac | 1560 |
| caaaatccct taacgtgagt tttcgttcca ctgagcgtca gaccccgtag aaaagatcaa | 1620 |
| aggatcttct tgagatcctt ttttctgcg cgtaatctgc tgcttgcaaa caaaaaaacc | 1680 |
| accgctacca gcggtggttt gtttgccgga tcaagagcta ccaactcttt ttccgaaggt | 1740 |
| aactggcttc agcagagcgc agataccaaa tactgtcctt ctagtgtagc cgtagttagg | 1800 |
| ccaccacttc aagaactctg tagcaccgcc tacatacctc gctctgctaa tcctgttacc | 1860 |
| agtggctgct gccagtggcg ataagtcgtg tcttaccggg ttggactcaa gacgatagtt | 1920 |
| accggataag gcgcagcggt cgggctgaac ggggggttcg tgcacacagc ccagcttgga | 1980 |
| gcgaacgacc tacaccgaac tgagatacct acagcgtgag ctatgagaaa gcgccacgct | 2040 |
| tcccgaaggg agaaaggcgg acaggtatcc ggtaagcggc agggtcggaa caggagagcg | 2100 |
| cacgagggag cttccagggg gaaacgcctg gtatctttat agtcctgtcg ggtttcgcca | 2160 |

-continued

```
cctctgactt gagcgtcgat ttttgtgatg ctcgtcaggg gggcggagcc tatggaaaaa     2220
cgccagcaac gcggccttttt tacggttcct ggccttttgc tggccttttg ctcacatgtt    2280
```

```
cctctgactt gagcgtcgat ttttgtgatg ctcgtcaggg gggcggagcc tatggaaaaa     2220
cgccagcaac gcggccttttt tacggttcct ggccttttgc tggccttttg ctcacatgtt    2280
ctttcctgcg ttatccctg  attctgtgga taaccgtatt accgcctttg agtgagctga     2340
taccgctcgc cgcagccgaa cgaccgagcg cagcgagtca gtgagcgagg aagcggaaga     2400
gcgcctgatg cggtattttc tccttacgca tctgtgcggt atttcacacc gcatatatgg     2460
tgcactctca gtacaatctg ctctgatgcc gcatagttaa gccagtatac actccgctat     2520
cgctacgtga ctgggtcatg gctgcgcccc gacacccgcc aacacccgct gacgcgccct     2580
gacgggcttg tctgctcccg gcatccgctt acagacaagc tgtgaccgtc tccgggagct     2640
gcatgtgtca gaggttttca ccgtcatcac cgaaacgcgc gaggcagctg cggtaaagct     2700
catcagcgtg gtcgtgaagc gattcacaga tgtctgcctg ttcatccgcg tccagctcgt     2760
tgagtttctc cagaagcgtt aatgtctggc ttctgataaa gcgggccatg ttaagggcgg     2820
tttttttcctg tttggtcact gatgcctccg tgtaaggggg atttctgttc atggggggtaa  2880
tgataccgat gaaacgagag aggatgctca cgatacgggt tactgatgat gaacatgccc     2940
ggttactgga acgttgtgag ggtaaacaac tggcggtatg gatgcggcgg gaccagagaa     3000
aaatcactca gggtcaatgc cagcgcttcg ttaatacaga tgtaggtgtt ccacagggta     3060
gccagcagca tcctgcgatg cagatccgga acataatggt gcagggcgct gacttccgcg     3120
tttccagact ttacgaaaca cggaaaccga agaccattca tgttgttgct caggtcgcag     3180
acgttttgca gcagcagtcg cttcacgttc gctcgcgtat cggtgattca ttctgctaac     3240
cagtaaggca accccgccag cctagccggg tcctcaacga caggagcacg atcatgcgca     3300
cccgtggcca ggacccaacg ctgcccgaga tctcgatccc gcgaaattaa tacgactcac     3360
tatagggaga ccacaacggt ttccctctag aaataattttt gtttaacttt aagaaggaga   3420
```

| | | | | |
|---|---|---|---|---|
| tatacat atg agt gca aaa ggc ata gac tac gat aag ctc att gtt cgg | | | | 3469 |
| Met Ser Ala Lys Gly Ile Asp Tyr Asp Lys Leu Ile Val Arg | | | | |
| 1 5 10 | | | | |

```
ttt gga agt agt aaa att gac aaa gag cta ata aac cga ata gag aga       3517
Phe Gly Ser Ser Lys Ile Asp Lys Glu Leu Ile Asn Arg Ile Glu Arg
 15              20                  25                  30 gcc acc ggc caa aga cca cac cac ttc ctg cgc aga ggc atc ttc ttc       3565
Ala Thr Gly Gln Arg Pro His His Phe Leu Arg Arg Gly Ile Phe Phe
             35                  40                  45 tca cac aga gat atg aat cag gtt ctt gat gcc tat gaa aat aag aag       3613
Ser His Arg Asp Met Asn Gln Val Leu Asp Ala Tyr Glu Asn Lys Lys
         50                  55                  60 cca ttt tat ctg tac acg ggc cgg ggc ccc tct tct gaa gca atg cat       3661
Pro Phe Tyr Leu Tyr Thr Gly Arg Gly Pro Ser Ser Glu Ala Met His
     65                  70                  75 gta ggt cac ctc att cca ttt att ttc aca aag tgg ctc cag gat gta       3709
Val Gly His Leu Ile Pro Phe Ile Phe Thr Lys Trp Leu Gln Asp Val
 80                  85                  90 ttt aac gtg ccc ttg gtc atc cag atg acg gat gac gag aag tat ctg       3757
Phe Asn Val Pro Leu Val Ile Gln Met Thr Asp Asp Glu Lys Tyr Leu
 95                  100                 105                 110 tgg aag gac ctg acc ctg gac cag gcc tat ggc gat gct gtt gag aat       3805
Trp Lys Asp Leu Thr Leu Asp Gln Ala Tyr Gly Asp Ala Val Glu Asn
                 115                 120                 125 gcc aag gac atc atc gcc tgt ggc ttt gac atc aac aag act ttc ata       3853
Ala Lys Asp Ile Ile Ala Cys Gly Phe Asp Ile Asn Lys Thr Phe Ile
             130                 135                 140
```

```
ttc tct gac ctg gac tac atg ggg atg agc tca ggt ttc tac aaa aat      3901
Phe Ser Asp Leu Asp Tyr Met Gly Met Ser Ser Gly Phe Tyr Lys Asn
        145                 150                 155 gtg gtg aag att caa aag cat gtt acc ttc aac caa gtg aaa ggc att      3949
Val Val Lys Ile Gln Lys His Val Thr Phe Asn Gln Val Lys Gly Ile
160                 165                 170 ttc ggc ttc act gac agc gac tgc att ggg aag atc agt ttt cct gcc      3997
Phe Gly Phe Thr Asp Ser Asp Cys Ile Gly Lys Ile Ser Phe Pro Ala
175                 180                 185                 190 atc cag gct gct ccc tcc ttc agc aac tca ttc cca cag atc ttc cga      4045
Ile Gln Ala Ala Pro Ser Phe Ser Asn Ser Phe Pro Gln Ile Phe Arg
                195                 200                 205 gac agg acg gat atc cag tgc ctt atc cca tgt gcc att gac cag gat      4093
Asp Arg Thr Asp Ile Gln Cys Leu Ile Pro Cys Ala Ile Asp Gln Asp
            210                 215                 220 cct tac ttt aga atg aca agg gac gtc gcc ccc agg atc ggc tat cct      4141
Pro Tyr Phe Arg Met Thr Arg Asp Val Ala Pro Arg Ile Gly Tyr Pro
        225                 230                 235 aaa cca gcc ctg ttg cac tcc acc ttc ttc cca gcc ctg cag ggc gcc      4189
Lys Pro Ala Leu Leu His Ser Thr Phe Phe Pro Ala Leu Gln Gly Ala
    240                 245                 250 cag acc aaa atg agt gcc agc gac cca aac tcc tcc atc ttc ctc acc      4237
Gln Thr Lys Met Ser Ala Ser Asp Pro Asn Ser Ser Ile Phe Leu Thr
255                 260                 265                 270 gac acg gcc aag cag atc aaa acc aag gtc aat aag cat gcg ttt tct      4285
Asp Thr Ala Lys Gln Ile Lys Thr Lys Val Asn Lys His Ala Phe Ser
                275                 280                 285 gga ggg aga gac acc atc gag gag cac agg cag ttt ggg ggc aac tgt      4333
Gly Gly Arg Asp Thr Ile Glu Glu His Arg Gln Phe Gly Gly Asn Cys
            290                 295                 300 gat gtg gac gtg tct ttc atg tac ctg acc ttc ttc ctc gag gac gac      4381
Asp Val Asp Val Ser Phe Met Tyr Leu Thr Phe Phe Leu Glu Asp Asp
        305                 310                 315 gac aag ctc gag cag atc agg aag gat tac acc agc gga gcc atg ctc      4429
Asp Lys Leu Glu Gln Ile Arg Lys Asp Tyr Thr Ser Gly Ala Met Leu
    320                 325                 330 acc ggt gag ctc aag aag gca ctc ata gag gtt ctg cag ccc ttg atc      4477
Thr Gly Glu Leu Lys Lys Ala Leu Ile Glu Val Leu Gln Pro Leu Ile
335                 340                 345                 350 gca gag cac cag gcc cgg cgc aag gag gtc acg gat gag ata gtg aaa      4525
Ala Glu His Gln Ala Arg Arg Lys Glu Val Thr Asp Glu Ile Val Lys
                355                 360                 365 gag ttc atg act ccc cgg aag ctg tcc ttc gac ttt cag aag ctt gcg      4573
Glu Phe Met Thr Pro Arg Lys Leu Ser Phe Asp Phe Gln Lys Leu Ala
            370                 375                 380 gcc gca ctc gag cac cac cac cac cac cac tgagatccgg ctgctaacaa       4623
Ala Ala Leu Glu His His His His His His
        385                 390 agcccgaaag gaagctgagt tggctgctgc caccgctgag caataactag cataacccct      4683
tggggcctct aaacgggtct tgaggggttt tttgctgaaa ggaggaacta tatccggat       4742

<210> SEQ ID NO 16
<211> LENGTH: 392
<212> TYPE: PRT
<213> ORGANISM: Artificial Sequence
<220> FEATURE:
<223> OTHER INFORMATION: Description of Artificial Sequence: human
      inactive TrpRS in pET20B

<400> SEQUENCE: 16
```

```
Met Ser Ala Lys Gly Ile Asp Tyr Asp Lys Leu Ile Val Arg Phe Gly
  1               5                  10                  15

Ser Ser Lys Ile Asp Lys Glu Leu Ile Asn Arg Ile Glu Arg Ala Thr
             20                  25                  30

Gly Gln Arg Pro His His Phe Leu Arg Arg Gly Ile Phe Phe Ser His
         35                  40                  45

Arg Asp Met Asn Gln Val Leu Asp Ala Tyr Glu Asn Lys Lys Pro Phe
     50                  55                  60

Tyr Leu Tyr Thr Gly Arg Gly Pro Ser Ser Glu Ala Met His Val Gly
 65                  70                  75                  80

His Leu Ile Pro Phe Ile Phe Thr Lys Trp Leu Gln Asp Val Phe Asn
                 85                  90                  95

Val Pro Leu Val Ile Gln Met Thr Asp Asp Glu Lys Tyr Leu Trp Lys
            100                 105                 110

Asp Leu Thr Leu Asp Gln Ala Tyr Gly Asp Ala Val Glu Asn Ala Lys
            115                 120                 125

Asp Ile Ile Ala Cys Gly Phe Asp Ile Asn Lys Thr Phe Ile Phe Ser
        130                 135                 140

Asp Leu Asp Tyr Met Gly Met Ser Ser Gly Phe Tyr Lys Asn Val Val
145                 150                 155                 160

Lys Ile Gln Lys His Val Thr Phe Asn Gln Val Lys Gly Ile Phe Gly
                165                 170                 175

Phe Thr Asp Ser Asp Cys Ile Gly Lys Ile Ser Phe Pro Ala Ile Gln
            180                 185                 190

Ala Ala Pro Ser Phe Ser Asn Ser Phe Pro Gln Ile Phe Arg Asp Arg
        195                 200                 205

Thr Asp Ile Gln Cys Leu Ile Pro Cys Ala Ile Asp Gln Asp Pro Tyr
    210                 215                 220

Phe Arg Met Thr Arg Asp Val Ala Pro Arg Ile Gly Tyr Pro Lys Pro
225                 230                 235                 240

Ala Leu Leu His Ser Thr Phe Phe Pro Ala Leu Gln Gly Ala Gln Thr
                245                 250                 255

Lys Met Ser Ala Ser Asp Pro Asn Ser Ser Ile Phe Leu Thr Asp Thr
            260                 265                 270

Ala Lys Gln Ile Lys Thr Lys Val Asn Lys His Ala Phe Ser Gly Gly
        275                 280                 285

Arg Asp Thr Ile Glu Glu His Arg Gln Phe Gly Gly Asn Cys Asp Val
    290                 295                 300

Asp Val Ser Phe Met Tyr Leu Thr Phe Phe Leu Glu Asp Asp Asp Lys
305                 310                 315                 320

Leu Glu Gln Ile Arg Lys Asp Tyr Thr Ser Gly Ala Met Leu Thr Gly
                325                 330                 335

Glu Leu Lys Lys Ala Leu Ile Glu Val Leu Gln Pro Leu Ile Ala Glu
            340                 345                 350

His Gln Ala Arg Arg Lys Glu Val Thr Asp Glu Ile Val Lys Glu Phe
        355                 360                 365

Met Thr Pro Arg Lys Leu Ser Phe Asp Phe Gln Lys Leu Ala Ala Ala
    370                 375                 380

Leu Glu His His His His His His
385                 390

<210> SEQ ID NO 17
<211> LENGTH: 6
<212> TYPE: PRT
```

<213> ORGANISM: Homo sapiens

<400> SEQUENCE: 17

Glu Leu Arg Val Ser Tyr
 1               5

<210> SEQ ID NO 18
<211> LENGTH: 6
<212> TYPE: PRT
<213> ORGANISM: Escherichia coli

<400> SEQUENCE: 18

Glu Thr Val Gln Glu Trp
 1               5

<210> SEQ ID NO 19
<211> LENGTH: 9
<212> TYPE: PRT
<213> ORGANISM: Homo sapiens

<400> SEQUENCE: 19

Ser Ala Lys Glu Leu Arg Cys Gln Cys
 1               5

<210> SEQ ID NO 20
<211> LENGTH: 11
<212> TYPE: PRT
<213> ORGANISM: Homo sapiens

<400> SEQUENCE: 20

Ala Ser Val Ala Thr Glu Leu Arg Cys Gln Cys
 1               5                   10

<210> SEQ ID NO 21
<211> LENGTH: 7
<212> TYPE: PRT
<213> ORGANISM: Homo sapiens

<400> SEQUENCE: 21

Ala Glu Leu Arg Cys Gln Cys
 1               5

<210> SEQ ID NO 22
<211> LENGTH: 58
<212> TYPE: PRT
<213> ORGANISM: Homo sapiens

<400> SEQUENCE: 22

Gly Asp Glu Lys Lys Ala Lys Glu Lys Ile Glu Lys Lys Gly Glu Lys
 1               5                   10                  15

Lys Glu Lys Lys Gln Gln Ser Ile Ala Gly Ser Ala Asp Ser Lys Pro
                20                  25                  30

Ile Asp Val Ser Arg Leu Asp Leu Arg Ile Gly Cys Ile Ile Thr Ala
                35                  40                  45

Arg Lys His Pro Asp Ala Asp Ser Leu Tyr
        50                  55

<210> SEQ ID NO 23
<211> LENGTH: 58
<212> TYPE: PRT
<213> ORGANISM: Homo sapiens

<400> SEQUENCE: 23

```
Pro Ala Leu Lys Lys Leu Ala Ser Ala Ala Tyr Pro Asp Pro Ser Lys
1               5                   10                  15

Gln Lys Pro Met Ala Lys Gly Pro Ala Lys Asn Ser Glu Pro Glu Glu
                20                  25                  30

Val Ile Pro Ser Arg Leu Asp Ile Arg Val Gly Lys Ile Ile Thr Val
            35                  40                  45

Glu Lys His Pro Asp Ala Asp Ser Leu Tyr
    50                  55
```

<210> SEQ ID NO 24
<211> LENGTH: 7
<212> TYPE: PRT
<213> ORGANISM: Homo sapiens

<400> SEQUENCE: 24

```
Arg Val Gly Lys Ile Ile Thr
1               5
```

<210> SEQ ID NO 25
<211> LENGTH: 7
<212> TYPE: PRT
<213> ORGANISM: Homo sapiens

<400> SEQUENCE: 25

```
Arg Ile Gly Cys Ile Ile Thr
1               5
```

<210> SEQ ID NO 26
<211> LENGTH: 7
<212> TYPE: PRT
<213> ORGANISM: Homo sapiens

<400> SEQUENCE: 26

```
Arg Ile Gly Arg Ile Ile Thr
1               5
```

<210> SEQ ID NO 27
<211> LENGTH: 7
<212> TYPE: PRT
<213> ORGANISM: Caenorhabditis elegans

<400> SEQUENCE: 27

```
Arg Val Gly Arg Ile Ile Lys
1               5
```

<210> SEQ ID NO 28
<211> LENGTH: 7
<212> TYPE: PRT
<213> ORGANISM: Saccharomyces cerevisiae

<400> SEQUENCE: 28

```
Arg Val Gly Phe Ile Gln Lys
1               5
```

<210> SEQ ID NO 29
<211> LENGTH: 7
<212> TYPE: PRT
<213> ORGANISM: Bos taurus

<400> SEQUENCE: 29

```
Arg Val Gly Lys Val Ile Ser
1               5
```

```
<210> SEQ ID NO 30
<211> LENGTH: 7
<212> TYPE: PRT
<213> ORGANISM: Mus musculus

<400> SEQUENCE: 30

Arg Ile Gly Cys Ile Val Thr
1               5

<210> SEQ ID NO 31
<211> LENGTH: 7
<212> TYPE: PRT
<213> ORGANISM: Mesocricetus auratus

<400> SEQUENCE: 31

Arg Ile Gly Arg Ile Val Thr
1               5

<210> SEQ ID NO 32
<211> LENGTH: 7
<212> TYPE: PRT
<213> ORGANISM: Ovis aries

<400> SEQUENCE: 32

Arg Ile Gly Cys Ile Ile Thr
1               5

<210> SEQ ID NO 33
<211> LENGTH: 7
<212> TYPE: PRT
<213> ORGANISM: Calcarea sp.

<400> SEQUENCE: 33

Arg Ile Gly Arg Ile Thr Ser
1               5

<210> SEQ ID NO 34
<211> LENGTH: 7
<212> TYPE: PRT
<213> ORGANISM: A. aeolicus

<400> SEQUENCE: 34

Arg Val Ala Lys Val Leu Ser
1               5

<210> SEQ ID NO 35
<211> LENGTH: 7
<212> TYPE: PRT
<213> ORGANISM: Escherichia coli

<400> SEQUENCE: 35

Arg Val Gly Lys Ile Val Glu
1               5

<210> SEQ ID NO 36
<211> LENGTH: 7
<212> TYPE: PRT
<213> ORGANISM: Escherichia coli

<400> SEQUENCE: 36

Arg Val Ala Leu Ile Glu Asn
1               5

<210> SEQ ID NO 37
<211> LENGTH: 7
```

```
<212> TYPE: PRT
<213> ORGANISM: Haemophilus influenzae

<400> SEQUENCE: 37

Arg Val Ala Lys Val Leu Lys
  1               5

<210> SEQ ID NO 38
<211> LENGTH: 7
<212> TYPE: PRT
<213> ORGANISM: Bacillus subtilis

<400> SEQUENCE: 38

Arg Val Ala Glu Val Ile Glu
  1               5

<210> SEQ ID NO 39
<211> LENGTH: 7
<212> TYPE: PRT
<213> ORGANISM: B. stearothermophilus

<400> SEQUENCE: 39

Arg Val Ala Glu Val Val Gln
  1               5

<210> SEQ ID NO 40
<211> LENGTH: 7
<212> TYPE: PRT
<213> ORGANISM: Thermus thermophilus

<400> SEQUENCE: 40

Arg Val Ala Glu Val Leu Ala
  1               5

<210> SEQ ID NO 41
<211> LENGTH: 6
<212> TYPE: PRT
<213> ORGANISM: Escherichia coli

<400> SEQUENCE: 41

Val Gly Glu Val Val Glu
  1               5

<210> SEQ ID NO 42
<211> LENGTH: 6
<212> TYPE: PRT
<213> ORGANISM: Bacillus subtilis

<400> SEQUENCE: 42

Ile Gly His Val Leu Glu
  1               5

<210> SEQ ID NO 43
<211> LENGTH: 6
<212> TYPE: PRT
<213> ORGANISM: Synechococcus sp.

<400> SEQUENCE: 43

Val Gly Arg Val Leu Glu
  1               5

<210> SEQ ID NO 44
<211> LENGTH: 6
<212> TYPE: PRT
<213> ORGANISM: Thermus thermophilus
```

<400> SEQUENCE: 44

Phe Ala Arg Val Leu Glu
 1               5

<210> SEQ ID NO 45
<211> LENGTH: 85
<212> TYPE: PRT
<213> ORGANISM: Homo sapiens

<400> SEQUENCE: 45

Met Ser Tyr Lys Ala Ala Gly Glu Asp Tyr Lys Ala Asp Cys Pro
 1               5                  10                  15

Pro Gly Asn Pro Ala Pro Thr Ser Asn His Gly Pro Asp Ala Thr Glu
                20                  25                  30

Ala Glu Glu Asp Phe Val Asp Pro Trp Thr Val Gln Thr Ser Ser Ala
            35                  40                  45

Lys Gly Ile Asp Tyr Asp Lys Leu Ile Val Arg Phe Gly Ser Ser Lys
        50                  55                  60

Ile Asp Lys Glu Leu Ile Asn Arg Ile Glu Arg Ala Thr Gly Gln Arg
 65                  70                  75                  80

Pro His His Phe Leu
                85

<210> SEQ ID NO 46
<211> LENGTH: 85
<212> TYPE: PRT
<213> ORGANISM: Bos taurus

<400> SEQUENCE: 46

Thr Ser Tyr Lys Ala Ala Thr Gly Glu Asp Tyr Lys Val Asp Cys Pro
 1               5                  10                  15

Pro Gly Asp Pro Ala Pro Glu Ser Gly Glu Gly Leu Asp Ala Thr Glu
                20                  25                  30

Ala Asp Glu Asp Phe Val Asp Pro Trp Thr Val Gln Thr Ser Ser Ala
            35                  40                  45

Lys Gly Ile Asp Tyr Asp Lys Leu Ile Val Arg Phe Gly Ser Ser Lys
        50                  55                  60

Ile Asp Lys Glu Leu Val Asn Arg Ile Glu Arg Ala Thr Gly Gln Arg
 65                  70                  75                  80

Pro His Arg Phe Leu
                85

<210> SEQ ID NO 47
<211> LENGTH: 85
<212> TYPE: PRT
<213> ORGANISM: Mus musculus

<400> SEQUENCE: 47

Met Ser Tyr Lys Ala Ala Met Gly Glu Glu Tyr Lys Ala Gly Cys Pro
 1               5                  10                  15

Pro Gly Asn Pro Thr Ala Gly Arg Asn Cys Asp Ser Asp Ala Thr Lys
                20                  25                  30

Ala Ser Glu Asp Phe Val Asp Pro Trp Thr Val Arg Thr Ser Ser Ala
            35                  40                  45

Lys Gly Ile Asp Tyr Asp Lys Leu Ile Val Gln Pro Gly Ser Ser Lys
        50                  55                  60

Ile Asp Lys Glu Leu Ile Asn Arg Ile Glu Arg Ala Thr Gly Gln Arg

```
                65                  70                  75                  80

Pro His Arg Phe Leu
                85

<210> SEQ ID NO 48
<211> LENGTH: 85
<212> TYPE: PRT
<213> ORGANISM: Oryctolagus cuniculus

<400> SEQUENCE: 48

Thr Ser Tyr Lys Glu Ala Met Gly Glu Asp Tyr Lys Ala Asp Cys Pro
  1               5                  10                  15

Pro Gly Asn Ser Thr Pro Asp Ser His Gly Pro Asp Glu Ala Val Asp
                 20                  25                  30

Asp Lys Glu Asp Phe Val Asp Pro Trp Thr Val Arg Thr Ser Ser Ala
             35                  40                  45

Lys Gly Ile Asp Tyr Asp Lys Leu Ile Val Gln Phe Gly Ser Ser Lys
         50                  55                  60

Ile Asp Lys Glu Leu Val Asn Arg Ile Glu Arg Ala Thr Gly Gln Arg
 65                  70                  75                  80

Pro His Arg Phe Leu
                85

<210> SEQ ID NO 49
<211> LENGTH: 86
<212> TYPE: PRT
<213> ORGANISM: Homo sapiens

<400> SEQUENCE: 49

Ile Ser Tyr Gln Gly Arg Ile Pro Tyr Pro Arg Pro Gly Thr Cys Pro
  1               5                  10                  15

Gly Gly Ala Phe Thr Pro Asn Met Arg Thr Thr Lys Glu Phe Pro Asp
                 20                  25                  30

Asp Val Val Thr Phe Ile Arg Asn His Pro Leu Met Tyr Asn Ser Ile
             35                  40                  45

Tyr Pro Ile His Lys Arg Pro Leu Ile Val Arg Ile Gly Thr Asp Tyr
         50                  55                  60

Lys Tyr Thr Lys Ile Ala Val Asp Arg Val Asn Ala Ala Asp Gly Arg
 65                  70                  75                  80

Tyr His Val Leu Phe Leu
                85

<210> SEQ ID NO 50
<211> LENGTH: 86
<212> TYPE: PRT
<213> ORGANISM: Mus musculus

<400> SEQUENCE: 50

Ile Ser Tyr Gln Gly Arg Ile Pro Tyr Pro Arg Pro Gly Thr Cys Pro
  1               5                  10                  15

Gly Gly Ala Phe Thr Pro Asn Met Arg Thr Thr Lys Asp Phe Pro Asp
                 20                  25                  30

Asp Val Val Thr Phe Ile Arg Asn His Pro Leu Met Tyr Asn Ser Ile
             35                  40                  45

Ser Pro Ile His Arg Arg Pro Leu Ile Val Arg Ile Gly Thr Asp Tyr
         50                  55                  60

Lys Tyr Thr Lys Ile Ala Val Asp Arg Val Asn Ala Ala Asp Gly Arg
 65                  70                  75                  80
```

Tyr His Val Leu Phe Leu
                85

<210> SEQ ID NO 51
<211> LENGTH: 46
<212> TYPE: PRT
<213> ORGANISM: Homo sapiens

<400> SEQUENCE: 51

Ala Ala Ala Gly Glu Asp Tyr Lys Ala Asp Cys Pro Pro Gly Asn Pro
 1               5                  10                  15

Ala Pro Thr Ser Asn His Gly Pro Asp Ala Thr Glu Ala Glu Glu Asp
            20                  25                  30

Phe Val Asp Pro Trp Thr Val Gln Thr Ser Ser Ala Lys Gly
        35                  40                  45

<210> SEQ ID NO 52
<211> LENGTH: 46
<212> TYPE: PRT
<213> ORGANISM: Bos taurus

<400> SEQUENCE: 52

Ala Ala Thr Gly Glu Asp Tyr Lys Val Asp Cys Pro Pro Gly Asp Pro
 1               5                  10                  15

Ala Pro Glu Ser Gly Glu Gly Leu Asp Ala Thr Glu Ala Asp Glu Asp
            20                  25                  30

Phe Val Asp Pro Trp Thr Val Gln Thr Ser Ser Ala Lys Gly
        35                  40                  45

<210> SEQ ID NO 53
<211> LENGTH: 46
<212> TYPE: PRT
<213> ORGANISM: Mus musculus

<400> SEQUENCE: 53

Ala Ala Met Gly Glu Glu Tyr Lys Ala Gly Cys Pro Pro Gly Asn Pro
 1               5                  10                  15

Thr Ala Gly Arg Asn Cys Asp Ser Asp Ala Thr Lys Ala Ser Glu Asp
            20                  25                  30

Phe Val Asp Pro Trp Thr Val Arg Thr Ser Ser Ala Lys Gly
        35                  40                  45

<210> SEQ ID NO 54
<211> LENGTH: 46
<212> TYPE: PRT
<213> ORGANISM: Oryctolagus cuniculus

<400> SEQUENCE: 54

Glu Ala Met Gly Glu Asp Tyr Lys Ala Asp Cys Pro Pro Gly Asn Ser
 1               5                  10                  15

Thr Pro Asp Ser His Gly Pro Asp Glu Ala Val Asp Lys Glu Asp
            20                  25                  30

Phe Val Asp Pro Trp Thr Val Arg Thr Ser Ser Ala Lys Gly
        35                  40                  45

<210> SEQ ID NO 55
<211> LENGTH: 41
<212> TYPE: PRT
<213> ORGANISM: Mus musculus

<400> SEQUENCE: 55

```
Ala Phe Ala Gly Glu Asp Phe Lys Val Asp Ile Pro Glu Thr His Gly
1               5                   10                  15

Gly Glu Gly Thr Glu Asp Glu Ile Asp Asp Glu Tyr Glu Gly Asp Trp
                20                  25                  30

Ser Asn Ser Ser Ser Ser Thr Ser Gly
            35                  40
```

```
<210> SEQ ID NO 56
<211> LENGTH: 5
<212> TYPE: PRT
<213> ORGANISM: Homo sapiens

<400> SEQUENCE: 56

Met Gly Asp Ala Pro
1               5

<210> SEQ ID NO 57
<211> LENGTH: 5
<212> TYPE: PRT
<213> ORGANISM: Homo sapiens

<400> SEQUENCE: 57

Ser Asn His Gly Pro
1               5

<210> SEQ ID NO 58
<211> LENGTH: 5
<212> TYPE: PRT
<213> ORGANISM: Homo sapiens

<400> SEQUENCE: 58

Ser Ala Lys Gly Ile
1               5
```

HUMAN AMINOACYL-TRNA SYNTHETASE POLYPEPTIDES USEFUL FOR THE REGULATION OF ANGIOGENESIS

CROSS-REFERENCE TO RELATED APPLICATIONS

This is a division of U.S. patent application Ser. No. 10/240,532, filed on Sep. 30, 2002, now U.S. Pat. No. 7,067, 126, which is the National Stage of PCT/US01/08975, filed on Mar. 21, 2001, which claims the benefit of U.S. Provisional Application Ser. No. 60/193,471, filed on Mar. 31, 2000, the disclosures of which are incorporated herein by reference.

GOVERNMENTAL RIGHTS

This invention was made with governmental support from the United States Government, National Institutes of Health, Grant GM23562; the United States Government has certain rights in the invention.

FIELD OF THE INVENTION

The invention relates to compositions comprising truncated tRNA synthetase polypeptides, as well as nucleic acids encoding such truncated tRNA synthetase polypeptides. Methods of making and using such compositions are also disclosed.

BACKGROUND OF THE INVENTION

Aminoacyl-tRNA synthetases, which catalyze the aminoacylation of tRNA molecules, are ancient proteins that are essential for decoding genetic information during the process of translation. In higher eukaryotes, nine aminoacyl-tRNA synthetases associate with at least three other polypeptides to form a supramolecular multienzyme complex (Mirande et al., 1985, *Eur. J. Biochem.* 147:281-89). Each of the eukaryotic tRNA synthetases consists of a core enzyme, which is closely related to the prokaryotic counterpart of the tRNA synthetase, and an additional domain that is appended to the amino-terminal or carboxyl-terminal end of the core enzyme (Mirande, 1991, *Prog. Nucleic Acid Res. Mol. Biol.* 40:95-142). Human tyrosyl-tRNA synthetase (TyrRS), for example, has a carboxyl-terminal domain that is not part of prokaryotic and lower eukaryotic TyrRS molecules (FIG. 1) (Rho et al., 1998, *J. Biol. Chem.* 273:11267-73). It has also been suggested that both the bovine and rabbit TyrRS molecules possess an extra domain (Kleeman et al., 1997, *J. Biol. Chem.* 272:14420-25).

In most cases, the appended domains appear to contribute to the assembly of the multienzyme complex (Mirande, supra). However, the presence of an extra domain is not strictly correlated with the association of a synthetase into the multienzyme complex. Higher eukaryotic TyrRS, for example, is not a component of the multienzyme complex (Mirande et al., supra).

The carboxyl-terminal domain of human TyrRS shares a 51% sequence identity with the mature form of human endothelial monocyte-activating polypeptide II (EMAP II) (Rho et al., supra). TyrRS is the only higher eukaryotic aminoacyl-tRNA synthetase known to contain an EMAP II-like domain. The EMAP-like domain of TyrRS has been shown to be dispensable for aminoacylation in vitro and in yeast (Wakasugi et al., 1998, *EMBO J.* 17:297-305).

EMAP II is a proinflammatory cytokine that was initially identified as a product of murine methylcholanthrene A-induced fibrosarcoma cells. Pro-EMAP II is cleaved and is secreted from apoptotic cells to produce a biologically active 22-kD mature cytokine (Kao, et al., 1994, *J. Biol. Chem.* 269:25106-19). The mature EMAP II can induce migration of mononuclear phagocytes (MPs) and polymorphonuclear leukocytes (PMNs); it also stimulates the production of tumor necrosis factor-α (TNF α) and tissue factor by MPs and the release of myeloperoxidase from PMNs.

The catalytic core domain of tryptophanyl-tRNA synthetase (TrpRS) is a close homolog of the catalytic domain of TyrRS (Brown et al., 1997, *J. Mol. Evol.* 45:9-12). As shown in FIG. 15, mammalian TrpRS molecules have an amino-terminal appended domain. In normal human cells, two forms of TrpRS can be detected: a major form consisting of the full-length molecule and a minor truncated form ("mini TrpRS"). The minor form is generated by the deletion of the amino-terminal domain through alternative splicing of the pre-mRNA (Tolstrup et al., 1995, *J. Biol. Chem.* 270:397-403). The amino-terminus of mini TrpRS has been determined to be the met residue at position 48 of the full-length TrpRS molecule (id.). Alternatively, truncated TrpRS may be generated by proteolysis (Lemaire et al., 1975, *Eur. J. Biochem.* 51:237-52). For example, bovine TrpRS is highly expressed in the pancreas and is secreted into the pancreatic juice (Kisselev, 1993, *Biochimie* 75:1027-39), thus resulting in the production of a truncated TrpRS molecule. These results suggest that truncated TrpRS has a function other than the aminoacylation of tRNA (Kisselev, supra).

Angiogenesis, or the proliferation of new capillaries from pre-existing blood vessels, is a fundamental process necessary for embryonic development, subsequent growth, and tissue repair. Angiogenesis is a prerequisite for the development and differentiation of the vascular tree, as well as for a wide variety of fundamental physiological processes including embryogenesis, somatic growth, tissue and organ repair and regeneration, cyclical growth of the corpus luteum and endometrium, and development and differentiation of the nervous system. In the female reproductive system, angiogenesis occurs in the follicle during its development, in the corpus luteum following ovulation and in the placenta to establish and maintain pregnancy. Angiogenesis additionally occurs as part of the body's repair processes, e.g. in the healing of wounds and fractures. Angiogenesis is also a factor in tumor growth, since a tumor must continuously stimulate growth of new capillary blood vessels in order to grow. Angiogenesis is an essential part of the growth of human solid cancer, and abnormal angiogenesis is associated with other diseases such as rheumatoid arthritis, psoriasis, and diabetic retinopathy (Folkman, J. and Klagsbrun, M., *Science* 235: 442-447,(1987)). Several factors are involved in angiogenesis. Both acidic and basic fibroblast growth factor molecules that are mitogens for endothelial cells and other cell types. Angiotropin and angiogenin can induce angiogenesis, although their functions are unclear (Folkman, J., 1993, *Cancer Medicine* pp. 153-170, Lea and Febiger Press). A highly selective mitogen for vascular endothelial cells is vascular endothelial growth factor or VEGF (Ferrara, N., et al., *Endocr. Rev.* 13:19-32, (1992)).

SUMMARY OF THE INVENTION

The invention provides novel truncated tRNA synthetase polypeptides having chemokine activity that are useful for research, diagnostic, prognostic and therapeutic applications. In one embodiment, the tRNA synthetase polypeptides are useful for regulating vascular endothelial cell function, and in particular, for regulating angiogenesis.

In one embodiment, the novel truncated tRNA synthetase polypeptides comprise a Rossmann fold nucleotide binding domain wherein the isolated polypeptide is capable of regulating vascular endothelial cell function. In one embodiment, the truncated tRNA synthetase polypeptide is a tyrosyl-tRNA synthetase with a carboxyl-terminal truncation. In another embodiment, the truncated tRNA synthetase polypeptide is a tryptophanyl-tRNA synthetase, preferably at least about 46 kilodaltons in size, with an amino-terminal truncation.

Both angiogenic and angiostatic truncated tRNA synthetase polypeptides are provided by the present invention.

In one embodiment, preferred truncated tRNA synthetase polypeptides include a polypeptide consisting essentially of amino acid residues 1-364 of SEQ ID NO:2; a polypeptide consisting essentially of amino acid residues 1-343 of SEQ ID NO:2; a polypeptide of approximately 40 kD molecular weight produced by cleavage of the polypeptide of SEQ ID NO:2 with polymorphonuclear leucocyte elastase; and fragments thereof comprising the amino acid sequence -Glu-Leu-Arg-Val-Ser-Tyr-.

In another embodiment, preferred truncated tRNA synthetase polypeptides include a polypeptide consisting essentially of amino acid residues 48-471 of SEQ ID NO:10; a polypeptide consisting essentially of amino acid residues 71-471 of SEQ ID NO:10; a polypeptide of approximately 47 kD molecular weight produced by cleavage of the polypeptide of SEQ ID NO:10 with polymorphonuclear leucocyte elastase; and fragments thereof comprising the amino acid sequence -Asp-Leu-Thr-. In one preferred embodiment, the truncated tRNA synthetase polypeptide is mammalian, and more preferably, human.

In another embodiment, the invention comprises an isolated nucleic acid molecule comprising a polynucleotide having a nucleotide sequence at least 95% identical to a sequence selected from the group consisting of a polynucleotide of SEQ ID NO:1 or SEQ ID NO: 9; a polynucleotide which is hybridizable to a polynucleotide of SEQ ID NO:1 or SEQ ID NO: 9; a polynucleotide encoding the polypeptide of SEQ ID NO:2 or SEQ ID NO: 10; a polynucleotide encoding a polypeptide epitope of SEQ ID NO:2 or SEQ ID NO: 10 and a polynucleotide that is hybridizable to a polynucleotide encoding a polypeptide epitope of SEQ ID NO:2 or SEQ ID NO:10. In a preferred embodiment the invention comprises a recombinant expression vector comprising the isolated nucleic acid molecule of encoding a tRNA synthetase polypeptide. Another embodiment is a host cell comprising a recombinant expression vector comprising the isolated nucleic acid molecule of SEQ ID NO:1 or SEQ ID NO:9 encoding a tRNA synthetase polypeptide.

In one embodiment, the present invention is a process for making tRNA synthetase polypeptides by treating tyrosyl-tRNA synthetase with a protease. In one embodiment, the present invention is a process for making tRNA synthetase polypeptides by treating tryptophanyl-tRNA synthetase with a protease. One preferred protease is polymorphonuclear leukocyte elastase.

The invention provides compositions comprising tRNA synthetase polypeptides and a pharmaceutically suitable excipient. Such compositions are suitable for transdermal, transmucosal, enteral or parenteral administration. In another embodiment, the tRNA synthetase polypeptide can be used for the preparation of a pharmaceutical composition for transdermal, transmucosal, enteral or parenteral administration.

In one embodiment, the tRNA synthetase polypeptide can have angiogenic activity at least two-fold greater than control levels. In embodiments in which the tRNA synthetase polypeptide has angiostatic activity, the polypeptide suppresses at least ten percent of angiogenic activity, more preferably at least ninety percent of angiogenic activity.

The invention further provides a method of enhancing angiogenesis in a mammal comprising the step of administering an angiogenically effective amount of a composition comprising a angiogenic tRNA synthetase polypeptide and a pharmaceutically suitable excipient.

The invention further provides a method of suppressing angiogenesis in a mammal comprising the step of administering an angiostatically effective amount of a composition comprising an angiostatic tRNA synthetase polypeptide and a pharmaceutically suitable excipient.

In another embodiment, the invention provides a method of enhancing angiogenesis to a graft in a mammal comprising the step of administering an angiogenically effective amount of a composition comprising an angiogenic tRNA synthetase polypeptide and a pharmaceutically suitable excipient.

In another embodiment, the invention provides a method of treating myocardial infarction in a mammal comprising the step of administering an angiogenically effective amount of a composition comprising an angiogenic tRNA synthetase polypeptide and a pharmaceutically suitable excipient.

In another embodiment, the invention provides a method of treating a condition that would benefit from increased angiogenesis in a mammal comprising the step of administering an angiogenically effective amount of a composition comprising an angiogenic tRNA synthetase polypeptide and a pharmaceutically suitable excipient.

In another embodiment, the invention provides a method of treating a condition that would benefit from decreased angiogenesis in a mammal comprising the step of administering an angiostatically effective amount of the composition comprising an angiostatic tRNA synthetase polypeptide and a pharmaceutically suitable excipient.

In another embodiment, the invention provides a method of treating a solid tumor in a mammal comprising the step of administering an angiostatically effective amount of the composition comprising an angiostatic tRNA synthetase polypeptide and a pharmaceutically suitable excipient.

In another embodiment, the invention provides a method of suppressing tumor metatasis in a mammal comprising the step of administering an angiostatically effective amount of the composition comprising an angiostatic tRNA synthetase polypeptide and a pharmaceutically suitable excipient.

DETAILED DESCRIPTION OF THE PREFERRED EMBODIMENTS

Figure 1:
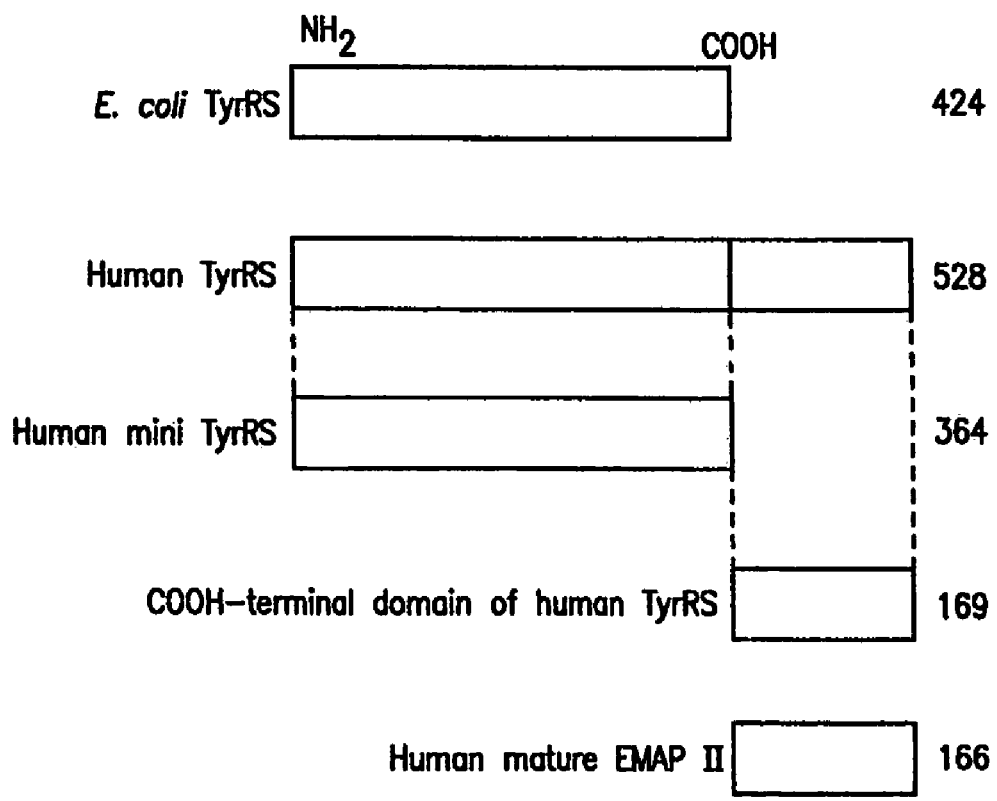
FIG. 1 illustrates a schematic alignment of *E. coli* TyrRS, human full-length TyrRS, human mini TyrRS, the human TyrRS carboxyl-terminal domain, and human mature EMAP II.

In order to facilitate understanding of the following examples, certain frequently occurring methods and/or terms will be described.

The term "tRNA synthetase polypeptides" means polypeptides that are shorter than the corresponding full length tRNA synthetase.

As used herein the term "cell culture" encompasses both the culture medium and the cultured cells. As used herein the phrase "isolating a polypeptide from the cell culture" encompasses isolating a soluble or secreted polypeptide from the culture medium as well as isolating an integral membrane protein from the cultured cells.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µL of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a poly-acrylamide gel to isolate the desired fragment. "Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

As used herein "angiogenic TyrRS peptides" refers to fragments of TyrRS having angiogenic activity, including, but not limited to, mini TyrRS, fragments, analogs and derivatives thereof comprising the amino acid sequence ELR.

As used herein, "TyrRS angiogenic therapy" refers to the delivery of an angiogenic effective amount of mini TyrRS or fragments thereof as well as to the delivery of polynucleotides encoding an angiogenic effective amount of mini TyrRS or fragments thereof.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in SEQ ID NO:1 or in SEQ ID NO:9 or may be a different coding sequence which coding sequence, as a result of the redundancy or degeneracy of the genetic code, encodes the same, mature polypeptide sequence shown in SEQ ID NO:2 or in SEQ ID NO:10.

Thus, the term "polynucleotide encoding a polypeptide" encompasses a polynucleotide which includes only coding sequence for the polypeptide as well as a polynucleotide which includes additional coding and/or non-coding sequence. The present invention further relates to variants of the hereinabove described polynucleotides which encode for fragments, analogs and derivatives of the polypeptide having the amino acid sequence of SEQ ID NO:2 or SEQ ID NO:10 or the polypeptide encoded by the cDNA of SEQ ID NO:1 or SEQ ID NO:9. The variant of the polynucleotide may be a naturally occurring allelic variant of the polynucleotide or a non-naturally occurring variant of the polynucleotide. Thus, the present invention includes polynucleotides encoding the same mature polypeptide as shown of SEQ ID NO:2 or SEQ ID NO:10 or the same mature polypeptide encoded by the cDNA of SEQ ID NO:1 or SEQ ID NO:9 as well as variants of such polynucleotides which variants encode for an fragment, derivative or analog of the polypeptide of SEQ ID NO:2 or SEQ ID NO:10 or the polypeptide encoded by SEQ ID NO:1 or SEQ ID NO:9. Such nucleotide variants include deletion variants, substitution variants and addition or insertion variants.

As hereinabove indicated, the polynucleotide may have a coding sequence which is a naturally occurring allelic variant of the coding sequence shown in SEQ ID NO:1 or SEQ ID NO:9. As known in the art, an allelic variant is an alternate form of a polynucleotide sequence which have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains. Thus, for example, the polynucleotide of the present invention may encode for a mature protein, or for a protein having a prosequence or for a protein having both a prosequence and presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of SEQ ID NO:1 or SEQ ID NO:9.

The terms "fragment," "derivative" and "analog" when referring to the polypeptide or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of SEQ ID NO:2 or SEQ ID NO:10 or that encoded by the polynucleotide of SEQ ID NO:1 or SEQ ID NO:9 may be (I) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the tRNA synthetase polpeptide genes. The culture conditions, such as temperature, pH and the like, are those previously used with the host cell selected for expression, and will be apparent to the ordinarily skilled artisan.

The polynucleotide of the present invention may be employed for producing a polypeptide by recombinant techniques. Thus, for example, the polynucleotide sequence may be included in any one of a variety of expression vehicles, in particular vectors or plasmids for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. A preferred vector is pET20b. However, any other plasmid or vector may be used as long as it is replicable and viable in the host.

As hereinabove described, the appropriate DNA sequence may be inserted into the vector by a variety of procedures. In general, the DNA sequence is inserted into an appropriate restriction endonuclease sites by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.$ $coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as herein above described, as well as an appropriate promoter or control sequence, may be employed to transform an appropriate host to permit the host to express the protein. As representative examples of appropriate hosts, there may be mentioned: bacterial cells, such as $E.$ $coli,$ $Salmonella$ $typhimurium,$ $Streptomyces$; fungal cells, such as yeast; insect cells, such as $Drosophila$ and Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE-9 (Qiagen), pBs, phagescript, PsiX174, pBluescript SK, pBsKS, pNH8a, pNH16a, pNH18a, pNH46a (Stratagene); pTrc99A, pKK223-3, pKK233-3, pDR540, PRIT5 (Pharmacia). Eukaryotic: pWLneo, pSV2cat, pOG44, pXT1, pSG (Stratagene) pSVK3, pBPV, PMSG, pSVL (Pharmacia) and pET20B. In one preferred embodiment, the vector is pET20B. However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, PL and Trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., $Basic$ $Methods$ $in$ $Molecular$ $Biology,$ 1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook. et al., $Molecular$ $Cloning.$ $A$ $Laboratory$ $Manual$, Second Edition, (Cold Spring Harbor, N.Y., 1989), the disclosure of which is hereby incorporated by reference. Transcription of a DNA encoding the polypeptides of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Following transformation of a suitable host strain and growth of the host strain to an appropriate cell density, the selected promoter is derepressed by appropriate means (e.g., temperature shift or chemical induction) and cells are cultured for an additional period.

Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

Polypeptides are recovered and purified from recombinant cell cultures by methods used heretofore, including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. It is preferred to have low concentrations (approximately 0.1-5 mM) of calcium ion present during purification (Price, et al., J. Biol. Chem., 244:917 (1969)). Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture).

Depending upon the host employed in a recombinant production procedure, the polypeptides of the present invention may be glycosylated with mammalian or other eukaryotic carbohydrates or may be non-glycosylated.

The polypeptides of the present invention may be modified to improve stability and increase potency by means known in the art. For example, L-amino acids can be replaced by D-amino acids, the amino terminus can be acetylated, or the carboxyl terminus modified, e.g., ethylamine-capped (Dawson, D. W., et al., Mol. Pharmacol., 55: 332-338 (1999)).

Angiogenic tRNA synthetase polypeptides are useful as wound healing agents, particularly where it is necessary to re-vascularize damaged tissues, or where new capillary angiogenesis is important. Therefore, it may be used for treatment of full-thickness wounds such as dermal ulcers, including pressure sores, venous ulcers, and diabetic ulcers. In addition, it can be used in the treatment of full-thickness burns and injuries where angiogenesis is desired to prepare the burn in injured sites for a skin graft and flap. In this case, it should be applied directly at the sites. Similarly angiogenic tRNA synthetase polypeptides polypeptides can be used in plastic surgery when reconstruction is required following a burn, other trauma, or even for cosmetic purposes.

Since angiogenesis is important in keeping wounds clean and non-infected, angiogenic tRNA synthetase polypeptides may be used in association with surgery and following the repair of cuts. It should be particularly useful in the treatment of abdominal wounds where there is a high risk of infection.

Angiogenic tRNA synthetase polypeptides can be used for the promotion of endothelialization in vascular graft surgery. In the case of vascular grafts using either transplanted or synthetic material, angiogenic TyrRS peptides can be applied to the surface of the graft, preferably in a pharmaceutically appropriate excipient. In one embodiment, the pharmaceutically appropriate excipient further provides for the continuous release of angiogenic TyrRS peptides.

Angiogenic tRNA synthetase therapy can be used to repair the damage of myocardial infarction. In one preferred embodiment, angiogenic TyrRS therapy can be used in conjunction with coronary bypass surgery by stimulating the growth of the transplanted tissue. In one preferred embodiment, angiogenic tRNA synthetase therapy can be administered by direct myocardial injection of angiogenic tRNA synthetase polypeptides or polynucleotides encoding angiogenic tRNA synthetase polypeptides. See Losodo, D. W., et al., Circulation, 98: 2800-2804 (1998).

In another embodiment, angiogenic tRNA synthetase therapy can be used in conjunction with angiography to administer the angiogenic tRNA synthetase polypeptides or polynucleotides encoding angiogenic tRNA synthetase polypeptides directly to the lumen and wall of the blood vessel.

Similarly, tRNA synthetase therapy can be used to administer the angiogenic or angiostatic tRNA synthetase polypeptides or polynucleotides encoding angiogenic or angiostatic tRNA synthetase polypeptides directly to the lumen and wall of other hollow organs, such as the uterus.

The polypeptide of the present invention may also be employed in accordance with the present invention by expression of such polypeptide in vivo, which is often referred to as "gene therapy."

Thus, for example, cells such as bone marrow cells may be engineered with a polynucleotide (DNA or RNA) encoding for the polypeptide ex vivo, the engineered cells are then provided to a patient to be treated with the polypeptide. Such methods are well-known in the art. For example, cells may be engineered by procedures known in the art by use of a retroviral particle containing RNA encoding for the polypeptide of the present invention. Similarly, cells may be engineered in vivo for expression of the polypeptide in vivo, for example, by procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such methods should be apparent to those skilled in the art from the teachings of the present invention. For example, the expression vehicle for engineering cells may be other than a retroviral particle, for example, an adenovirus, which may be used to engineering cells in vivo after combination with a suitable delivery vehicle.

Various viral vectors that can be utilized for gene therapy as taught herein include adenovirus, herpes virus, vaccinia, adeno-associated virus (AAV), or, preferably, an RNA virus such as a retrovirus. Preferably, the retroviral vector is a derivative of a murine or avian retrovirus, or is a lentiviral vector. The preferred retroviral vector is a lentiviral vector. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of additional retroviral vectors can incorporate multiple genes. All of these vectors can transfer or incorporate a gene for a selectable marker so that transduced cells can be identified and generated. By inserting a zinc finger derived-DNA binding polypeptide sequence of interest into the viral vector, along with another gene that encodes the ligand for a receptor on a specific target cell, for example, the vector is made target specific. Retroviral vectors can be made target specific by inserting, for example, a polynucleotide encoding a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the zinc finger-nucleotide binding protein polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to $\psi$2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

Another targeted delivery system for polynucleotides encoding zinc finger derived-DNA binding polypeptides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome.

Liposomes are artificial membrane vesicles which are useful as delivery vehicles in vitro and in vivo. It has been shown that large unilamellar vesicles (LUV), which range in size from 0.2-4.0 $\mu$m can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system will be ligands and receptors which will allow the targeted delivery system to find and "home in" on the desired cells. A ligand may be any compound of interest which will bind to another compound, such as a receptor.

In general, surface membrane proteins which bind to specific effector molecules are referred to as receptors. In the present invention, antibodies are preferred receptors. Antibodies can be used to target liposomes to specific cell-surface ligands. For example, certain antigens expressed specifically on tumor cells, referred to as tumor-associated antigens (TAAs), may be exploited for the purpose of targeting antibody-zinc finger-nucleotide binding protein-containing liposomes directly to the malignant tumor. Since the zinc finger-nucleotide binding protein gene product may be indiscriminate with respect to cell type in its action, a targeted delivery system offers a significant improvement over randomly injecting non-specific liposomes. A number of procedures can be used to covalently attach either polyclonal or monoclonal antibodies to a liposome bilayer. Antibody-targeted liposomes can include monoclonal or polyclonal antibodies or fragments thereof such as Fab, or F(ab')$_2$, as long as they bind efficiently to an the antigenic epitope on the target cells. Liposomes may also be targeted to cells expressing receptors for hormones or other serum factors.

There are available to one skilled in the art multiple viral and non-viral methods suitable for introduction of a nucleic acid molecule into a target cell. Genetic manipulation of primary tumor cells has been described previously (Patel et al., 1994). Genetic modification of a cell may be accomplished using one or more techniques well known in the gene therapy field (*Human Gene Therapy*, April 1994, Vol. 5, p. 543-563; Mulligan, R. C. 1993). Viral transduction methods may comprise the use of a recombinant DNA or an RNA virus comprising a nucleic acid sequence that drives or inhibits expression of a protein having sialyltransferase activity to infect a target cell. A suitable DNA virus for use in the present invention includes but is not limited to an adenovirus (Ad), adeno-associated virus (AAV), herpes virus, vaccinia virus or a polio virus. A suitable RNA virus for use in the present invention includes but is not limited to a retrovirus or Sindbis virus. It is to be understood by those skilled in the art that several such DNA and RNA viruses exist that may be suitable for use in the present invention.

Adenoviral vectors have proven especially useful for gene transfer into eukaryotic cells (Stratford-Perricaudet and Perricaudet. 1991). Adenoviral vectors have been successfully utilized to study eukaryotic gene expression (Levrero, M., et al. 1991). vaccine development (Graham and Prevec, 1992), and in animal models (Stratford-Perricaudet, et al. 1992.; Rich, et al. 1993). The first trial of Ad-mediated gene therapy in human was the transfer of the cystic fibrosis transmembrane conductance regulator (CFTR) gene to lung (Crystal, et al., 1994). Experimental routes for administrating recombinant Ad to different tissues in vivo have included intratracheal instillation (Rosenfeld, et al. 1992) injection into muscle (Quantin, B., et al. 1992), peripheral intravenous injection (Herz and Gerard, 1993) and stereotactic inoculation to brain (Le Gal La Salle, et al. 1993). The adenoviral vector, then, is widely available to one skilled in the art and is suitable for use in the present invention.

Adeno-associated virus (AAV) has recently been introduced as a gene transfer system with potential applications in gene therapy. Wild-type AAV demonstrates high-level infectivity, broad host range and specificity in integrating into the host cell genome (Hermonat and Muzyczka. 1984). Herpes simplex virus type-1 (HSV-1) is attractive as a vector system, especially for use in the nervous system because of its neurotropic property (Geller and Federoff. 1991; Glorioso, et al. 1995). Vaccinia virus, of the poxvirus family, has also been developed as an expression vector (Smith and Moss, 1983; Moss, 1992). Each of the above-described vectors are widely available to one skilled in the art and would be suitable for use in the present invention.

Retroviral vectors are capable of infecting a large percentage of the target cells and integrating into the cell genome (Miller and Rosman. 1989). Retroviruses were developed as gene transfer vectors relatively earlier than other viruses, and were first used successfully for gene marking and transducing the cDNA of adenosine deaminase (ADA) into human lymphocytes. Preferred retroviruses include lentiviruses. In preferred embodiments, the retrovirus is selected from the group consisting of HIV, BIV and SIV.

"Non-viral" delivery techniques that have been used or proposed for gene therapy include DNA-ligand complexes, adenovirus-ligand-DNA complexes, direct injection of DNA, $CaPO_4$ precipitation, gene gun techniques, electroporation, liposomes and lipofection (Mulligan, 1993). Any of these methods are widely available to one skilled in the art and would be suitable for use in the present invention. Other suitable methods are available to one skilled in the art, and it is to be understood that the present invention may be accomplished using any of the available methods of transfection. Several such methodologies have been utilized by those skilled in the art with varying success (Mulligan, R. 1993). Lipofection may be accomplished by encapsulating an isolated DNA molecule within a liposomal particle and contacting the liposomal particle with the cell membrane of the target cell. Liposomes are self-assembling, colloidal particles in which a lipid bilayer, composed of amphiphilic molecules such as phosphatidyl serine or phosphatidyl choline, encapsulates a portion of the surrounding media such that the lipid bilayer surrounds a hydrophilic interior. Unilammellar or multilammellar liposomes can be constructed such that the interior contains a desired chemical, drug, or, as in the instant invention, an isolated DNA molecule.

The cells may be transfected in vivo, ex vivo, or in vitro. The cells may be transfected as primary cells isolated from a patient or a cell line derived from primary cells, and are not necessarily autologous to the patient to whom the cells are ultimately administered. Following ex vivo or in vitro transfection, the cells may be implanted into a host. Genetic manipulation of primary tumor cells has been described previously (Patel et al. 1994). Genetic modification of the cells may be accomplished using one or more techniques well known in the gene therapy field (*Human Gene Therapy*. April 1994. Vol. 5, p. 543-563; Mulligan, R. C. 1993).

In order to obtain transcription of the nucleic acid of the present invention within a target cell, a transcriptional regulatory region capable of driving gene expression in the target cell is utilized. The transcriptional regulatory region may comprise a promoter, enhancer, silencer or repressor element and is functionally associated with a nucleic acid of the present invention. Preferably, the transcriptional regulatory region drives high level gene expression in the target cell. Transcriptional regulatory regions suitable for use in the present invention include but are not limited to the human cytomegalovirus (CMV) immediate-early enhancer/promoter, the SV40 early enhancer/promoter, the JC polyomavirus promoter, the albumin promoter, PGK and the α-actin promoter coupled to the CMV enhancer (Doll, et al 1996).

The vectors of the present invention may be constructed using standard recombinant techniques widely available to one skilled in the art. Such techniques may be found in common molecular biology references such as *Molecular Cloning: A Laboratory Manual* (Sambrook, et al., 1989, Cold Spring Harbor Laboratory Press), *Gene Expression Technology* (*Methods in Enzymology*, Vol. 185, edited by D. Goeddel, 1991. Academic Press, San Diego, Calif.), and *PCR Protocols: A Guide to Methods and Applications* (Innis, et al. 1990. Academic Press, San Diego, Calif.).

Administration of a nucleic acid of the present invention to a target cell in vivo may be accomplished using any of a variety of techniques well known to those skilled in the art.

The vectors of the present invention may be administered orally, parenterally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally. Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The dosage regimen for treating a disorder or a disease with the vectors of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods.

The pharmaceutically active compounds (i.e., vectors) of this invention can be processed in accordance with conventional methods of pharmacy to produce medicinal agents for administration to patients, including humans and other mammals. For oral administration, the pharmaceutical composition may be in the form of, for example, a capsule, a tablet, a suspension, or liquid. The pharmaceutical composition is preferably made in the form of a dosage unit containing a given amount of DNA or viral vector particles (collectively referred to as "vector"). For example, these may contain an amount of vector from about $10^3$-$10^{15}$ viral particles, preferably from about $10^6$-$10^{12}$ viral particles. A suitable daily dose for a human or other mammal may vary widely depending on the condition of the patient and other factors, but, once again, can be determined using routine methods. The vector may also be administered by injection as a composition with suitable carriers including saline, dextrose, or water.

While the nucleic acids and/or vectors of the invention can be administered as the sole active pharmaceutical agent, they can also be used in combination with one or more vectors of the invention or other agents. When administered as a combination, the therapeutic agents can be formulated as separate compositions that are given at the same time or different times, or the therapeutic agents can be given as a single composition.

The polypeptide of the present invention may be employed in combination with a suitable pharmaceutical carrier. Such compositions comprise a therapeutically effective amount of the protein, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptide of the present invention may be employed on conjunction with other therapeutic compounds.

The pharmaceutical compositions may be administered in a convenient manner, such as the transdermal, transmucosal, enteral and parenteral intravenous routes. The amounts and dosage regimens of tRNA synthetase polypeptides administered to a subject will depend on a number of factors, such as the mode of administration, the nature of the condition being treated, the body weight of the subject being treated and the judgment of the prescribing physician. Generally speaking, it is given, for example, in therapeutically effective doses of at least about 10 μg/kg body weight and, in most cases, it would be administered in an amount not in excess of about 8 mg/kg body weight per day and preferably the dosage is from about 10 μg/kg body weight to about 1 μg/kg body weight daily, taking into the account the routes of administration, symptoms, etc.

The present invention is further directed to inhibiting tRNA synthetase polypeptides in vivo by the use of antisense technology. Antisense technology can be used to control gene expression through triple-helix formation or antisense DNA or RNA, both of which methods are based on binding of a polynucleotide to DNA or RNA. For example, the 5' coding portion of the mature polynucleotide sequence, which encodes for the polypeptide of the present invention, is used to design an antisense RNA oligonucleotide of from 10 to 40 base pairs in length. A DNA oligonucleotide is designed to be complementary to a region of the gene involved in transcription (triple helix—see Lee et al., *Nucl. Acids Res.,* 6:3073 (1979); Cooney et al., *Science,* 241:456 (1988); and Dervan et al., *Science,* 251: 1360 (1991), thereby preventing transcription and the production of VEGF2. The antisense RNA oligonucleotide hybridizes to the mRNA in vivo and blocks translation of an mRNA molecule into the tRNA synthetase polypeptides (Okano, *J. Neurochem.,* 56:560 (1991); *Oligodeoxynucleotides as Antisense Inhibitors of Gene Expression,* CRC Press, Boca Raton, Fla. (1988)).

Alternatively, the oligonucleotides described above can be delivered to cells by procedures in the art such that the antisense RNA or DNA may be expressed in vivo to inhibit production of tRNA synthetase polypeptides in the manner described above. Antisense constructs to tRNA synthetase polypeptides, therefore, may inhibit the activity of the tRNA synthetase polypeptides and prevent the further growth or even regress solid tumors, since angiogenesis and neovascularization are essential steps in solid tumor growth. These antisense constructs may also be used to treat rheumatoid arthritis, psoriasis and diabetic retinopathy which are all characterized by abnormal angiogenesis.

Alternatively, angiostatic TrpRS therapy can be used to oppose the oppose the angiogenic activity of endogenous and exogenous angiogenic factors, including TyrRS polypeptides, and to prevent the further growth or even regress solid tumors, since angiogenesis and neovascularization are essential steps in solid tumor growth. Such therapies can also be used to treat rheumatoid arthritis, psoriasis and diabetic retinopathy which are all characterized by abnormal angiogenesis.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptide corresponding to a sequence of the present invention can be obtained by direct injection of the polypeptide into an animal or by administering the polypeptide to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, *Nature,* 256:495-497), the trioma technique, the human B-cell hybridoma technique (Kozbor et al., 1983, *Immunology Today* 4:72), and the EBV-hybridoma technique to produce human monoclonal antibodies (Cole, et al., 1985, in *Monoclonal Antibodies and Cancer Therapy,* Alan R. Liss, Inc., pp. 77-96).

Techniques described for the production of single chain antibodies (U.S. Pat. No. 4,946,778) can be adapted to produce single chain antibodies to immunogenic polypeptide products of this invention.

Neutralization antibodies can be identified and applied to mask the activity of tRNA synthetase polypeptides. The utility of such an approach has been shown in mice model systems against VEGF. VEGF2 can also be inactivated by certain dominant negative mutants within the gene itself. It is known that both PDGF α and β form either heterodimers or homodimers, and VEGF forms homodimers. These antibodies therefore may be used to block endogenous angiogenic activity and retard the growth of solid tumors. These antibodies may also be used to treat inflammation caused by the increased vascular permeability. These antibodies may further be used in an immunoassay to detect the presence of tumors in certain individuals. Enzyme immunoassay can be performed from the blood sample of an individual.

The present invention is also directed to antagonist/inhibitors of the polypeptides of the present invention. The antagonist/inhibitors are those which inhibit or eliminate the function of the polypeptide. Thus, for example, antagonists bind to a polypeptide of the present invention and inhibit or eliminate its function. The antagonist, for example, could be an antibody against the polypeptide which binds to the polypeptide or, in some cases, an oligonucleotide. An example of an inhibitor is a small molecule which binds to and occupies the catalytic site of the polypeptide thereby making the catalytic site inaccessible to substrate such that normal biological activity is prevented. Examples of small molecules include but are not limited to small peptides or peptide-like molecules.

Alternatively, antagonists to the polypeptides of the present invention may be employed which bind to the receptors to which a polypeptide of the present invention normally binds. The antagonists may be closely related proteins such that they recognize and bind to the receptor sites of the natural protein, however, they are inactive forms of the natural protein and thereby prevent the action of the normal polypeptide ligand. The antagonist/inhibitors may be used therapeutically as an anti-tumor drug by occupying the receptor sites of tumors. The antagonist/inhibitors may also be used to prevent inflammation. The antagonist/inhibitors may also be used to treat solid tumor growth, diabetic retinopathy, psoriasis and rheumatoid arthritis. The antagonist/inhibitors may be employed in a composition with a pharmaceutically acceptable carrier, e.g., as hereinabove described.

These and other aspects of the present invention should be apparent to those skilled in the art from the teachings herein.

Also preferred is a method for diagnosing in a subject a pathological condition associated with abnormal structure or expression of a gene, which method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of a nucleotide sequence of SEQ ID NO:1 and SEQ ID NO:9.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:1 and SEQ ID NO:9. The nucleic acid molecules can comprise DNA molecules or RNA molecules.

Further preferred is a method for detecting in a biological sample a polypeptide comprising an amino acid sequence which is at least 90% identical to a sequence of at least 10 contiguous amino acids in a sequence selected from the group consisting of amino acid sequences of SEQ ID NO:2 and SEQ ID NO:10, which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing in a subject a pathological condition associated with abnormal structure or expression of a gene, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of amino acid sequences of SEQ ID NO:2 and SEQ ID NO:10.

The present invention also includes a diagnostic system, preferably in kit form, for assaying for the presence of the polypeptide of the present invention in a body sample, such brain tissue, cell suspensions or tissue sections; or a body fluid sample, such as CSF, blood, plasma or serum, where it is desirable to detect the presence, and preferably the amount, of the polypeptide of this invention in the sample according to the diagnostic methods described herein.

In a related embodiment, a nucleic acid molecule can be used as a probe (i.e., an oligonucleotide) to detect the presence of a polynucleotide of the present invention, a gene corresponding to a polynucleotide of the present invention, or a mRNA in a cell that is diagnostic for the presence or expression of a polypeptide of the present invention in the cell. The nucleic acid molecule probes can be of a variety of lengths from at least about 10, suitably about 10 to about 5000 nucleotides long, although they will typically be about 20 to 500 nucleotides in length. Hybridization methods are extremely well known in the art and will not be described further here.

In a related embodiment, detection of genes corresponding to the polynucleotides of the present invention can be conducted by primer extension reactions such as the polymerase chain reaction (PCR). To that end, PCR primers are utilized in pairs, as is well known, based on the nucleotide sequence of the gene to be detected. Preferably, the nucleotide sequence is a portion of the nucleotide sequence of a polynucleotide of the present invention. Particularly preferred PCR primers can be derived from any portion of a DNA sequence encoding a polypeptide of the present invention, but are preferentially from regions which are not conserved in other cellular proteins.

Preferred PCR primer pairs useful for detecting the genes corresponding to the polynucleotides of the present invention and expression of these genes are described in the Examples, including the corresponding Tables. Nucleotide primers from the corresponding region of the polypeptides of the present invention described herein are readily prepared and used as PCR primers for detection of the presence or expression of the corresponding gene in any of a variety of tissues.

The present invention also provides a screening assay for antiangiogenic compounds. As disclosed herein, antiangiogenic compounds, such as TrpRS polypeptides, can be detected by their ability to oppose the angiogenic effects of TyrRS polypeptides on model systems such as chick allantoic membrane (CAM), and corneal vascularization models.

The diagnostic system includes, in an amount sufficient to perform at least one assay, a subject polypeptide of the present invention, a subject antibody or monoclonal antibody, and/or a subject nucleic acid molecule probe of the present invention, as a separately packaged reagent.

In another embodiment, a diagnostic system, preferably in kit form, is contemplated for assaying for the presence of the polypeptide of the present invention or an antibody immunoreactive with the polypeptide of the present invention in a body fluid sample. Such diagnostic kit would be useful for monitoring the fate of a therapeutically administered polypeptide of the present invention or an antibody immunoreactive with the polypeptide of the present invention. The system includes, in an amount sufficient for at least one assay, a polypeptide of the present invention and/or a subject antibody as a separately packaged immunochemical reagent.

Instructions for use of the packaged reagent(s) are also typically included.

As used herein, the term "package" refers to a solid matrix or material such as glass, plastic (e.g., polyethylene, polypropylene or polycarbonate), paper, foil and the like capable of holding within fixed limits a polypeptide, polyclonal antibody, or monoclonal antibody of the present invention. Thus, for example, a package can be a glass vial used to contain milligram quantities of a contemplated polypeptide or antibody or it can be a microtiter plate well to which microgram quantities of a contemplated polypeptide or antibody have been operatively affixed (i.e., linked) so as to be capable of being immunologically bound by an antibody or antigen, respectively.

"Instructions for use" typically include a tangible expression describing the reagent concentration or at least one assay method parameter, such as the relative amounts of reagent and sample to be admixed, maintenance time periods for reagent/sample admixtures, temperature, buffer conditions and the like.

A diagnostic system of the present invention preferably also includes a label or indicating means capable of signaling the formation of an immunocomplex containing a polypeptide or antibody molecule of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyanate (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in Antibody As a Tool, Marchalonis et al., Eds., John Wiley & Sons, Ltd., pp. 189-231 (1982), which is incorporated herein by reference. Other suitable labeling agents are known to those skilled in the art.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-amino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}$I, $^{125}$I, $^{128}$I, $^{132}$I and $^{51}$Cr represent one class of gamma ray emission-producing radioactive element indicating groups. Particularly preferred is $^{125}$I. Another group of useful labeling means are those elements such as $^{11}$C, $^{18}$F, $^{15}$O and $^{13}$N which themselves emit positrons. The positrons so emitted produce gamma rays upon encounters with electrons present in the animal's body. Also useful is a beta emitter, such $^{111}$indium or $^{3}$H.

The linking of labels or labeling of polypeptides and proteins is well known in the art. For instance, antibody molecules produced by a hybridoma can be labeled by metabolic incorporation of radioisotope-containing amino acids provided as a component in the culture medium (see, e.g., Galfre et al., *Meth. Enzymol.*, 73:3-46 (1981)). The techniques of protein conjugation or coupling through activated functional groups are particularly applicable (see, for example, Aurameas, et al., *Scand. J. Immunol.*, Vol. 8 Suppl. 7:7-23 (1978); Rodwell et al., *Biotech.*, 3:889-894 (1984); and U.S. Pat. No. 4,493,795).

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, *S. aureus* protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the quantity of the polypeptide of the present invention in a sample. "ELISA" refers to an enzyme-linked immunosorbent assay that employs an antibody or antigen bound to a solid phase and an enzyme-antigen or enzyme-antibody conjugate to detect and quantify the amount of an antigen present in a sample. A description of the ELISA technique is found in Sites et al., *Basic and Clinical Immunology*, 4$^{th}$ Ed., Chap. 22, Lange Medical Publications, Los Altos, Calif. (1982) and in U.S. Pat. Nos. 3,654,090; 3,850,752; and 4,016,043, which are all incorporated herein by reference.

Thus, in some embodiments, a polypeptide of the present invention, an antibody or a monoclonal antibody of the present invention can be affixed to a solid matrix to form a solid support that comprises a package in the subject diagnostic systems.

A reagent is typically affixed to a solid matrix by adsorption from an aqueous medium, although other modes of affixation applicable to proteins and polypeptides can be used that are well known to those skilled in the art. Exemplary adsorption methods are described herein.

Useful solid matrices are also well known in the art. Such materials are water insoluble and include the cross-linked dextran available under the trademark SEPHADEX from Pharmacia Fine Chemicals (Piscataway, N.J.), agarose; polystyrene beads of ut 1 micron (µm) to about 5 millimeters (mm) in diameter available from several suppliers (e.g., Abbott Laboratories, Chicago, Ill.), polyvinyl chloride, polystyrene, cross-linked polyacrylamide, nitrocellulose- or nylon-based webs (sheets, strips or paddles) or tubes, plates or the wells of a microtiter plate, such as those made from polystyrene or polyvinylchloride.

The reagent species, labeled specific binding agent, or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems.

The preferred embodiment of the present invention is best understood by referring to FIGS. 1-25 and Examples 1 -18. The Examples, which follow, are illustrative of specific embodiments of the invention, and various uses thereof. They are set forth for explanatory purposes only, and are not to be taken as limiting the invention.

EXAMPLE 1

Preparation of Endotoxin-Free Recombinant TyrRS and TrpRS

Figure 15:
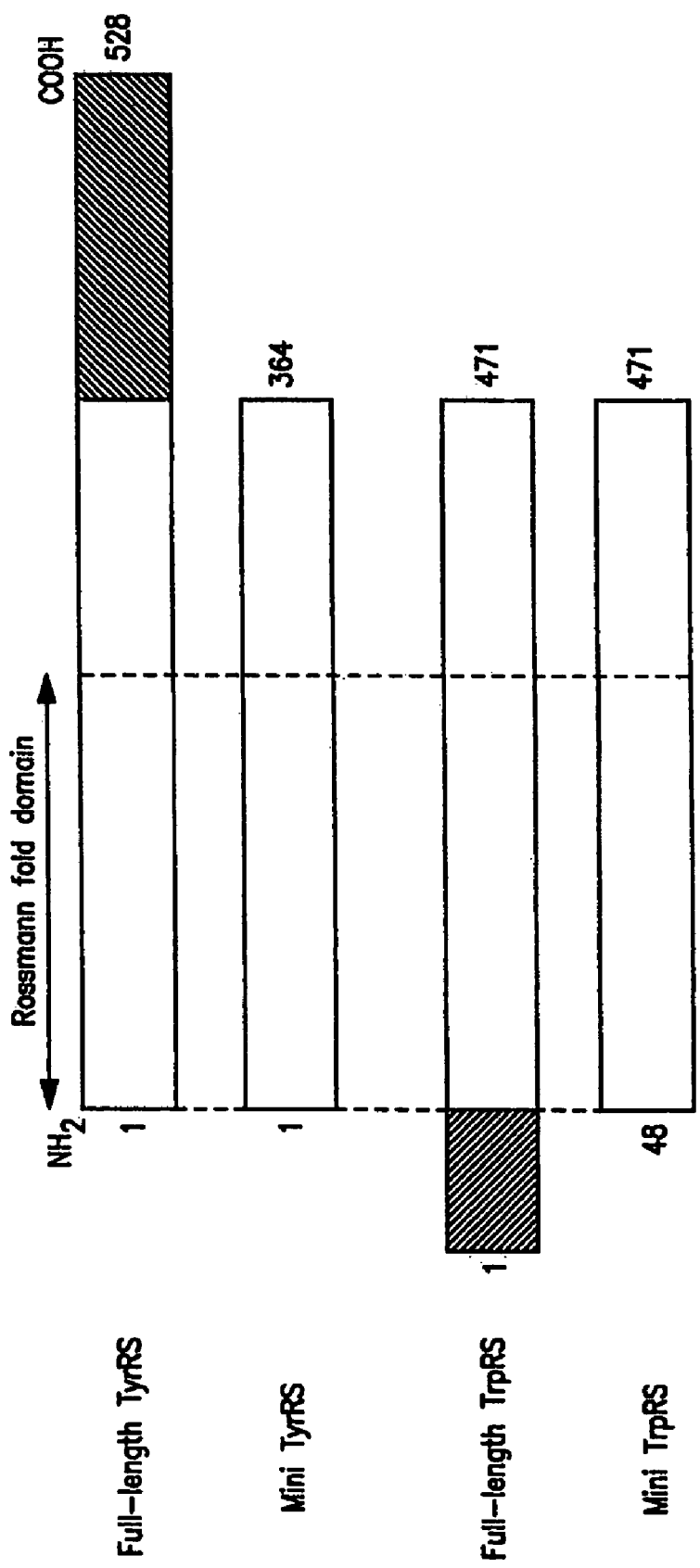
FIG. 15 illustrates a schematic alignment of human full-length TyrRS, human mini TyrRS, human full-length TrpRS, and human mini TrpRS; the carboxyl-terminal and amino-terminal appended domains (hatched) are indicated.

Endotoxin-free recombinant human TyrRS and human TrpRS was prepared as follows. Plasmids encoding full-length TyrRS (528 amino acid residues; FIGS. 1 and 15), truncated TyrRS (mini TyrRS, residues 1-364 of full-length TyrRS; carboxyl-domain of TyrRS, residues 359-528 of full-length TyrRS), full-length TrpRS (471 amino acid residues), or truncated TrpRS (mini TrpRS, residues 48-471 of full-length TrpRS; supermini TrpRS, residues 71-471 of full-length TrpRS), each also encoding a C-terminal tag of six histidine residues, were introduced into *E. coli* strain BL 21 (DE 3) (Novagen, Madison, Wis.). Human mature EMAPII, also encoding a C-terminal tag of six histidine residues, was similarly prepared for use in some Examples. Overexpression of recombinant TyrRS or TrpRS was induced by treating the cells with isopropyl β-D-thiogalactopyranoside for 4 hours. Cells were then lysed and the proteins from the supernatant purified on His•Bind® nickel affinity columns (Novagen) according to the manufacturer's suggested protocol. Following purification, TrpRS proteins were incubated with phosphate-buffered saline (PBS) containing 1 µM $ZnSO_4$ and then free $Zn^{2+}$ was removed (Kisselev et al., 1981, *Eur. J. Biochem.* 120:511-17).

Endotoxin was removed from protein samples by phase separation using Triton X-114 (Liu et al., 1997, *Clin. Biochem.* 30:455-63). Protein samples were determined to contain less than 0.01 units of endotoxin per mL using an E-Toxate® gel-clot assay (Sigma, St. Louis, Mo.). Protein concentration was determined by the Bradford assay (Bio-Rad, Hercules, Calif.) using bovine serum albumin (BSA) as a standard.

EXAMPLE 2

Cytokine Activity of Human TyrRS

Human full-length TyrRS, human mini TyrRS, human TyrRS carboxyl-terminal domain, human EMAP II, and *E. coli* TyrRS were analyzed for cytokine activity in assays examining MP or PMN chemotaxis, MP production of TNFα or tissue factor, or PMN release of myeloperoxidase.

Cells for the various cytokine assays described were prepared from acid citrate dextrose-treated blood of normal healthy volunteers. Human PMNs were isolated from the blood by centrifugation (700×g) over Histopaque 1077 and 1119 (Sigma). Fractions containing PMNs were exposed to 0.2% NaCl for 30 seconds to lyse erythrocytes, immediately restored to isotonicity by the addition of 1.6% NaCl, and then centrifuged for 10 minutes. This procedure was repeated twice. Human MPs were isolated by centrifugation on Histopaque 1077 (Sigma). The mononuclear fraction was obtained, washed twice in Hanks' balanced salt solution, resuspended in RPMI-1640 medium (Sigma) containing 10% heat-inactivated fetal bovine serum (Sigma), plated in tissue culture flasks, and incubated in a 6% $CO_2$ incubator at 37° C. for 1-2 hours (Kumagai et al., 1979, *J. Immunol. Methods* 29:17-25). Nonadherent cells were removed by washing the flasks three times with Hanks' balanced salt solution, and adherent cells were harvested by incubation with calcium-magnesium free phosphate-buffered saline containing 2 mM EDTA for 15 minutes at 4° C., followed by extensive washing.

Figure 2:
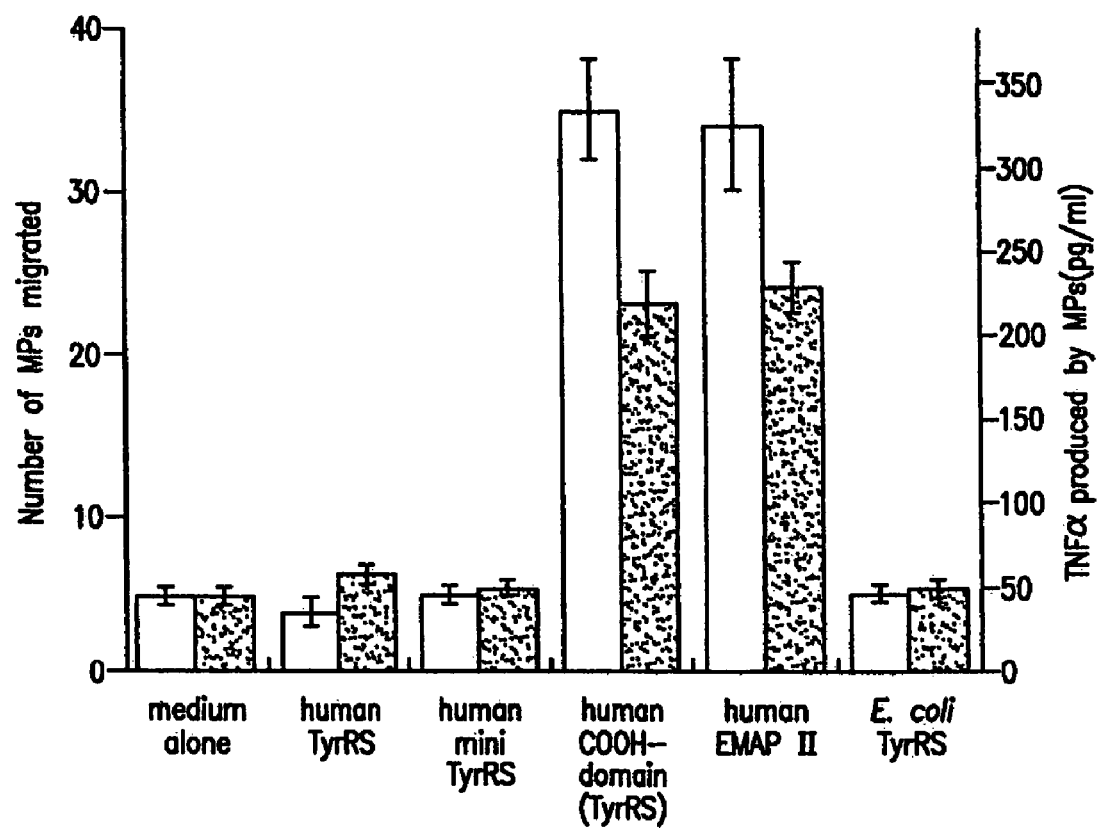
FIG. 2 illustrates the effects of human full-length TyrRS, human mini TyrRS, the human TyrRS carboxyl-terminal domain, human mature EMAP II, and *E. coli* TyrRS on MP chemotaxis (white bars) and MP TNFµ production (gray bars)

MP chemotaxis assays were performed in a ChemoTX microchemotaxis chamber (Neuro Probe, Gaithersburg, Md.) containing polycarbonate filters (5 µm pores) with polyvinylpyrrolidone (PVP). MPs were suspended in RPMI-1640 medium containing 1% heat-inactivated fetal bovine serum, and $10^4$ cells were added to the upper chamber. Sample proteins (1 nM) were added to the lower compartment of chemotaxis chambers, and the chambers were incubated for 3 hours. After incubation, nonmigrating cells were removed, membranes were fixed in methanol, and migrating cells were visualized with the Hemacolor™ stain set (EM Diagnostic Systems, Gibbstown, N.J.). Migrating cells were counted in high-power fields (HPFs). Each determination shown in FIG. 2 represents the average of nine HPF measurements.

MP TNFα production was examined following incubation of $10^5$ MPs with 1 nM of sample protein for 14 hours. Aliquots of the culture supernatant were then assayed for TNFα production using a TNFα enzyme-linked immunosorbent assay kit (Sigma). Each determination shown in FIG. 2 represents the mean of four measurements from at least three independent experiments.

MP tissue factor production was examined following incubation of $10^4$ MPs with 1 nM of sample protein for 4 hours. Tissue factor activity was then inferred from measurements of Factor VIIa-dependent Factor Xa formation (Wolfson et al., 1990 *J. Chromatogr.* 503:277-81). Each determination shown in FIG. 2 represents the mean of four measurements from at least three independent experiments.

Figure 3:
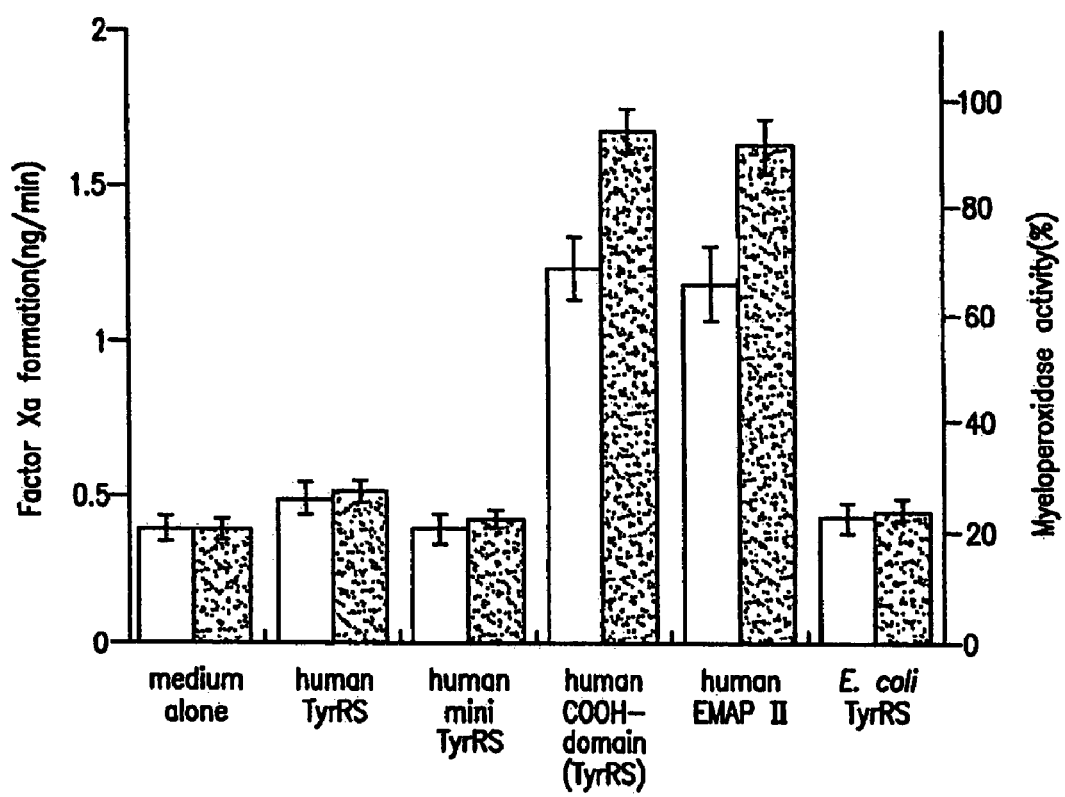
FIG. 3 illustrates the effects of human full-length TyrRS, human mini TyrRS, the human TyrRS carboxyl-terminal domain, human mature EMAP II, and *E. coli* TyrRS on MP tissue factor production (white bars) and PMN release of myeloperoxidase (gray bars)

PMN release of myeloperoxidase was examined following incubation of $3\times10^6$ PMNs per mL with 1 nM of sample protein for 60 minutes. The generation of peroxidase was then measured by the reduction of 3,3',5,5'-tetramethylbenzidine (Barker et al., 1982, *FEBS Lett.* 150:419-23). Peroxidase activity is shown in FIG. 3 as the percent of total peroxidase activity where 100% peroxidase activity is defined as the activity observed for $3\times10^6$ PMNs following exposure to 10 µM phorbol ester for 60 minutes. Each determination shown in FIG. 3 represents the mean of four measurements from at least three independent experiments.

PMN chemotaxis assays were performed in a ChemoTX microchemotaxis chamber (described herein). Sample proteins (1 nM) were added to the lower compartment of chemotaxis chambers, and $10^4$ PMNs were added to the upper compartment. Chambers were incubated for 45 min, and migrating cells were counted in HPFs. Each determination shown in FIG. 2 represents the average of nine HPF measurements.

Figure 4:
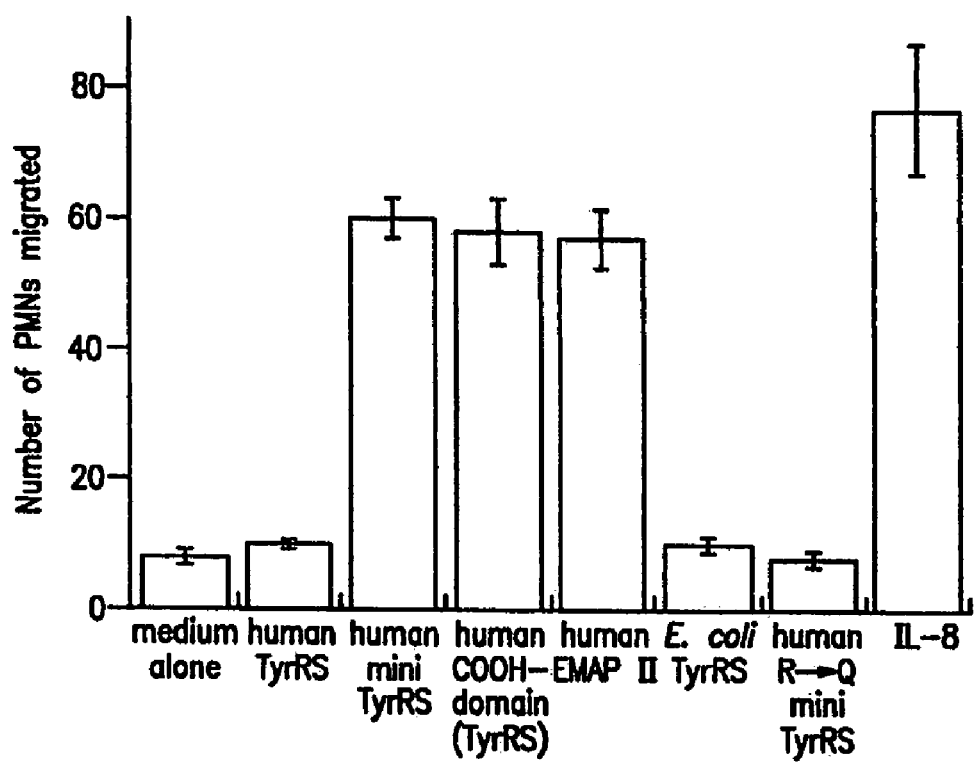
FIG. 4 illustrates the effects of human full-length TyrRS, human mini TyrRS, the human TyrRS carboxyl-terminal domain, human mature EMAP II, *E. coli* TyrRS, human TyrRS mutant, and IL-8 on PMN chemotaxis.
Figure 5:
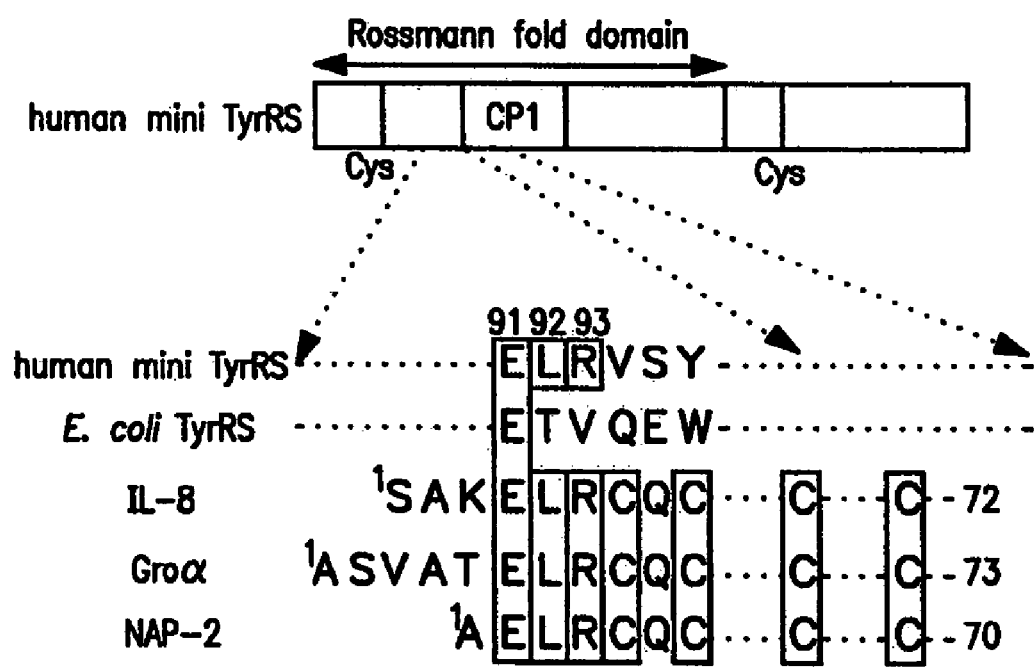
FIG. 5 illustrates a schematic partial alignment of human mini TyrRS (SEQ ID NO: 17), E. coli TyrRS (SEQ ID NO: 18), IL-8 (SEQ ID NO: 19), Groα (SEQ ID NO: 20), and NAP-2 (SEQ ID NO: 21); the connective polypeptide 1 (CP1) which splits the Rossman nucleotide-binding fold in TyrRS is indicated.

As shown in FIG. 2 (white bars), TyrRS carboxyl-terminal domain induced MP migration to an extent comparable with that observed for EMAP II. In contrast, no chemotaxis was observed with full-length TyrRS. The TyrRS carboxyl-terminal domain also stimulated production of TNFα (FIG. 2, gray bars) and tissue factor (FIG. 3, white bars) in MPs, induced the release of myeloperoxidase in PMNs (FIG. 3, gray bars), and induced PMN migration (FIG. 4). The induction of PMN migration by the TyrRS carboxyl-terminal domain and EMAP II showed the bell-shaped concentration dependence that is characteristic of chemotactic cytokines (Wakasugi et al., supra). Full-length TyrRS had none of the properties observed for the carboxyl-terminal domain (FIGS. 2-4).

The cytokine activity of the amino-terminal catalytic domain of TyrRS (mini TyrRS) examined in parallel with that of the TyrRS carboxyl-terminal domain. Mini TyrRS did not induce MP migration (FIG. 2, white bars) and did not stimulate production of TNFα (FIG. 2, gray bars) or tissue factor (FIG. 3, white bars) in MPs. Surprisingly, mini TyrRS did induce PMN migration (FIG. 4), and this activity showed a bell-shaped concentration dependence. These results suggest that mini TyrRS is a leukocyte chemoattractant. The PMN response to mini TyrRS added to the lower compartment of a chemotaxis chamber was attenuated by the addition of mini TyrRS to the upper well, indicating that enhanced PMN migration was due to chemotaxis, not simply chemokinesis (stimulated random movement). *E. coli* TyrRS, which is similar in size to human mini TyrRS, was inactive in all of the assays (FIGS. 2-4).

EXAMPLE 3

Mutation of Human TyrRS ELR Motif

All α-chemokines (CXC-chemokines) that function as PMN chemoattractants, such as IL-8, have a conserved Glu-Leu-Arg (ELR) motif preceding the first cysteine in the amino-terminus (Becker, 1977, *Arch. Pathol. Lab. Med.* 101: 509-13). The ELR motif is critical for receptor binding and neutrophil activation (Baggiolini et al., 1997, *Annu. Rev. Immunol.* 15:675-705). Human mini TyrRS also possesses an ELR motif within the catalytic domain (FIG. 5), which further comprises a Rossmann nucleotide-binding fold. The Rossman nucleotide-binding fold is characteristic of all class I aminoacyl-tRNA synthetases. This motif is conserved among mammalian TyrRS molecules.

The significance of the TyrRS ELR motif was examined by preparing a mini TyrRS mutant in which the ELR motif was mutated to ELQ (Glu-Leu-Gln); the Arg residue appears to be particularly important for receptor binding (Baggiolini et al., supra). The mini TyrRS mutant was tested for cytokine activity as described in Example 2. Mini TyrRS mutant did not induce PMN migration (FIG. 4), suggesting that, as with other α-chemokines, the ELR motif in mini TyrRS plays an important role in PMN receptor binding.

EXAMPLE 4

Human TyrRS Binding Assay

The interaction of human mini TyrRS and PMNs was examined in binding studies using radioiodinated TyrRS molecules (Moser et al., 1993, *J. Biol. Chem.* 268:7125-28). Custom radioiodination of mini TyrRS with was performed by Research & Diagnostic Antibody (Richmond, Calif.). In the binding assays, $2\times10^6$ PMNs were first suspended in 120 µL of RPMI-1640 medium containing 20 mM Hepes (pH 7.4) and 10 mg/mL bovine serum albumin. The PMN cell suspension was then incubated on ice for 2 hours with 10 nM $^{125}$I-human mini TyrRS (specific activity of ~60 Ci/mmol) and either a 200-fold molar excess of unlabeled ligands or no unlabeled ligands. Following incubation, cells were separated from unbound radioactivity by centrifugation at approximately 8000×g for 2 minutes through 500 µL of a 10% sucrose/phosphate-buffered saline (PBS) cushion. The supernatant was aspirated, and the cell sediment was resuspended using EcoLite (ICN Biomedicals, Irvine, Calif.) and analyzed in a scintillation counter. The maximal specific response represents 2000 counts per minute. The data shown in FIG. 6 represent the mean of three independent measurements.

Incubation of $^{125}$I-mini TyrRS with PMNs led to dose-dependent specific binding at 4° C., which gave linear Scatchard plots (with an apparent dissociation constant of $K_d$=21 nM; 23,000 receptors/PMN). As shown in FIG. 6, the presence of unlabeled mini TyrRS inhibited the binding of $^{125}$I-mini TyrRS to PMNs. In contrast, human full-length TyrRS, human mini TyrRS mutant, and *E. coli* TyrRS did not inhibit the binding of $^{125}$I-mini TyrRS. Thus, the lack of a PMN chemotactic effect for full-length TyrRS, mini TyrRS mutant, and *E. coli* TyrRS is consistent with their lack of PMN binding. In addition, neither the TyrRS carboxyl-terminal domain nor EMAP II inhibited $^{125}$I-mini TyrRS binding to PMNs. Thus, the PMN receptor for mini TyrRS differs from that for the TyrRS carboxyl-terminal domain or for mature EMAP II.

Competitive binding assays were also performed to examine the ability of interleukin-8 (IL-8), melanoma growth stimulatory activity (Gro), or neutrophil activating protein-2 (NAP-2) (α-chemokines possessing the ELR motif) to bind the same PMN receptor that mini TyrRS binds. IL-8 binds to the type A and type B IL-8 receptors (known, respectively as CXCR1 and CXCR2), while Gro and NAP-2 bind to the type B IL-8 receptor (Becker, supra). In the binding assays, 2×10$^6$ PMNs or basophilic leukemia cells in 120 µL of RPMI-1640 medium containing 20 mM Hepes (pH 7.4) and 10 mg/mL bovine serum albumin (BSA) were incubated on ice for 2 hours with 10 nM $^{125}$I-mini TyrRS (having a specific activity of ~60 Ci/mmol) in the absence or presence of a 200-fold molar excess of either human recombinant IL-8 (Calbiochem, La Jolla, Calif.), human recombinant Gro (Biosource International, Camarillo, Calif.), or human recombinant NAP-2 (Biosource International). Following incubation, cells were separated from unbound radioactivity as described herein.

Figure 6:
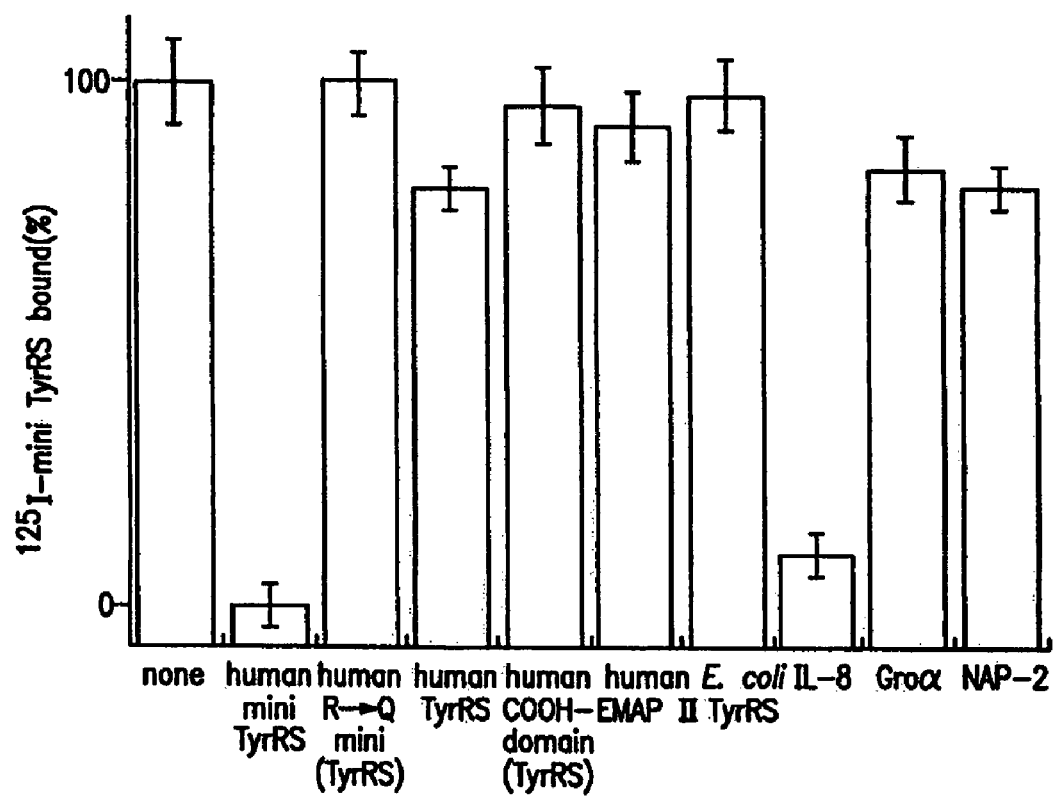
FIG. 6 illustrates the results of competition assays in which unlabeled human mini TyrRS, human TyrRS mutant, human full-length TyrRS, the human TyrRS carboxyl-terminal domain, human mature EMAP II, E. coli TyrRS, IL-8, Groα, or NAP-2 was used in molar excess with $^{125}$I-human mini TyrRS on PMNs.

As shown in FIG. 6, IL-8 inhibited $^{125}$I-mini TyrRS binding almost completely, whereas Gro and NAP-2 did not significantly inhibit the binding. These results suggest that mini TyrRS specifically binds to the type A IL-8 receptor. To gain further insight into the receptor for mini TyrRS, we studied RBL2H3 rat basophilic leukemia cells that had been transfected with the gene for IL-8 receptor type A or type B (Lee, et al., 1992, *J. Biol. Chem.* 267:16283-87). Untransfected RBL2H3 cells express neither the type A nor type B receptors. Mini TyrRS bound with high affinity to cells expressing the type A IL-8 receptor ($K_d$=8 nM) as did IL-8 ($K_d$=1 nM) but not to those expressing the type B receptor ($K_d$>200 nM). Scatchard analyses demonstrated that the type A-expressing transfectants had a similar number of binding sites for human mini TyrRS as for IL-8.

EXAMPLE 5

Secretion of Human TyrRS From U-937 Cells

In order to examine whether human TyrRS, like human EMAP II, is secreted from apoptotic tumor cells, human histiocytic lymphoma U-937 cells were first grown in serum-free medium to induce apoptosis. Prior to growth in serum-free medium, U-937 cells were maintained in RPMI-1640 medium containing 10% heat-treated FBS (Sigma), 100 U/mL penicillin and 100 µg/mL streptomycin (Sigma) in an atmosphere of 6% $CO_2$ in air at 37° C. U-937 cells were maintained in logarithmic growth phase by routine passage every 2-3 days. For serum-free growth, 4×10$^6$ U-937 cells were cultured in RPMI-1640 medium without FBS for 24 hours. Apoptosis of U-937 cells was verified by DNA fragment assay, in which the characteristic DNA ladder for apoptotic cells was observed on an agarose gel.

Cell supernatants were collected following growth of U-937 cells in serum-free media for 4, 12, or 24 hours. These supernatants were then examined by Western blot analysis using a rabbit polyclonal anti-TyrRS antibody. To examine proteins in the cell supernatant, 20 mL of spent culture medium was first treated with 2 mM PMSF, 10 µg/mL aprotinin, 20 µg/mL leupeptin, and 10 µg/mL pepstatin A. Treated culture medium was concentrated using Centriprep-10 columns (Amicon, Beverly, Mass.) and then separated on a 12.5% SDS-polyacrylamide gel. Following transfer onto an Immobilon-P™ membrane (Millipore, Bedford, Mass.), blots were blocked with PBS and 3% BSA and incubated with rabbit polyclonal anti-TyrRS antibodies. After washing, blots were incubated with a 1:4000 dilution of horseradish peroxidase-linked anti-rabbit IgG (Amersham Life Science, Arlington Heights, Ill.) for detection of TyrRS.

Cell lysates were parepared by first washing collected U-937 cells twice with ice-cold PBS and then resuspending the cells in lysis buffer containing 25 mM HEPES (pH 7.5), 5 mM EDTA, 5 mM dithiothreitol, 0.1% CHAPS, 2 mM phenylmethylsulfonyl fluoride (PMSF), 10 µg/mL aprotinin, 20 µg/mL leupeptin, and 10 µg/mL pepstatin A. Cells were then frozen and thawed three times in liquid nitrogen and centrifuged for 30 minutes at 4° C.

Figure 7A:
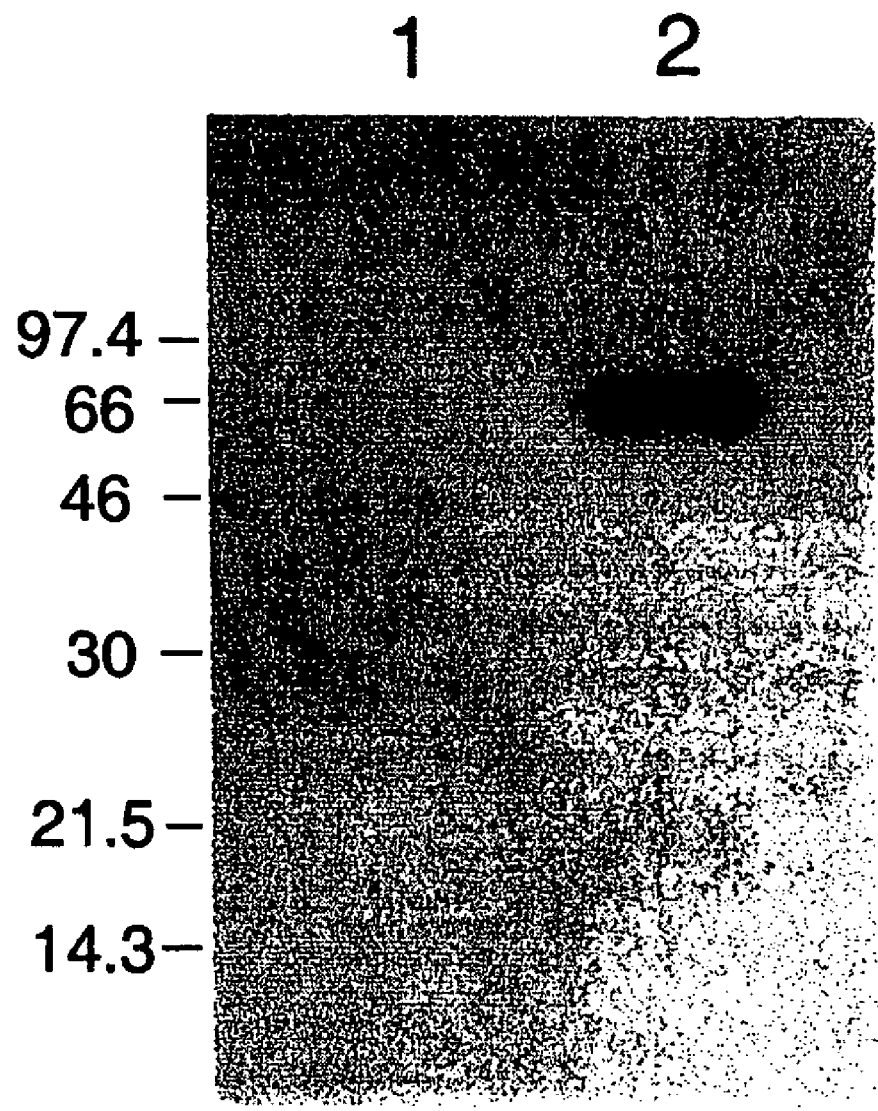
FIGS. 7A-7B illustrate the results of immunoblot analysis of (A) supernatants following growth of U-937 cells in normal media (lane 1) and serum-free media (lane 2), and (B) supernatants following growth of U-937 cells in serum-free media for 4, 12, or 24 hours (lanes 1-3), or from a cell extract isolated from U-937 cells grown in serum-free media for 24 hours.
Figure 7B:
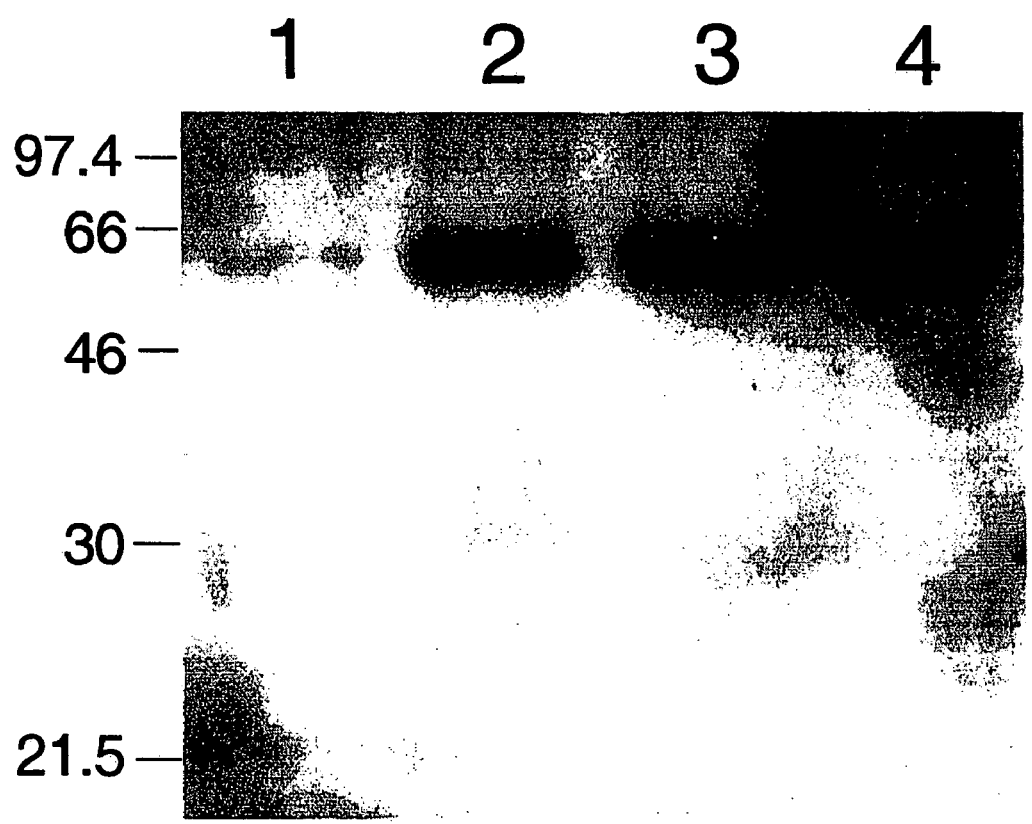

Protein immunoblot analysis of the cell supernatant fraction, with a polyclonal antibody to human TyrRS, revealed that full-length TyrRS was secreted from apoptotic tumor cells, but not from cells under normal conditions (FIG. 7A). Under apoptotic conditions, the amount of secreted human full-length TyrRS increased with the incubation time (FIG. 7B). After 24 hours of growth in serum-free medium, more than 50% of the total native TyrRS was released from the cells. A similar proportion of mature EMAP II is secreted from U-937 cells under the same conditions (Kao, et al., 1994, *J. Biol. Chem.* 269:25106-19).

To exclude the possibility that the apparent secretion of TyrRS was due to cell lysis, the activity of cytosolic lactate dehydrogenase (LDH) in the supernatants was measured. LDH activities were determined spectrophotometrically with a CytoTox 96 Non-Radioactive Cytotoxicity Assay kit (Promega, Madison, Wis.). LDH activity in the supernatants was less than 10% of that in cell extracts and did not increase even after 72 hours of incubation. These results are consistent with the hypothesis that the increase of TyrRS in the supernatants is due to protein secretion.

The permeability of the "secreting" apoptotic cells was also examined using Trypan Blue exclusion as a test for intact cells. The apoptotic cells did not take up the stain, indicating that cell lysis was not responsible for the appearance of TyrRS in the apoptotic cell supernatant. As a further control, human alanyl-tRNA synthetase (AlaRS), which possesses none of the cytokine-like motifs of human TyrRS, was examined for possible secretion. Protein immunoblot analysis showed that, under the same apoptotic conditions, no AlaRS was secreted. The activities of four other aminoacyl-tRNA synthetases in the supernatants or cell extracts of apoptotic U-937 cells were also studied. When cell extracts were used in assays with bovine tRNA, aminoacylation was observed only for alanine, isoleucine, lysine, valine, and tyrosine. In contrast, when supernatants were used, only tyrosine was aminoacylated.

EXAMPLE 6

Cleavage of Human TyrRS by PMN Elastase

In order to examine whether full-length TyrRS can be cleaved by PMN elastase, a protease released from PMNs (Wright, et al., 1992, *J. Cell. Biochem.* 48:344-55), full-length TyrRS was treated with PMN elastase in PBS (pH 7.4) at a protease:protein ratio of 1:3000 for 30 minutes at 37° C. Following cleavage, the sample was separated on a 12.5% SDS-polyacrylamide gel along with untreated human full-length TyrRS, human mini TyrRS, the human TyrRS carboxyl-terminal domain, and a human extended TyrRS carboxyl-terminal domain. Immunoblot analysis was performed as described in Example 5.

Figure 8A:
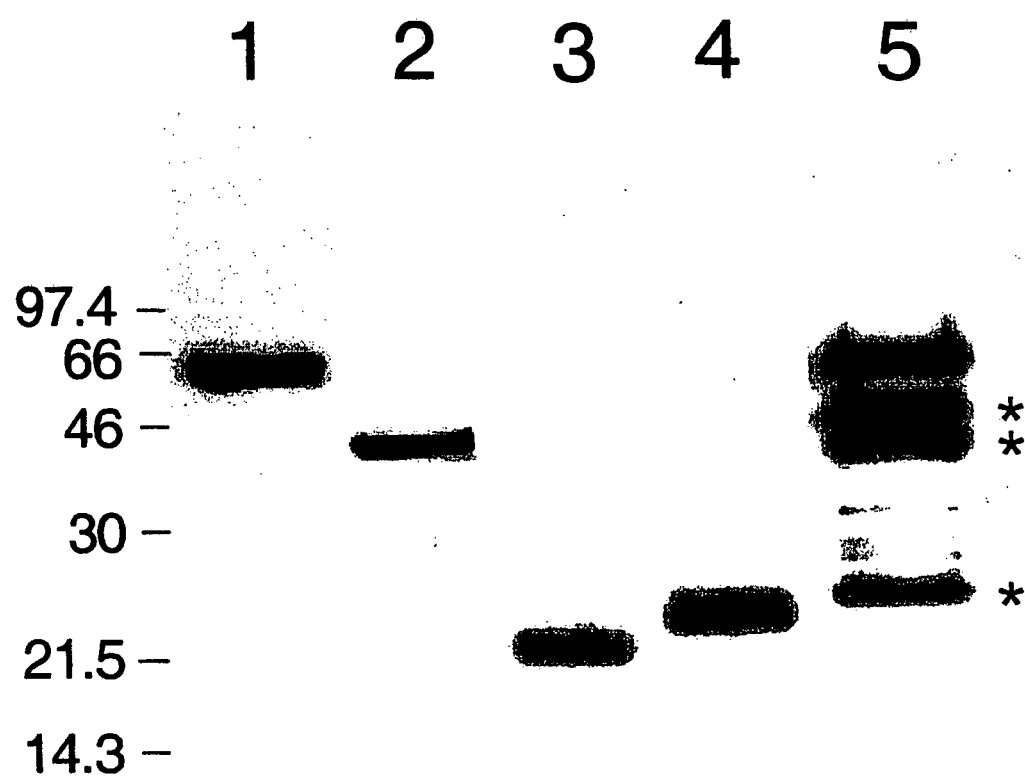
FIGS. 8A-8B illustrate (A) the results of immunoblot analysis of human full-length TyrRS (lane 1), human mini TyrRS (lane 2), the TyrRS carboxyl-terminal domain (lane 3), the extended carboxyl-terminal domain of human TyrRS (lane 4), and human full-length TyrRS following cleavage with PMN elastase (lane 5), and (B) a schematic representation of the cleavage sites for human pro-EMAP II (SEQ ID NO: 22) and human full-length TyrRS (SEQ ID NO: 23)
Figure 8B:
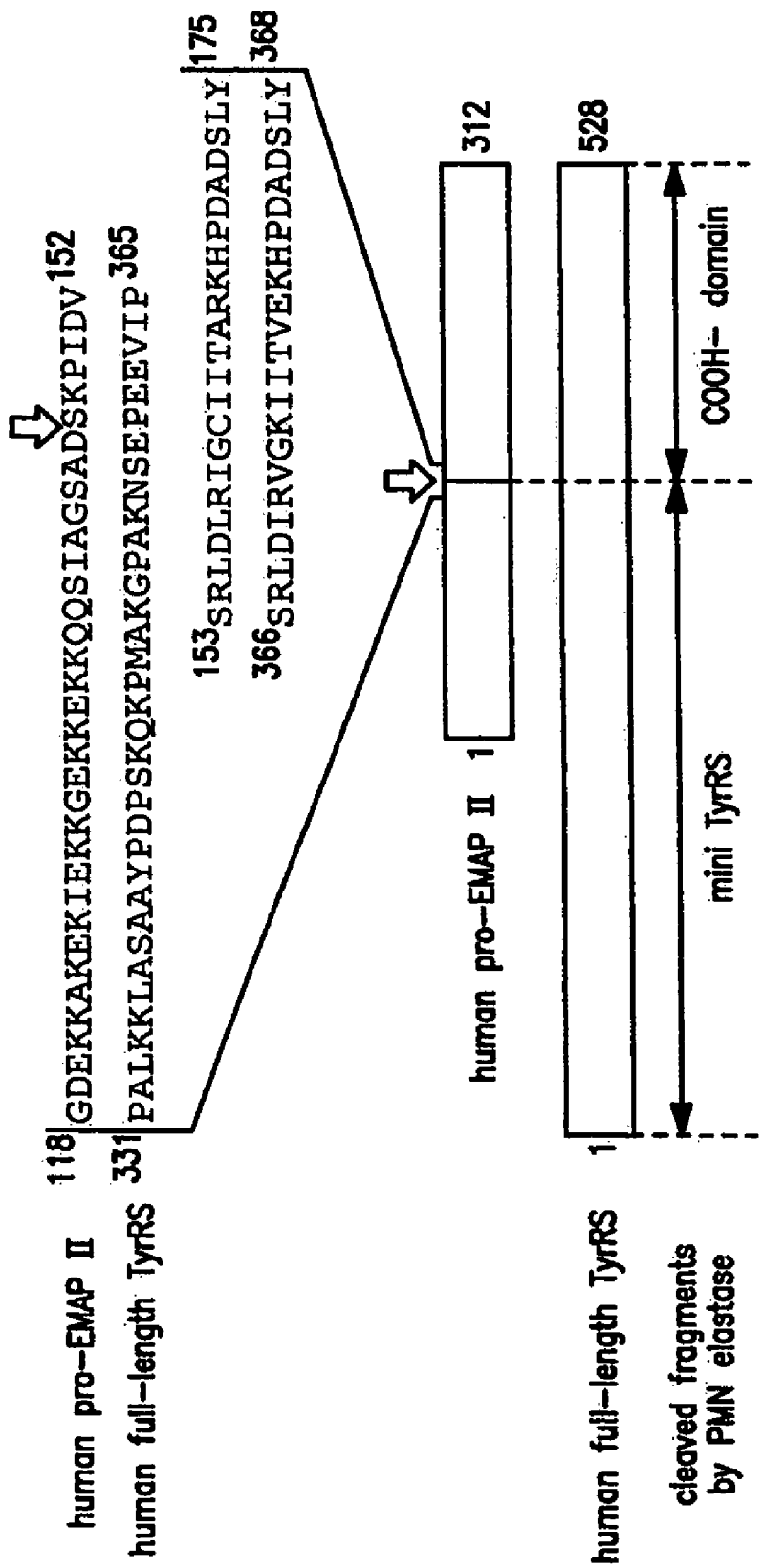
Figure 9:
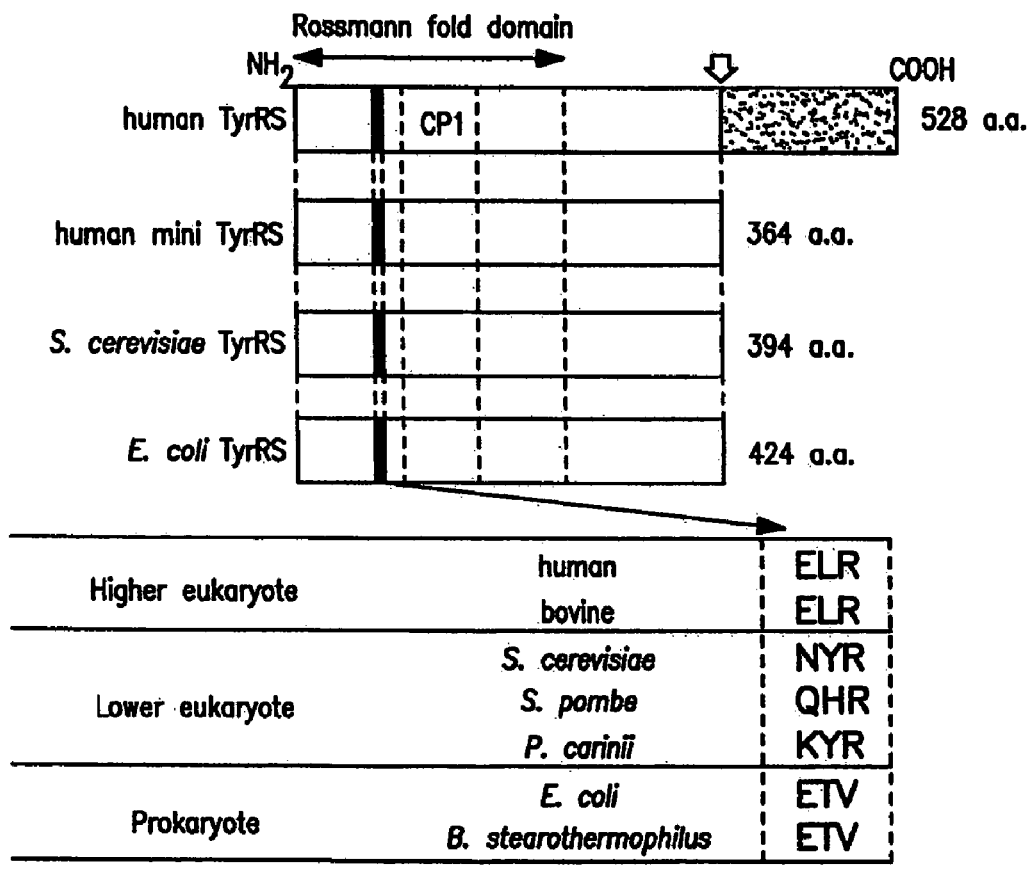
FIG. 9 illustrates a schematic alignment of human full-length TyrRS, human mini TyrRS, S. cerevisiae TyrRS, and E. coli TyrRS.

As shown in FIG. 8A, the addition of PMN elastase to full-length TyrRS generated a doublet of ~40 kD fragments and a ~24 kD fragment. The ~40 kD fragments have a molecular weight similar to that of mini TyrRS. Sequence analysis of the ~40 kD fragments revealed that each has an amino-terminal sequence of M-G-D-A-P (SEQ ID NO: 56), as does human full-length TyrRS. FIG. 8B illustrates the local sequence comparison between human pro-EMAP II and human full-length TyrRS in the regions near their cleavage sites.

Immunoblot analysis further revealed that the ~24 kD fragment is a carboxyl-terminal domain. A recombinant extended TyrRS carboxyl-terminal domain (residues 344-528 of human full-length TyrRS) was prepared to more closely reproduce the putative cleavage site recognized by PMN elastase. Both the extended TyrRS carboxyl-terminal domain and the PMN elastase ~24 kD cleavage product migrated to similar positions on an SDS-polyacrylamide gel (FIG. 8A). Subsequent experiments demonstrated that the extended carboxyl-terminal domain was capable of can inducing both MP and PMN chemotaxis. In experiments examining the ability of a recombinant truncated mini TyrRS (comprising residues 1-344 of human full-length TyrRS in comparison to mini TyrRS which comprises TyrRS residues 1-364) to act as a chemoattractant, the truncated mini TyrRS was capable of functioning as a chemoattractant for PMNs but not for MPs.

In vivo cleavage analysis was performed in IL-8-stimulated PMNs, which release PMN elastase (Bjørnland et al., 1998, *Int. J. Oncol.* 12:535-40). Recombinant human full-length TyrRS. when added to such cells, was cleaved into ~40 kD and ~24 kD fragments. When full-length TyrRS was added to nonstimulated PMNs, no TyrRS cleavage was observed. Immunoblot analysis, using antibodies specific for the amino-terminal and carboxyl-terminal domains indicated that the ~40 kD and ~24 kD fragments comprised mini TyrRS and the TyrRS carboxyl-terminal domain, respectively. When native TyrRS, which was isolated from apoptotic U-937 cells, was added to IL-8-stimulated PMNs, the same ~40 kD and ~24 kD fragments were generated.

The demonstration that human full-length TyrRS can be split into two distinct cytokines, suggests that there is a link between protein synthesis and signal transduction. In principle, the secretion of an essential component of the translational apparatus as an early event in apoptosis would be expected to arrest translation and thereby accelerate apoptosis. The secreted TyrRS cytokines could function as intercellular signal transducers, attracting PMNs and thus amplifying the local concentration of PMN elastase. This recursive cycle could enhance cleavage of secreted human TyrRS, thereby enhancing recruitment of macrophages to sites of apoptosis, which would promote removal of cell corpses.

EXAMPLE 7

Cytokine Activity of Non-Human TyrRS

As shown in Example 3, the ELR motif of human mini TyrRS plays an important role in PMN receptor binding, as it does in α-chemokines. While the critical ELR motif of α-chemokines is conserved among mammalian TyrRS molecules, the corresponding sequence element of *S. cerevisiae* is NYR and that of *E. coli* TyrRS is ETV (FIG. 9). *E. coli* TyrRS neither activates nor binds to the IL-8 receptors on PMNs (see Example 2). The effect of *S. cerevisiae* TyrRS on PMN receptor binding and PMN migration was examined as described herein (see Examples 2 and 4).

Figure 10:
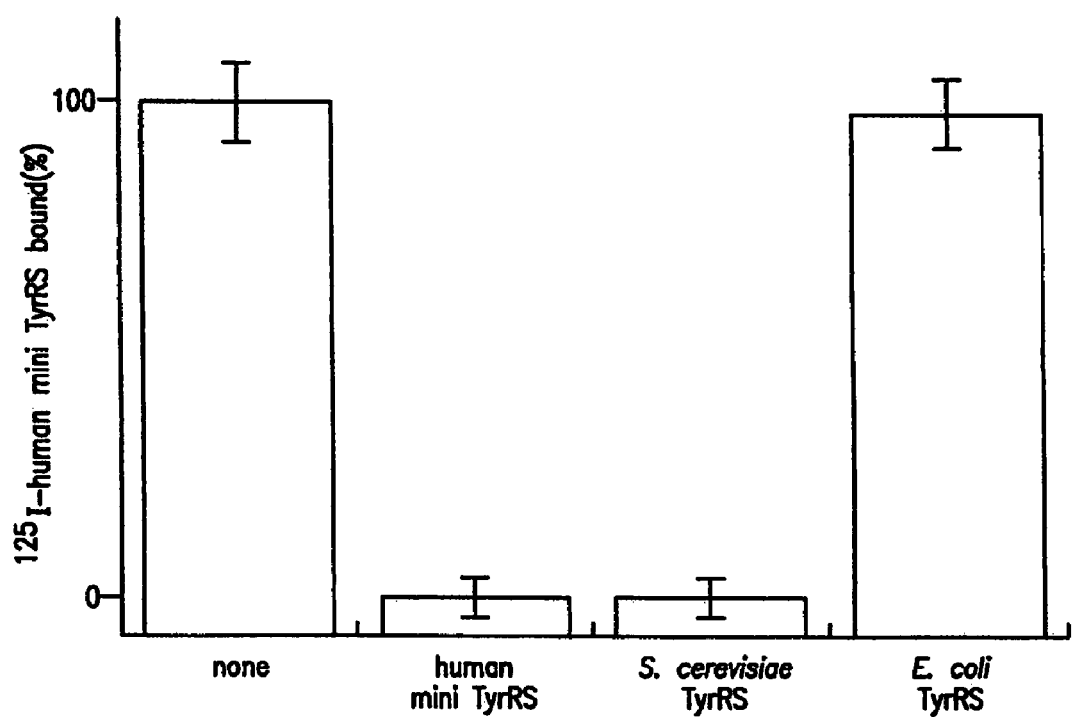
FIG. 10 illustrates the results of competition assays in which unlabeled human mini TyrRS, S. cerevisiae TyrRS, or E. coli TyrRS was used in molar excess with $^{125}$I-human mini TyrRS on PMNs.

As shown in Example 4, the binding of human mini TyrRS with PMNs is strictly competitive with IL-8. This binding occurs to the IL-8 type A receptor with a dissociation constant $K_d$ of 8 nM. Incubation of $^{125}$I-mini TyrRS with PMNs led to dose-dependent specific binding at 4° C. As shown in FIG. 10, the binding of $^{125}$I-mini TyrRS is inhibited by the presence of excess amounts of unlabeled mini TyrRS but not by excess amounts of *E. coli* TyrRS. In contrast with *E. coli* TyrRS, *S. cerevisiae* TyrRS inhibited the binding of $^{125}$I-mini TyrRS to PMNs. The dissociation constant for *S. cerevisiae* TyrRS does not appear to be more than 200-fold higher than that for human mini TyrRS. These results demonstrate that while a lower eukaryotic TyrRS can bind to the PMN receptor for human mini TyrRS, a bacterial TyrRS cannot.

Figure 11:
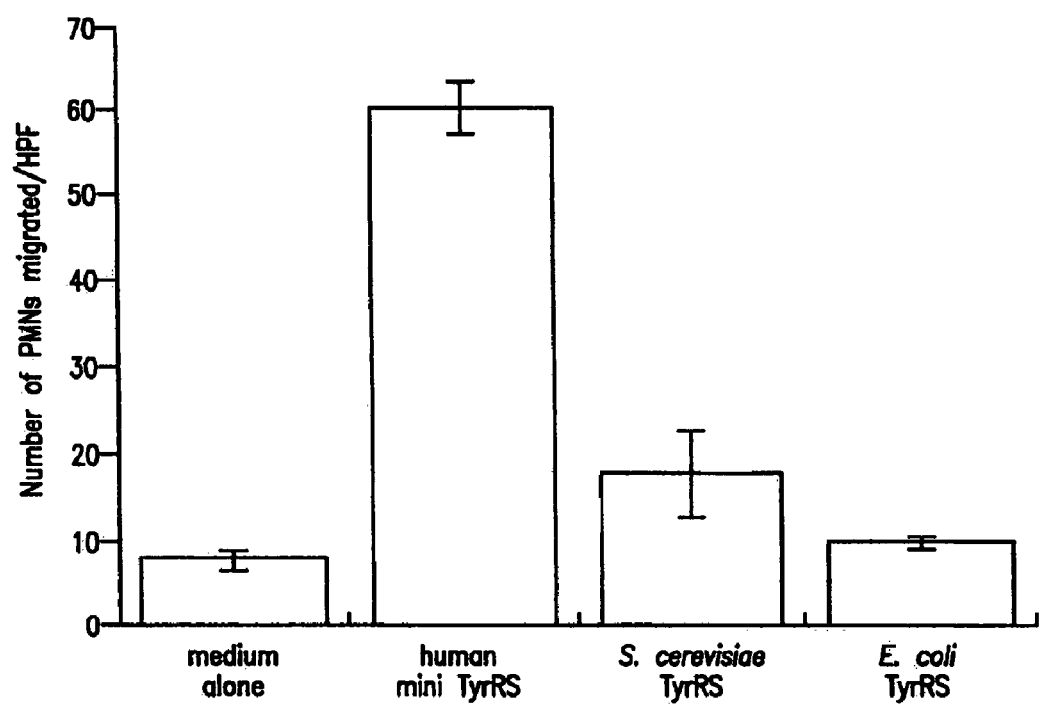
FIG. 11 illustrates the effects of human mini TyrRS, S. cerevisiae TyrRS, or E. coli TyrRS on PMN chemotaxis.

To determine whether the binding of *S. cerevisiae* TyrRS to PMNs was associated with cytokine activity, the chemotactic activities of human mini TyrRS, *S. cerevisiae* TyrRS, and *E. coli* TyrRS were examined. As shown in FIG. 11, incubation of PMNs with human mini TyrRS led to an induction of PMN migration. In contrast, no chemotaxis was observed with either *S. cerevisiae* TyrRS or *E. coli* TyrRS. The potential cytokine activity of *S. cerevisiae* TyrRS was examined at concentrations of 0.1, 1, 10, 100, and 1000 nM. No significant chemotaxis, however, was observed at any concentration (FIG. 11 shows the results at a concentration of 1 nM). Thus, the binding of *S. cerevisiae* TyrRS to PMNs is not associated with a serendipitous cytokine function.

Because many residues and motifs are conserved among eukaryotic TyrRS molecules that are not found in their prokaryotic counterparts, the binding of *S. cerevisiae* TyrRS to PMNs could reflect its structural similarity to human mini TyrRS. One reason why *S. cerevisiae* TyrRS does not have IL8-like cytokine activity might be attributed to the variation (NYR) of the sequence of critical ELR motif. As shown in Example 3, a simple change in the ELR motif of mini TyrRS inactivated its IL8-like activity. It is noteworthy, in this respect, that prokaryotic and eukaryote cytoplasmic TyrRS molecules cannot cross-aminoacylate their respective tyrosine tRNAs because of a sequence variation in a peptide motif that is needed for discrimination of a species-specific difference in their respective tRNA sequences (Wakasugi et al., supra). Thus, both cytokine and RNA-related activities of human TyrRS are sensitive to the most subtle sequence variations.

EXAMPLE 8

Dimeric Structure for Human Mini TyrRS

Prokaryotic and lower eukaryotic TyrRS molecules form stable dimers (Quinn et al., 1995, *Biochemistry* 34:12489-95). The possibility that the cytokine activities of human mini TyrRS were due to its oligomeric state, and this state differed from that of prokaryotic and lower eukaryotic homologs, was examined. In order to determine the oligomeric state of mini TyrRS, the molecular weight of mini TyrRS was assayed by gel filtration chromatography on a Superose 6 HR 10/30 column (Amersham Pharmacia Biotech). A gel filtration standard (Bio-Rad) that included thyroglobulin, bovine gamma globulin, chicken ovalbumin, equine myoglobin, and vitamin B-12 was used. Gel filtration of *E. coli* TyrRS and *S. cerevisiae* TyrRS was examined as a control. Human mini TyrRS eluted at the same position as the *E. coli* and *S. cerevisiae* TyrRS, with an estimated molecular weight of 90 kDa. This value corresponds closely to that which would be expected for the dimeric form (84 kDa).

Under the experimental conditions of NMR or x-ray analyses, native IL-8 is a dimer (Clore and Gronenborn, supra). However, at physiologically more relevant concentrations, monomeric and dimeric forms of IL-8 are in equilibrium, with the monomer being the prevalent form (Burrows et al., 1994, Biochemistry 33:12741-45). Dimerization-deficient IL-8 analogues were engineered by chemical modification or by mutations of residues at the dimer interface (Lowman et al., 1997, Protein Sci. 6:598-608). Their structural analyses clarified that the IL-8 monomers have the same tertiary folding as the dimer (id.). In addition, their functional analyses showed that the monomers have full cytokine activity in vitro and in vivo (id.). On the other hand, to mimic the dimeric form of IL-8, cross-linked single-chain dimers were designed (Leong et al., 1997, Protein Sci. 6:609-17). The results of chemotaxis and receptor binding assays showed that the dissociation of the dimer is not required for the biological activities (id.). Thus, dimerization of IL-8 introduces no structural constraints for its tertiary folding or activities. Similarly, the ELR motif needed for the IL8-like activity is accessible in the dimeric structure found here for human mini TyrRS.

EXAMPLE 9

Cytokine Activity of Peptides Derived from EMAP II-Like Domains

Figure 12:
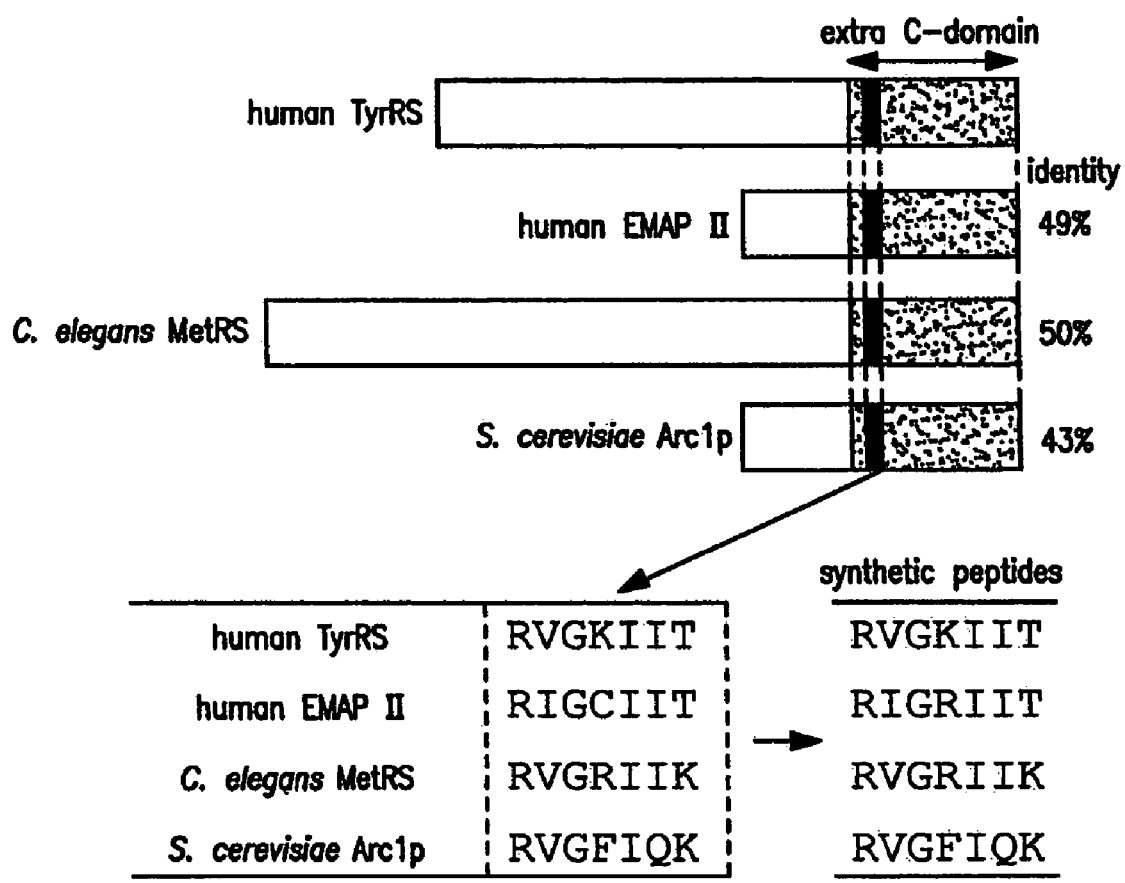
FIG. 12 illustrates a schematic alignment of the human EMAP II-like domains and corresponding synthetic peptides for human full-length TyrRS (SEQ ID NO: 24), human EMAP II (SEQ ID NO: 25-26), C. elegans MetRS (SEQ ID NO: 27), and S. cervisiae Arc1p (SEQ ID NO: 28)

A synthetic peptide comprising seven residues near the amino-terminus of human mature EMAP II (R-I-G-R-I-I-T; SEQ ID NO: 26) can induce PMN or MP migration (Kao et al., 1994, J. Biol. Chem. 269:9774-82). The cytokine activity of a synthetic peptide derived from the corresponding region of the TyrRS carboxyl-terminal domain (R-V-G-K-I-I-T; SEQ ID NO: 24; FIG. 12) was examined in PMN and MP migration assays. The chemotactic assays were performed as described in Example 2. Peptides used in such assays were synthesized, purified by high performance liquid chromatography, and analyzed by mass spectroscopy by Genosys Biotechnologies, Inc. (Woodlands, Tex.). In preparing the EMAP II-derived peptide, a cysteine residue was replaced by an arginine residue in order to enhance the stability and solubility of the synthetic peptide (FIG. 12). This substitution did not alter the biological properties of the EMAP II peptide, as demonstrated by Kao et al., 1994, J. Biol. Chem. 269:9774-82.

Figure 13:
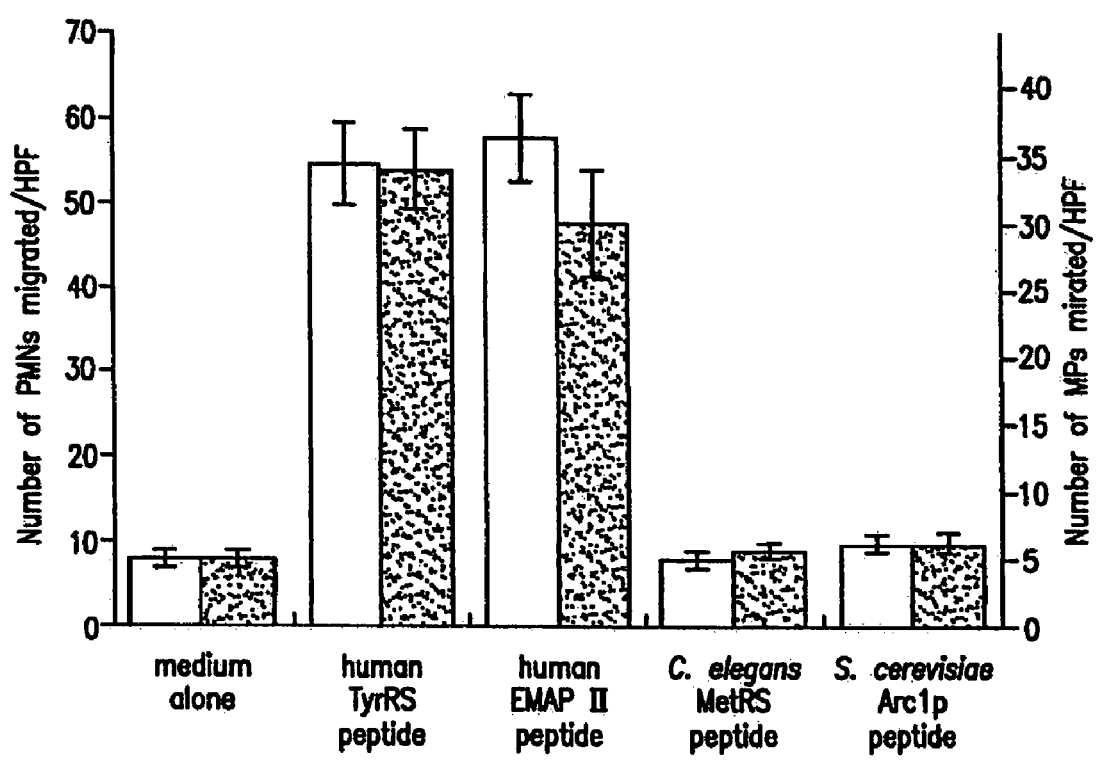
FIG. 13 illustrates the effects of synthetic peptides derived from human TyrRS, human EMAP II, C. elegans MetRS, and S. cervisiae Arc1p on PMN chemotaxis

As shown in FIG. 13, The TyrRS carboxyl-terminal domain peptide induced PMN migration (white bars) and MP migration (gray bars). The effect of the TyrRS carboxyl-terminal domain peptide on PMN and MP migration showed a dose-dependence similar to that of the mature EMAP II peptide. Thus, the TyrRS carboxyl-terminal domain and mature EMAP II share similar peptide motifs for chemotaxis at the same positions in their respective sequences. Portions of S. cerevisiae Arc1p and C. elegans MetRS have high sequence homology with the TyrRS carboxyl-terminal domain (Kleeman et al., supra; Simos et al., 1998, Mol. Cell 1:235-42). The cytokine activity of synthetic peptides corresponding to the EMAP II R-I-G-R-I-I-T peptide and derived from S. cerevisiae Arc1p (R-V-G-F-I-Q-K; SEQ ID NO: 28) and C. elegans MetRS (R-V-G-R-I-I-K; SEQ ID NO: 27) were also examined in PMN and MP migration assays. As shown in FIG. 13, neither peptide induced PMN or MP migration. Thus, the cytokine activities of human mature EMAP II and the TyrRS carboxyl-terminal domain are specified by highly specific peptide sequences.

Some amino acid residues in peptides corresponding to the R-V-G-K-I-I-T motif from the TyrRS carboxyl-terminal domain are highly conserved among other proteins of both prokaryotes and eukaryotes (Table I). However, heptapeptides derived from S. cerevisiae Arc1p or C. elegans MetRS did not have EMAP II-like cytokine activities. Thus, the EMAP II-like motif in these proteins may have been originally associated with another biological function. Because human EMAP II and S. cerevisiae Arc1p are known to bind to tRNA (Simos et al., supra), the EMAP II-like motif may have been originally developed for RNA binding. The structure-specific tRNA binding activity of the EMAP II-like Trbp111 from Aquifex aeolicus is consistent with this possibility (Morales et al., 1999, EMBO J. 18:3475-83).

These results suggest that eukaryotic TyrRS molecules had opportunities to gain "cytokine" functions throughout their long evolution, by the addition of an extra domain or by accumulation of mutations. It is worth noting that the Neurospora crassa and Podospora anserina mitochondrial TyrRS molecules also have other functions (i.e., catalysis of RNA splicing) (Kämper et al., 1992, Mol. Cell. Biol. 12:499-511). These proteins contain appended domains at their amino- and carboxyl-termini when compared with other mitochondrial TyrRS molecules, and these appended domains are important for splicing (Kittle et al., 1991, Genes Dev. 5:1009-21). Thus, during the molecular evolution of aminoacyl-tRNA synthetases, attachment and removal of new domains might have occurred frequently as these ancient enzymes acquired novel functions.

EXAMPLE 10

Human Mini TyrRS Primary Structure

Figure 14:
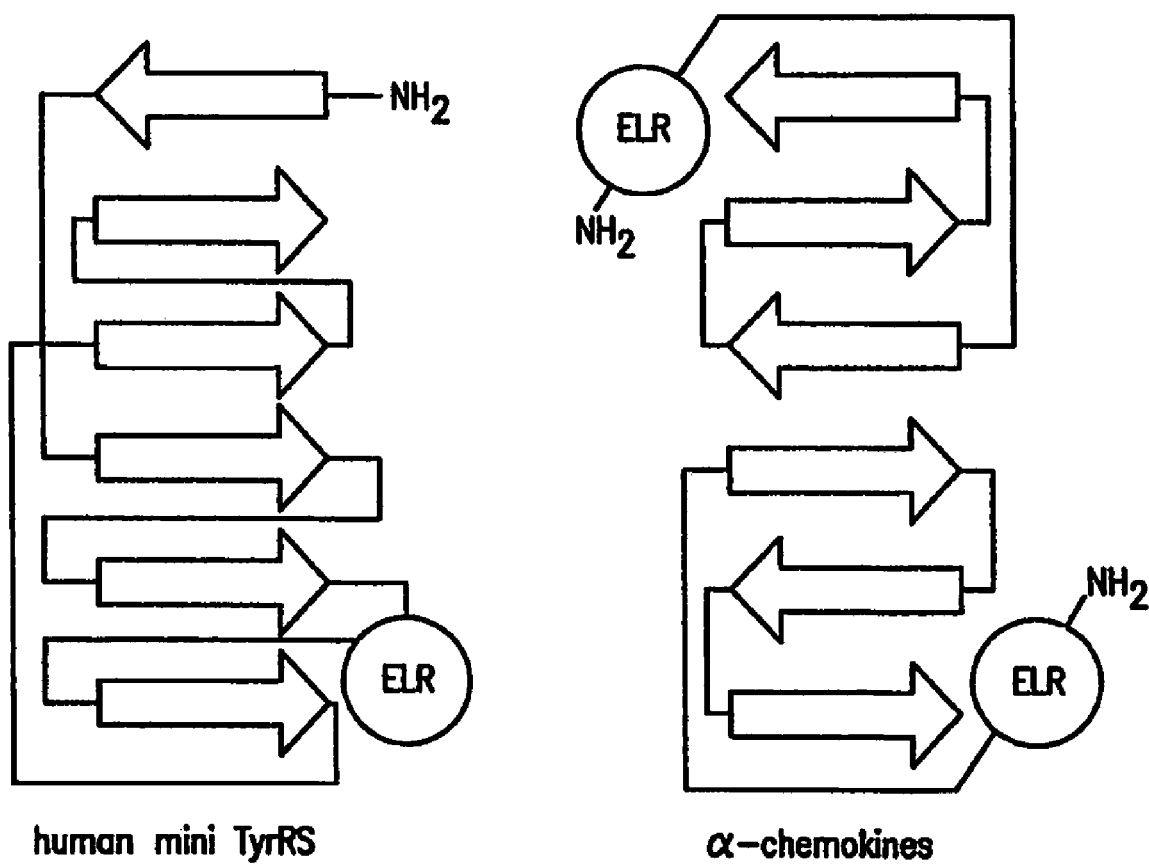
FIG. 14 illustrates a schematic comparison between human mini TyrRS and α-chemokines (the carboxyl-terminal portions of each have been omitted); the location of β-sheets (solid arrows) and ELR motifs (circles) are indicated.

Human mini TyrRS differs in primary structure from more typical α-chemokines. For example, while mini TyrRS contains an ELR motif that is critical for receptor binding, this motif is at the middle of the Rossmann fold that forms the site for synthesis of tyrosyl-adenylate. In contrast, the ELR motif of α-chemokines is located near the amino-terminus. Also, whereas α-chemokines have conserved cysteines and a Cys-Xaa-Cys motif (where Xaa is any residue), mini TyrRS does not share the conserved residues. Despite these differences in primary structures, human mini TyrRS is predicted—based on the crystal structure of Bacillus stearothermophilus TyrRS (Brick et al., 1989, J. Mol. Biol. 208:83-98)—to form the same six-stranded β-sheet as the α-chemokines (FIG. 14). Moreover, the predicted location of the ELR motif of human mini TyrRS is close to that of the α-chemokines (Clore and Gronenborn, 1991, J. Mol. Biol. 217:611-20).

A long amino-terminal segment precedes the ELR region of mini TyrRS. As the same extension occurs in the yeast and bacterial proteins examined herein, the presence or absence of this extension cannot explain the unique cytokine activity of human mini TyrRS. Many of the ELR-containing chemokines have an amino-terminal extension that is cleaved away to activate the chemokine (Brandt et al., 1991, Cytokine 3:311-21). These amino-terminal extensions may block access to the ELR motif, and it is for that reason that activation occurs upon removal of the extensions. However, the amino-terminal region of the structural model of mini TyrRS does not physically block the ELR motif and therefore this region should be accessible for cytokine activation. Consistent with this conclusion, in experiments using a fusion protein comprising the amino-terminus of IL-8 and an Fab fragment, specific binding to the IL-8 receptor induced IL-8-mediated chemotactic activity and stimulated the release of myeloperoxidase (Hölzer et al., 1996, *Cytokine* 8:214-21).

EXAMPLE 11

Induction of Endothelial Cell Migration by Human TyrRS

All α-chemokines containing the ELR motif, such as IL-8, act as angiogenic factors (Strieter et al., 1995, *J. Biol. Chem.* 270:27348-57). In contrast, α-chemokines lacking the ELR motif act as angiostatic factors (id.). In order to evaluate the angiogenic activity of TyrRS, which contains the ELR motif, human full-length TyrRS and human mini TyrRS were first examined for their ability to induce endothelial cell migration. Such angiogenic assays were performed using human umbilical vein endothelial cells (HUVECs) (Clonetics, Walkersville, Md.). Cells were maintained in EGM-2® BulletKit® medium (Clonetics) in an atmosphere of 6% $CO_2$ at 37° C. according to the supplier's instructions.

Cell migration assays were performed using the modified Boyden chamber (6.5 mm Transwells) with polycarbonate membranes (8.0 μm pore size) (Costar Corp., Cambridge, Mass.) (Masood et al., 1999, *Blood* 93:1038-44). Wells were coated overnight with 25 μg/mL human fibronectin (Biosource International, Camarillo, Calif.) in PBS and then allowed to air-dry. HUVECs were suspended in Dulbecco's modified Eagle's medium (DMEM) (Gibco-BRL, Gaithersburg, Md.) containing 0.1% BSA (Sigma) and $2 \times 10^5$ cells per well were added to the upper chamber. The chemotactic stimulus (50 nM of a given TyrRS molecule or 0.5 nM of human vascular endothelial growth factor-165 ($VEGF_{165}$) (Biosource International, Camarillo, Calif.)) was placed in the lower chamber, and the cells were allowed to migrate for 6 hours at 37° C. in a 6% $CO_2$ incubator. After incubation, non-migrant cells were removed from the upper face of the Transwell membrane with a cotton swab and migrant cells, those attached to the lower face, were fixed in methanol and visualized with the Hemacolor® stain set (EM Diagnostic Systems, Gibbstown, N.J.). Migrating cells were counted in high-power fields (HPFs). HUVECs were suspended in media with the inhibitor for 30 minutes before placement in the chamber. Each determination shown in FIG. 16 represents the average of nine HPF measurements.

Figure 16:
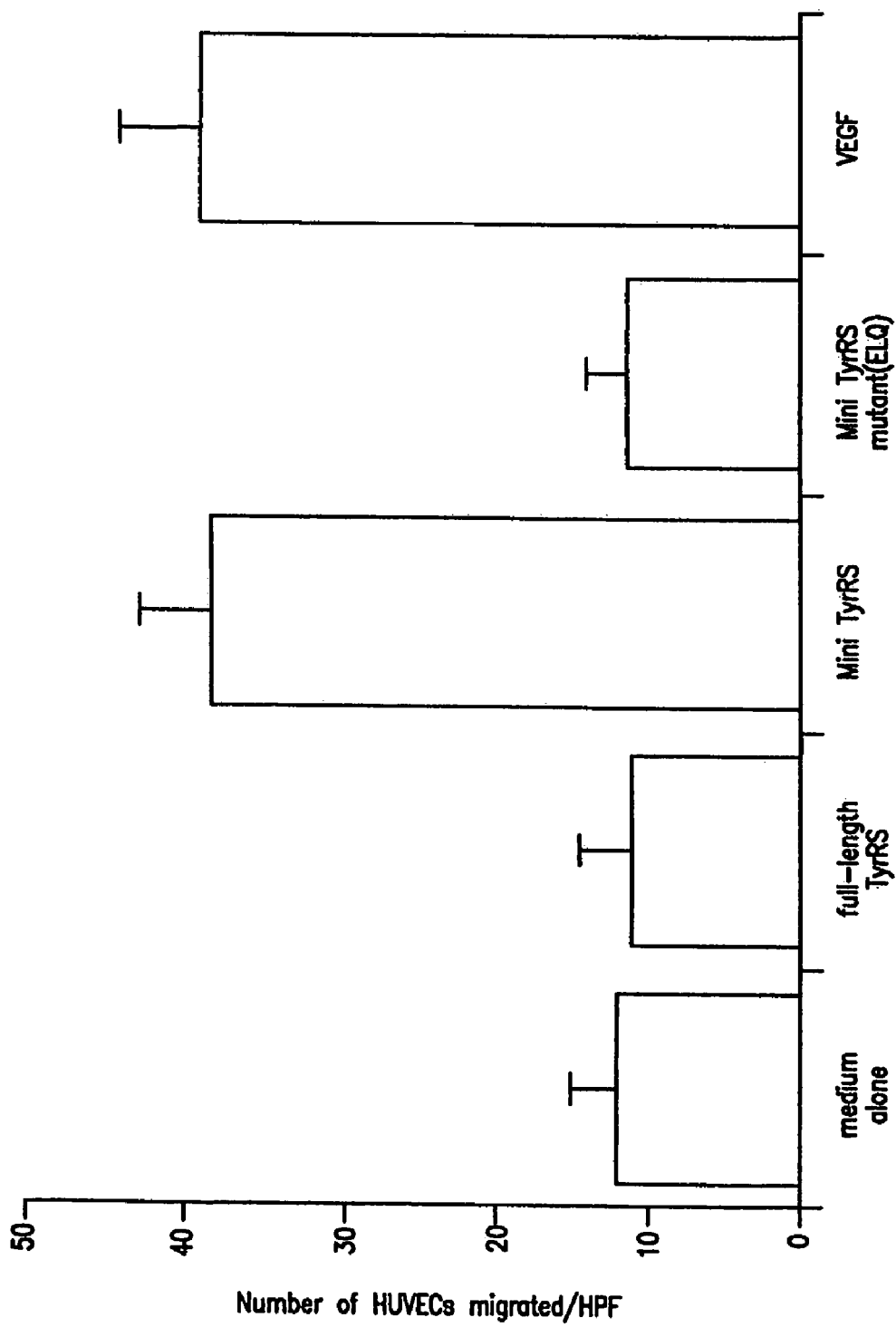
FIG. 16 illustrates the angiogenic activity of human full-length TyrRS, human mini TyrRS, human mini TyrRS mutant, or human VEGF on HUVEC chemotaxis.

As shown in FIG. 16, human mini TyrRS stimulated induction of HUVEC chemotaxis as did the positive control $VEGF_{165}$. In contrast, no chemotaxis was observed with human full-length TyrRS or human mini TyrRS mutant (containing ELQ in place of conserved ELR motif). The ability of mini TyrRS to induce directed migration of endothelial cells supported the notion that mini TyrRS also may induce angiogenesis in vivo.

EXAMPLE 12

Induction of In Vivo Angiogenesis by Human TyrRS

In vivo angiogenesis assays were conducted in chick chorioallantoic membrane (CAM) (Nicolaou et al., 1998, *Bioorg. Med. Chem.* 6:1185-208). Ten-day-old chick embryos were purchased from Mcintyre Poultry (Lakeside, Calif.) and were incubated at 37° C. and 70% humidity. A small hole was made with a small crafts drill (Dremel, Emerson Electric, Racine, Wis.) directly over the air sac at the end of the egg. The embryos were candled to determine a location to drill a second hole directly over embryonic blood vessels. Negative pressure was applied to the original hole, which resulted in the chorioallantoic membrane (CAM) pulling away from the shell membrane and creating a false air sac. A window was cut in the eggshell over the dropped CAM, exposing the CAM to direct access for experimental manipulation. Cortisone acetate-treated 5 mm filter disks were soaked with a particular protein sample (25 ng of $VEGF_{165}$ or 250 ng of a given TyrRS molecule) and the filter disks added directly to the CAMs, which were relatively devoid of preexisting blood vessels. The windows were sealed with sterile tape and incubated at 37° C. At 0, 24, and 48 hours following incubation, 3 μg of interferon-alpha inducible protein (IP-10) (R & D Systems, Minneapolis, Minn.) was topically applied to the filter disks. After 72 hours, the CAM tissue associated with the filter disk was harvested and quantified using a stereomicroscope. Angiogenesis was assessed as the number of visible blood vessel branch points within the defined area of the filter disks. Each determination shown in FIG. 17 represents the mean from 5-8 embryos.

Figure 17:
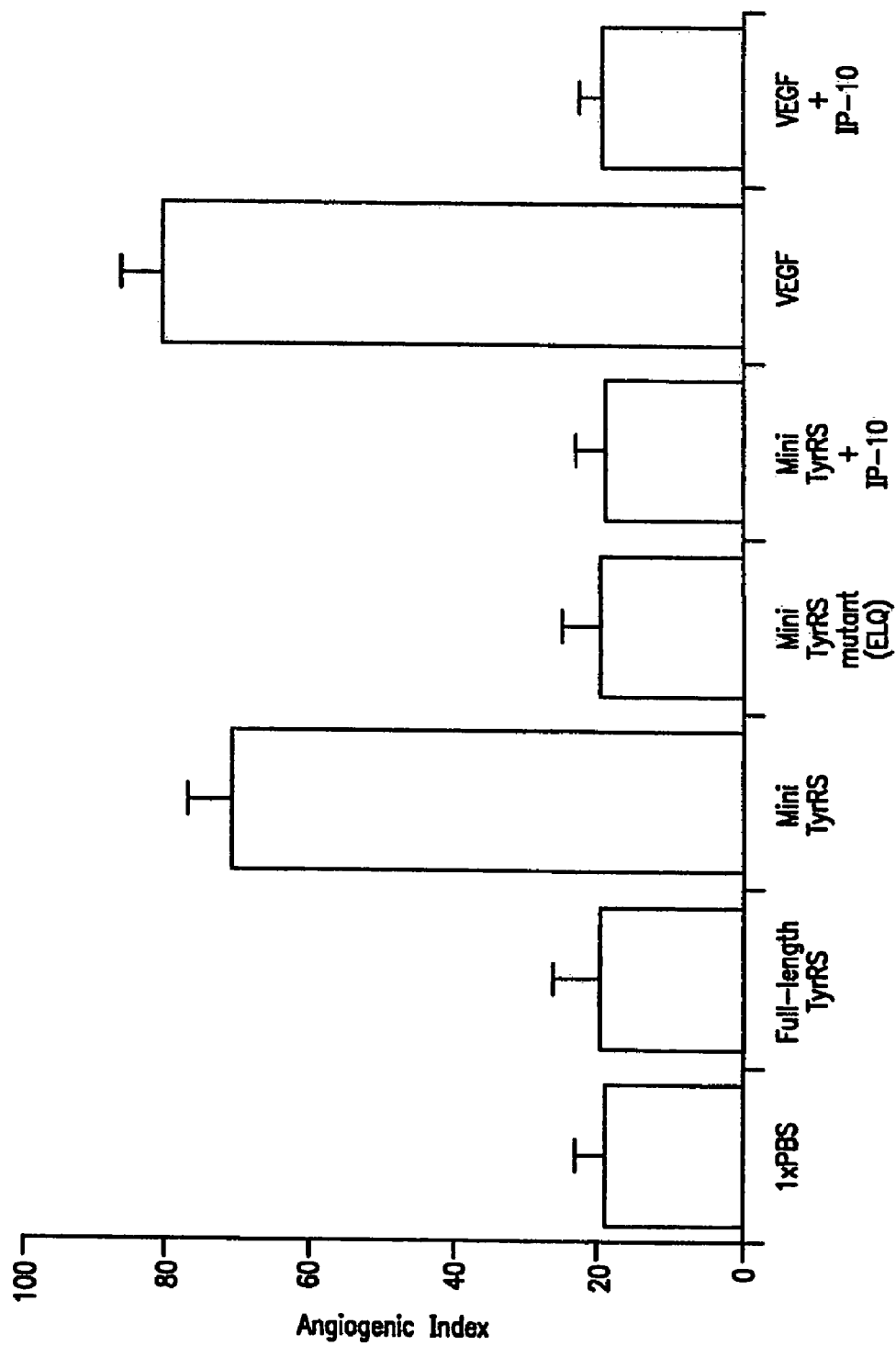
FIG. 17 illustrates the angiogenic activity of human full-length TyrRS, human mini TyrRS, human mini TyrRS mutant, human mini TyrRS+IP-10, human VEGF, or human VEGF+IP-10 on the CAMs of 10-day-old chick embryos.

As shown in FIG. 17, human mini TyrRS induced angiogenesis as did the positive control human $VEGF_{165}$. Moreover, the angiogenesis stimulated by both mini TyrRS and $VEGF_{165}$ was inhibited by the angiostatic α-chemokine, IP-10. Human mini TyrRS mutant failed to induce in vivo angiogenesis, suggesting that the ELR motif of mini TyrRS is as important for angiogenesis as the motif is for the angiogenic activity of α-chemokines.

EXAMPLE 13

Angiostatic Effect of Human TrpRS on Cell Proliferation

Expression of mini TrpRS in human cells is highly stimulated by the addition of interferon-γ (IFN-γ) (Shaw et al., 1999, *Electrophoresis* 20:984-93). Expression of the α-chemokines IP-10 (interferon-γ inducible protein) and MIG (monokine induced by interferon-γ) has also been shown to be enhanced by IFN-γ (Kaplan et al., 1987, *J. Exp. Med.* 166:1098-108; Farber, 1993, *Biochem. Biophys. Res. Commun.* 192:223-30). These α-chemokines lack the ELR motif and function as angiostatic factors both in vitro and in vivo (Strieter et al., supra). The presence in mammalian TrpRS molecules of a Rossmann nucleotide binding fold and DLT sequence, in place of the ELR motif, suggests that mammalian TrpRS molecules may function as angiostatic factors.

Figure 18:
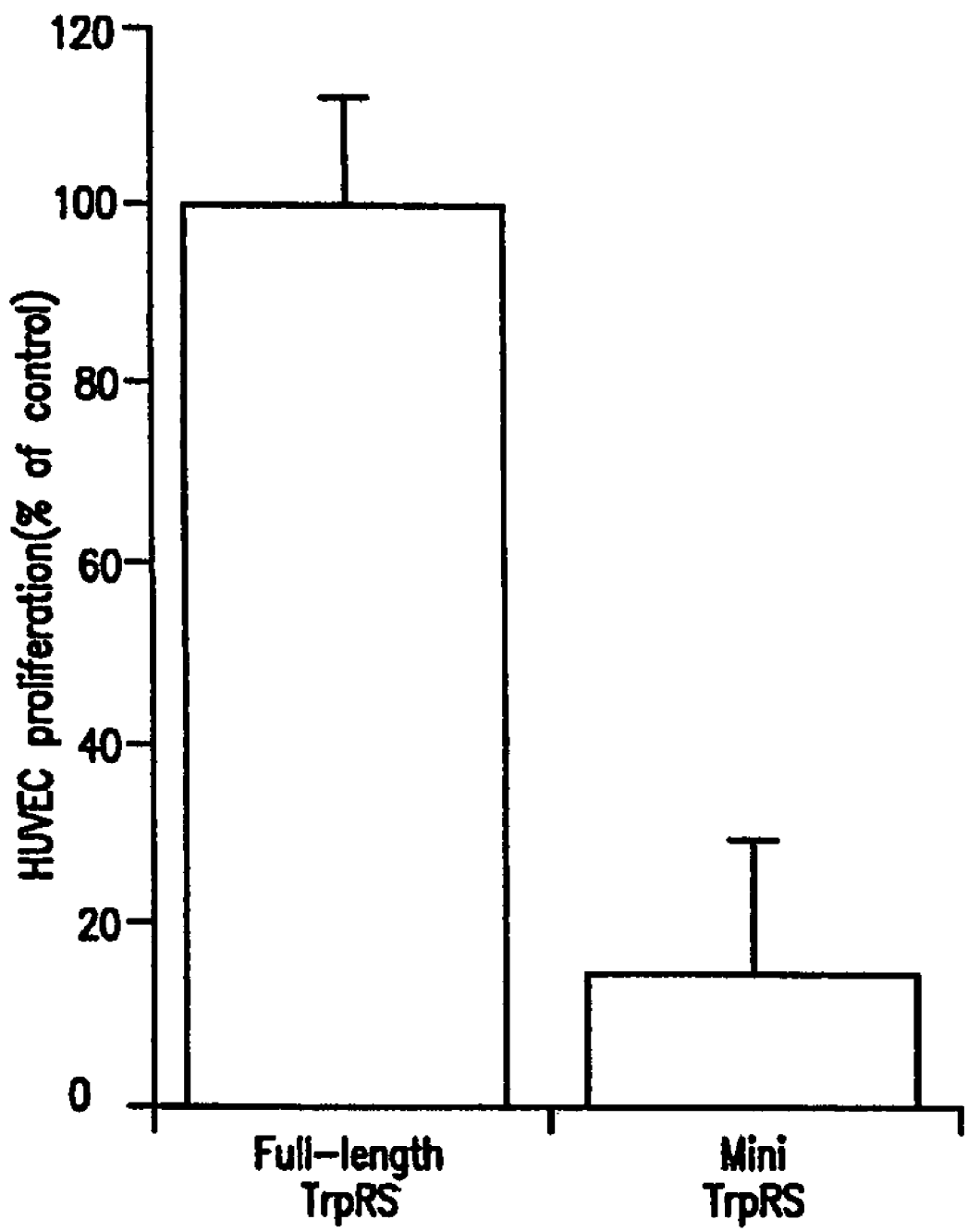
FIG. 18 illustrates the angiogenic activity of human full-length TyrRS or human mini TyrRS on endothelial cell proliferation.

The angiostatic activity of TrpRS was first evaluated in experiments testing the ability of human full-length TrpRS and human mini TrpRS to inhibit human $VEGF_{165}$-induced cell proliferation. Tissue culture-treated 96-well plates (Coming Costar Corp., Cambridge, Mass.) were coated with 0.1% gelatin (Sigma) overnight. Cells were then seeded in the gelatinized plates at a density of $5 \times 10^3$ cells per well in DMEM medium (Gibco-BRL) containing heat-inactivated fetal bovine serum (FBS) (10%, Sigma) and penicillin/streptomycin (100 units/mL-100 μg/mL, Sigma). The following day, the cells were treated with 2 μM of a given TrpRS in the presence of 2 nM $VEGF_{165}$. After 72 hours of incubation, assays were performed by using the CellTiter® 96 aqueous one-solution cell proliferation assay kit (Promega, Madison, Wis.). Results of the inhibition assay are shown in FIG. 18 as the percentage of net proliferation of $VEGF_{165}$. Each determination shown represents the mean of five experiments.

As shown in FIG. 18, human full-length TrpRS exhibited no angiostatic activity and human mini TrpRS was able to inhibit human VEGF$_{165}$-induced cell proliferation.

EXAMPLE 14

Angiostatic Effect of Human TrpRS on Endothelial Cell Migration

The angiostatic activity of TrpRS was next evaluated in experiments testing the ability of human full-length TrpRS and human mini TrpRS to inhibit human VEGF$_{165}$-induced or human mini TyrRS-induced cell migration. Cell migration assays were performed as described in Example 11 with full-length TrpRS or mini TrpRS added to VEGF$_{165}$-induced or mini TyrRS-induced HUVEC samples. HUVEC samples were treated with 0.5 nM VEGF$_{165}$, 50 nM mini TyrRS, and 500 nM of a given TrpRS. Four measurements of chemotaxis were done for each protein. Each determination shown in FIG. 19 represents the average of nine HPF measurements.

Figure 19:
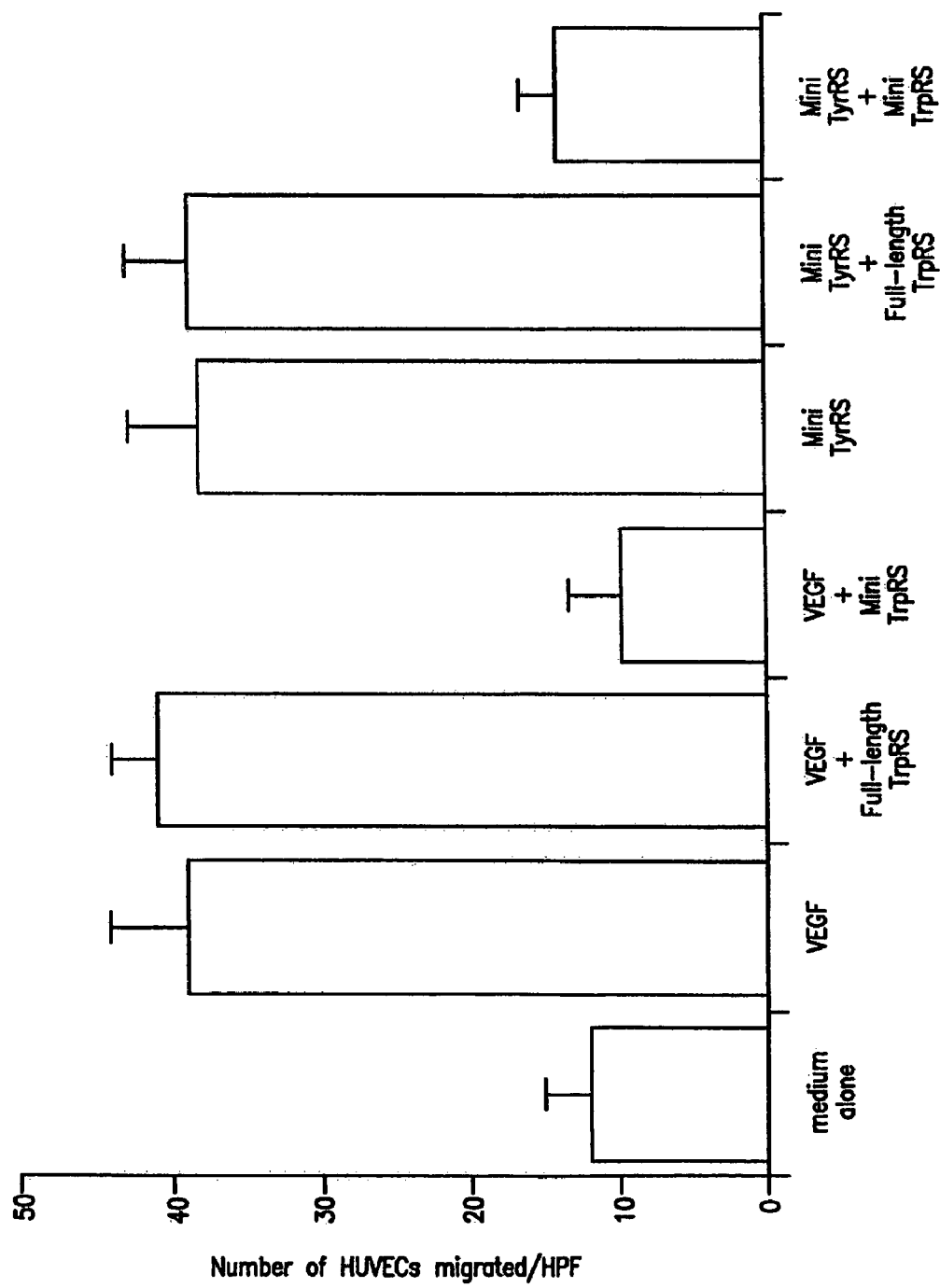
FIG. 19 illustrates the effect of human full-length TrpRS or human mini TrpRS on human VEGF-induced or human mini TyrRS-induced endothelial migration.

As shown in FIG. 19, human mini TrpRS inhibited human VEGF$_{165}$-induced and human mini TyrRS-induced HUVEC chemotaxis. In contrast, human full-length TrpRS had no effect on VEGF$_{165}$-induced or mini TyrRS-induced HUVEC chemotaxis.

EXAMPLE 15

Angiostatic Effect of Human TrpRS on In Vivo Angiogenesis

The angiostatic activity of human full-length TrpRS and human mini TrpRS was also analyzed in in vivo angiogenesis assays conducted in chick CAM. In vivo angiogenesis assays were performed as described in Example 12 with 3 µg of full-length TrpRS or mini TrpRS added to VEGF$_{165}$-induced or mini TyrRS-induced CAM tissue.

Figure 20:
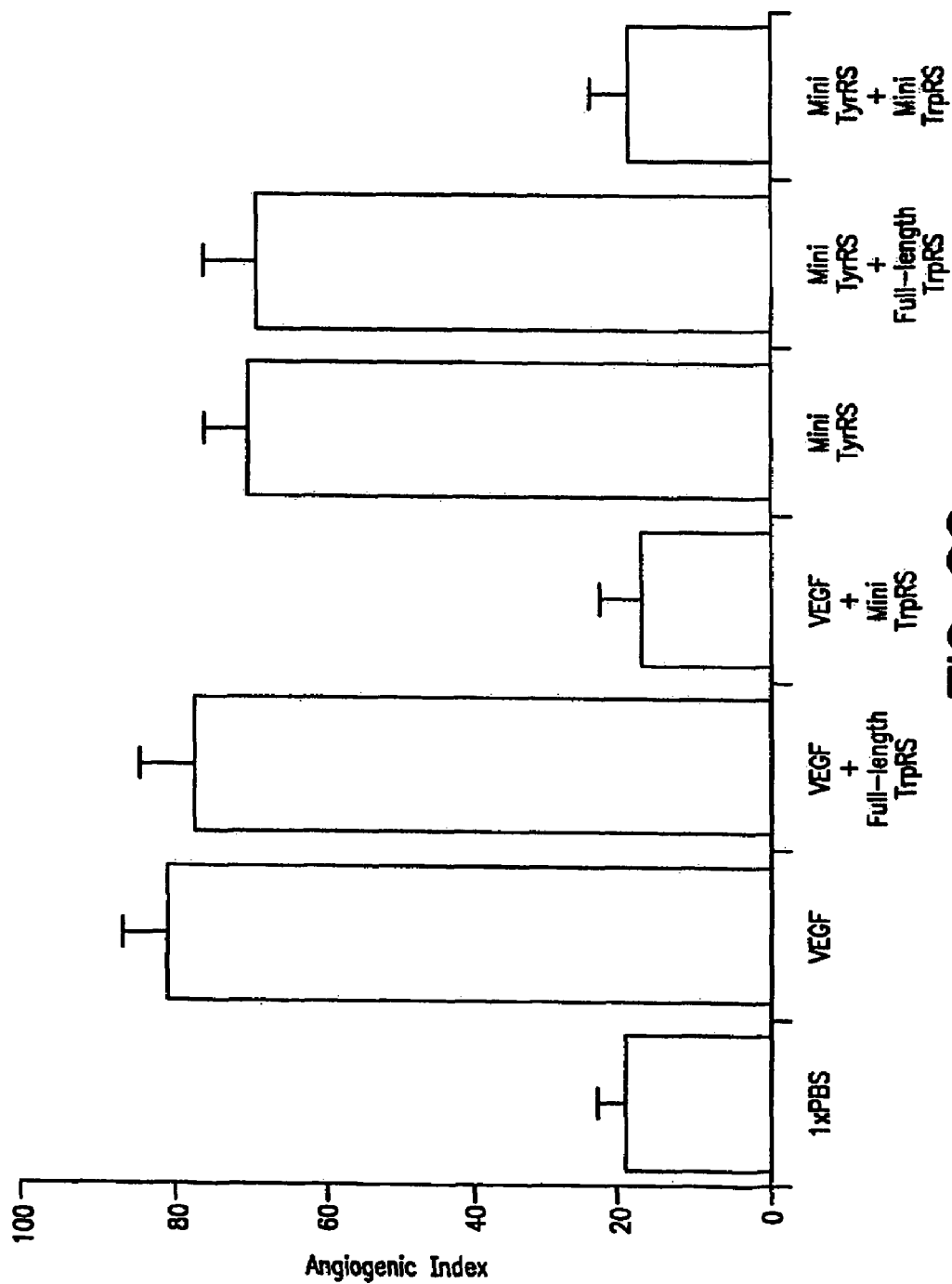
FIG. 20 illustrates the effect of human full-length TrpRS or human mini TrpRS on the angiogenic activity of human VEGF or human mini TyrRS on chick CAM.

As shown in FIG. 20, the angiogenic activity of human VEGF$_{165}$ and human mini TyrRS was inhibited by human mini TrpRS. Human full-length TrpRS had no observable angiostatic activity.

EXAMPLE 16

Secretion of Human TrpRS From U-937 Cells

As shown in Example 5, TyrRS is secreted from apoptotic tumor cells where it can be cleaved by PMN elastase to release mini TyrRS and an EMAP II-like carboxyl-domain. In contrast, several other tRNA synthetases, including AlaRS, LysRS, IleRS, and ValRS, were not found to be secreted under the same conditions. In order to determine whether TrpRS could be secreted under these conditions, secretion assays using U-937 cells were performed as described in Example 5. Cell supernatants were examined by Western blot analysis using a polyclonal anti-TrpRS antibody.

Figure 21:
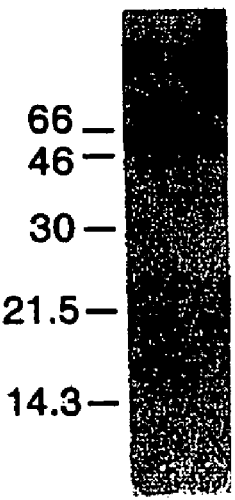
FIG. 21 illustrates the results of immunoblot analysis showing the secretion of human TrpRS from human U-937 cells.

As shown in FIG. 21, human full-length TrpRS was secreted from apoptotic U-937 cells, but not from U-937 cells maintained under normal (i.e., serum) conditions. It was not possible to determine whether human mini TrpRS was also secreted from apoptotic tumor cells, since the amount of mini TrpRS generated from full-length TrpRS is comparatively small.

EXAMPLE 17

Cleavage of Human TrpRS by PMN Elastase

Figure 22:
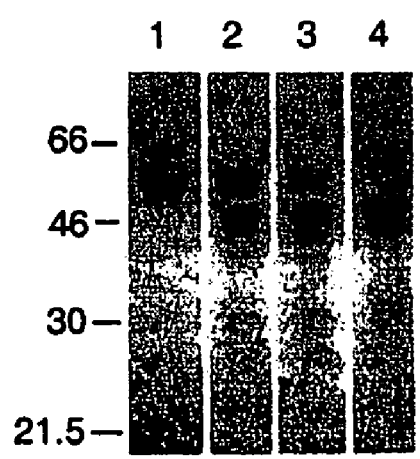
FIG. 22 illustrates the cleavage of human full-length TrpRS by PMN elastase; TrpRS was exposed to PMN elastase for 0 minutes (lane 1), 15 minutes (lane 2), 30 minutes (lane 3), or 60 minutes (lane 4)

Cleavage of human full-length TrpRS by PMN elastase was examined using the procedures similar to those described in Example 6. TrpRS was treated with PMN elastase in PBS (pH 7.4) at a protease:protein ratio of 1:3000 for 0, 15, 30, or 60 minutes. Following cleavage, samples were analyzed on 12.5% SDS-polyacrylamide gels. As shown in FIG. 22, PMN elastase cleavage of the 54 kDa full-length TrpRS generated a major fragment of 47 kDa and a minor fragment of 44 kDa. Both fragments were similar in size to the 49 kDa mini TrpRS fragment.

Western blot analysis with antibodies directed against the carboxyl-terminal His$_6$-tag of the recombinant TrpRS protein revealed that both fragments possessed the His$_6$-tag at their carboxyl-terminus. Thus, only the amino-terminus of two TrpRS fragments has been truncated. The amino-terminal sequences of the TrpRS fragments were determined by Edman degradation using an ABI Model 494 sequencer. Sequencing of these fragments showed that the amino-terminal sequences were S-N-H-G-P (SEQ ID NO: 57) and S-A-K-G-I (SEQ ID NO: 58), indicating that the amino-terminal residues of the major and minor TrpRS fragments were located at positions 71 and 94, respectively, of full-length TrpRS.

Figure 23:
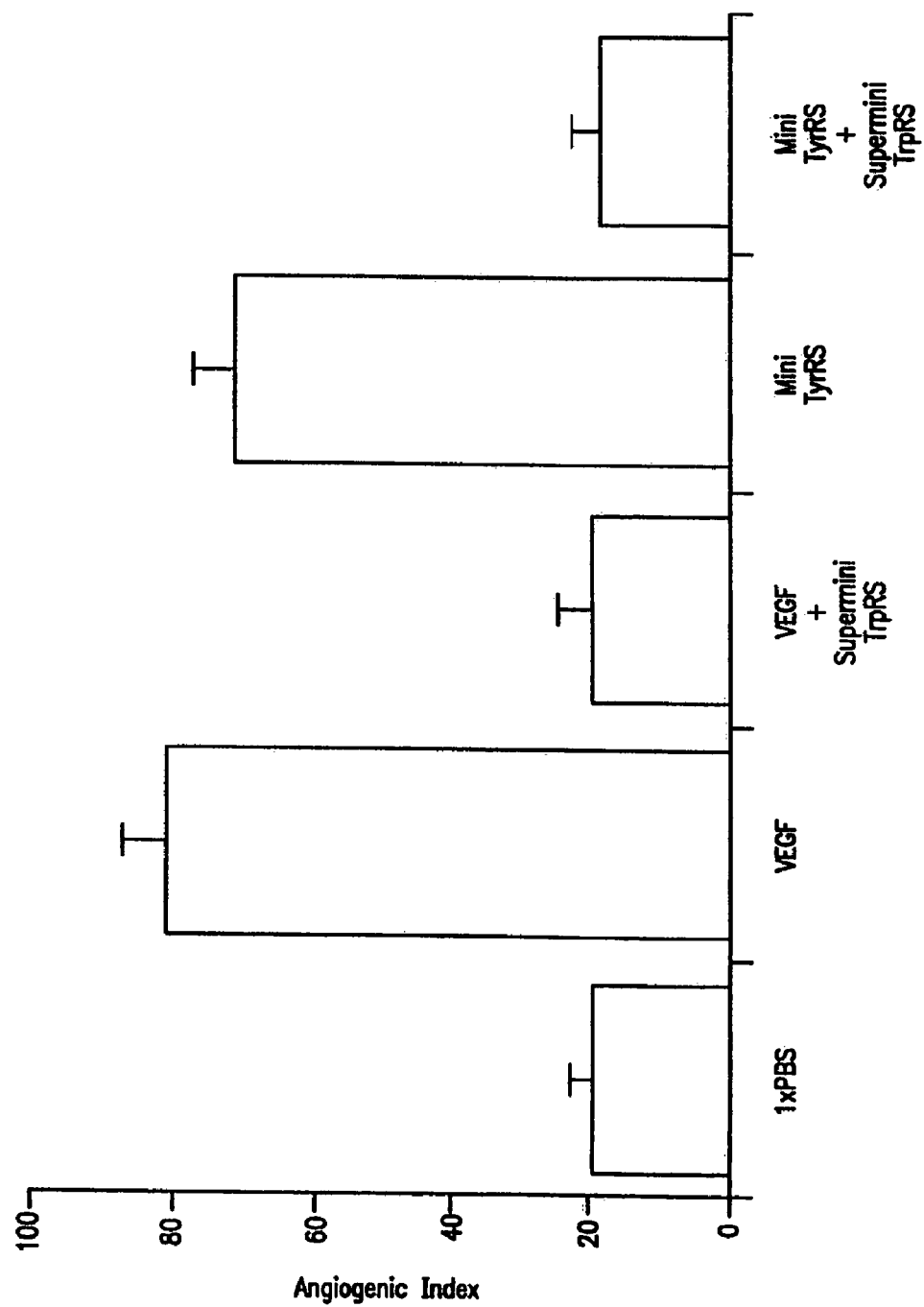
FIG. 23 illustrates the effect of human supermini TrpRS on the angiogenic activity of human VEGF or human mini TyrRS on chick CAM.

The angiostatic activity of the major and minor TrpRS fragments was analyzed in HUVEC proliferation, HUVEC migration, and chick CAM in vivo angiogenesis assays (as described in Examples 13-15). Recombinant forms of the major and minor TrpRS fragments were prepared for use in these assays. As shown in FIG. 23, the major TrpRS fragment (designated as supermini TrpRS) was capable of inhibiting VEGF$_{165}$-stimulated or human mini TyrRS-stimulated angiogenesis. Supermini TrpRS was also capable of inhibiting HUVEC proliferation and migration. Thus, the major product of PMN elastase digestion of full-length TrpRS has angiostatic activity. In contrast, the minor TrpRS fragment (designated as inactive TrpRS) did not exhibit angiostatic activity.

EXAMPLE 18

Human Mini TrpRS Primary Structure

Angiogenic mini TyrRS and angiostatic mini TrpRS and supermini TrpRS have their respective ELR and DLT motifs imbedded in closely similar Rossmann binding fold domains. In previous experiments, α-chemokines possessing the ELR motif have been shown to act as angiogenic factors and α-chemokines lacking the ELR motif have been shown to act as angiostatic factors (Strieter et al., supra). It appears that the biological balance of angiogenic (ELR) and angiostatic (non-ELR) α-chemokines regulates angiogenesis (id.). For example, the anti-tumorgenic IFN-γ induces production of IP-10 and MIG (angiostatic α-chemokines) and also attenuates the expression of IL-8 (angiogenic α-chemokine) (Gusella et al., 1993, *J. Immunol.* 151:2725-32). Similarly, in some cell lines TrpRS is highly expressed in the presence of IFN-γ.

Figure 24:
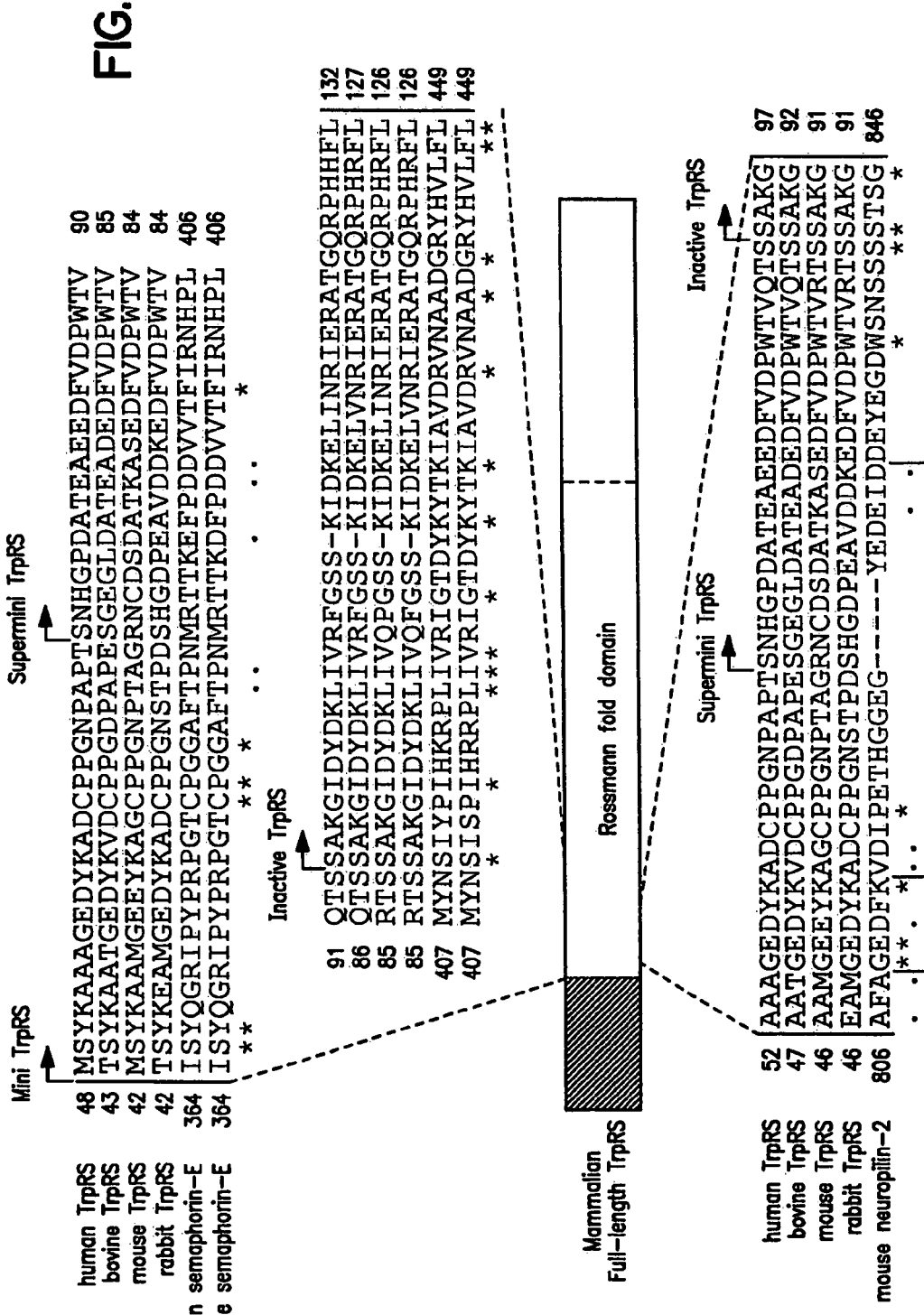
FIG. 24 illustrates the amino acid sequence similarity of human TrpRS (SEQ ID NO: 45 and SEQ ID NO: 51), bovine TrpRS (SEQ ID NO: 46 and SEQ ID NO: 52), mouse TrpRS (SEQ ID NO: 47 and SEQ ID NO: 53), rabbit TrpRS (SEQ ID NO: 48 and SEQ ID NO: 54), human semaphorin-E (SEQ ID NO: 49), mouse semaphorin-E (SEQ ID NO: 50), and mouse neuropilin-2 (SEQ ID NO: 55); the amino-terminal residue of the mini, supermini, and inactive forms of TrpRS (arrows), identical residues (asterisks), semi-conserved residues (dots), and insertions in the c-domain of neurophilin-2 (bars) are indicated.
Figure 25:
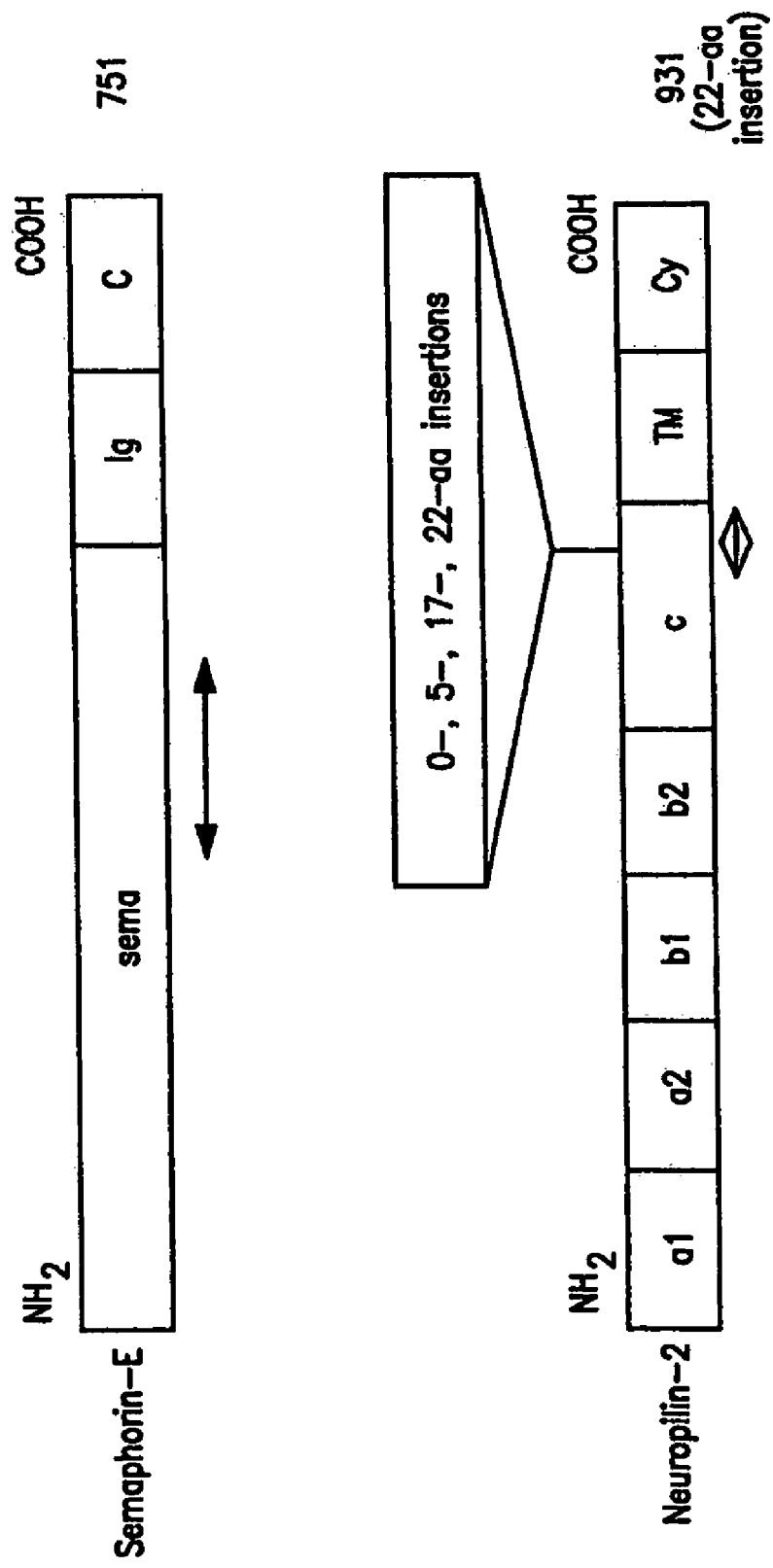
FIG. 25 illustrates the regions of semaphorin-E and neuropilin-2 that share sequence similarity with mammalian TrpRS (indicated by arrows); semaphorin-E and neuropilin-2 domains are indicated as follows: semaphorin domain (sema), immunoglobulin domain (Ig), carboxy-terminal basic domain (C), complement-binding domain (a1, a2), coagulation factor domain (b1, b2), c domain (c), transmembrane domain (TM), and cytoplasmic domain (Cy). Isoforms of neuropilin exist with insertions of 5, 17, or 22 amino acids in the c-domain.

Mammalian TrpRS shares some sequence similarity with semaphorin-E and neuropilin-2 (FIGS. 24 and 25). Neuropilin is a receptor for two unrelated ligands with disparate activities: VEGF$_{165}$, an angiogenic factor, and semaphorins, which are mediators of neuronal guidance (Chen et al., 1998, *Neuron* 21:1273-82; Neufeld et al., 1999, *FASEB J.* 13:9-22). Semaphorin-E is also a ligand for neuropilin-2 and semaphorin has been shown to be capable of blocking the binding of VEGF$_{165}$ to neuropilin (Chen et al., supra). The sequence similarity of a portion of semaphorin-E to TrpRS suggests that human mini TrpRS and human supermini TrpRS bind neuropilin-2, thereby inhibiting VEGF$_{165}$ binding to neuropilin-2. Since the shared sequence similarity between neuropilin-2 and TrpRS is located in the neuropilin-2 c-domain that is required for neuropilin-2 dimerization (Chen et al., supra) (FIG. 25), human mini TrpRS and human supermini TrpRS may inhibit the dimerization of neuropilin-2.

Mature EMAP II has been reported to be a cytokine with anti-angiogenic properties (Schwarz et al., 1999, *J. Exp. Med.* 190:341-54). The carboxyl-domain of human TyrRS has also been shown to have an EMAP II-like cytokine activity (see Example 2). Angiostatic mini TrpRS may be produced by alternative splicing of the pre-mRNA or, as shown in Example 17, angiostatic supermini TrpRS can be generated by PMN elastase cleavage. PMN elastase has been shown to be present in human colorectal carcinoma with particular enrichment at the tumor-host interface (Bjørnland et al., supra). Also, breast and non-small cell lung cancer cells are known to secrete PMN elastase in vitro (Yamashita et al., 1996, *Chest* 109:1328-34). Thus, human TyrRS and TrpRS, which are secreted from apoptotic cells, may be cleaved by PMN elastase at the tumor-host interface. The cleaved enzymes can then act as angiogenic and angiostatic factors that regulate tumor invasion.

It should be understood that the foregoing disclosure emphasizes certain specific embodiments of the invention and that all modifications or alternatives equivalent thereto are within the spirit and scope of the invention as set forth in the appended claims.

We claim:

1. An isolated nucleic acid comprising a polynucleotide encoding a polypeptide selected from the group consisting of:
   a polypeptide consisting of amino acid residues 48-471 of SEQ ID NO:10; and
   a polypeptide consisting of amino acid residues 71-471 of SEQ ID NO:10.

2. The isolated nucleic acid of claim 1 further comprising a leader polynucleotide fused to the polynucleotide encoding the mature polypeptide and in an open reading frame therewith, the leader polynucleotide encoding a secretory peptide sequence for controlling transport of the mature polypeptide from a cell.

3. A recombinant vector comprising the polynucleotide of claim 1.

4. A recombinant vector comprising the polynucleotide of claim 2.

5. A method of making a recombinant host cell comprising introducing the polynucleotide of claim 1 into the host cell.

6. An isolated recombinant host cell which includes the polynucleotide of claim 1 and expressed the polypeptide encoded by the polynucleotide.

7. An isolated recombinant host cell which includes the polynucleotide of claim 2 and expressed the polypeptide encoded by the polynucleotide.

8. The recombinant host cell of claim 7 wherein the expressed polypeptide is truncated tryptophanyl-tRNA synthetase polypeptide and further includes a secretory peptide sequence fused to the N-terminus thereof.

9. A method of making an isolated polypeptide comprising:
   (a) culturing the recombinant host cell of claim 6 in which said polypeptide is expressed; and
   (b) isolating from the cell culture a truncated tryptophanyl-tRNA synthetase polypeptide.

10. A method of making an isolated polypeptide comprising:
    (a) culturing the recombinant host cell of claim 8 in which said polypeptide is expressed; and
    (b) isolating from the cell culture a truncated tryptophanyl-tRNA synthetase polypeptide.

11. An isolated nucleic acid that encodes a truncated tryptophanyl-tRNA synthetase of having the amino acid sequence of a polypeptide of approximately 47 kD molecular weight produced by cleavage of the polypeptide of SEQ ID NO:10 with polymorphonuclear leucocyte elastase.

12. A recombinant vector comprising the isolated nucleic acid of claim 11.

13. An isolated recombinant host cell comprising the isolated nucleic acid of claim 11.

14. An isolated recombinant host cell that expresses a truncated tryptophanyl-tRNA synthetase encoded by the nucleic acid of claim 11.

15. The recombinant host cell of claim 14 wherein the truncated tryptophanyl-tRNA synthetase polypeptide further includes a secretory peptide sequence fused to the N-terminus thereof.

16. A method of making an isolated polypeptide comprising:
   (a) culturing the recombinant host cell of claim 14 in which said polypeptide is expressed; and
   (b) isolating expressed polypeptide from the cell culture.

17. A method of making an isolated polypeptide comprising:
   (a) culturing the recombinant host cell of claim 15 in which said polypeptide is expressed; and
   (b) isolating expressed polypeptide from the cell culture.

\* \* \* \* \*

UNITED STATES PATENT AND TRADEMARK OFFICE
CERTIFICATE OF CORRECTION

PATENT NO. : 7,521,215 B2
APPLICATION NO. : 11/444924
DATED : April 21, 2009
INVENTOR(S) : Paul Schimmel et al.

Page 1 of 1

It is certified that error appears in the above-identified patent and that said Letters Patent is hereby corrected as shown below:

Column 117,
Lines 62 and 65, "expressed" should be -- expresses --.

Signed and Sealed this

Seventeenth Day of November, 2009

David J. Kappos
*Director of the United States Patent and Trademark Office*